US006326176B1

(12) United States Patent
Barbas et al.

(10) Patent No.: US 6,326,176 B1
(45) Date of Patent: Dec. 4, 2001

(54) ALDOL CONDENSATIONS BY CATALYTIC ANTIBODIES

(75) Inventors: Carlos F. Barbas, Del Mar; Richard A. Lerner, La Jolla; Guofu Zhong; Benjamin List, both of San Diego, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/573,753

(22) Filed: May 18, 2000

Related U.S. Application Data

(63) Continuation-in-part of application No. PCT/US98/26942, filed on Dec. 18, 1998.
(60) Provisional application No. 60/135,411, filed on May 21, 1999, and provisional application No. 60/068,049, filed on Dec. 18, 1997.

(51) Int. Cl.[7] .......................................................... C12P 7/26
(52) U.S. Cl. ........................................ 435/148; 435/188.5
(58) Field of Search ................................. 435/148, 188.5

(56) References Cited

U.S. PATENT DOCUMENTS

| | | | |
|---|---|---|---|
| 5,571,681 | 11/1996 | Janda et al. | 435/216 |
| 5,733,757 | * 3/1998 | Barbas et al. | 435/148 |
| 5,985,626 | 11/1999 | Barbas et al. | 435/128 |

OTHER PUBLICATIONS

Barbas, et al., "Semisynthetic Combinatorial Antibody Libraries: A Chemical Solution to the Diversity Problem", *Proc. Natl. Acad. Sci. USA 89*: 4457–4461 (1992).
Lerner, et al., "Antibodies Without Immunization", *Science 258*: 1313–1314 (1992).
Burton, "Monoclonal Antibodies from Combinatorial Libraries", *Acc. Chem. Res. 26*: 405–411 (1993).
Barbas, et al., "Selection of human anti–hapten antibodies from semisynthetic libraries", *Gene 137*: 57–62 (1993).
Barbas, et al., "Direct Selection of Antibodies that Coordinate Metals from Semisynthetic Combinatorial Libraries", *Proc. Natl. Acad. Sci. USA 90*: 6385–6389 (1993).
Lerner, et al., "Using the Process of Reactive Immunization to Induce Catalytic Antibodies with Complex Mechanisms: Aldolases", *Acta Chem. Scan. 50*: 672–678 (1996).
Barbas, et al., "Immune Versus Natural Selection: Antibody Aldolases with Enzymic Rates but Broader Scope", *Science 278*: 2085–2092 (1997).

Page, et al., "Entropic Contributions to Rate Acceleration in Enzymic and Intramolecular Reactions and the Chelate Effect", *Proc. Natl. Acad. Sci. USA 68*: 1678–1683 (1971).
Lerner, et al., "At the Crossroads of Chemistry and Immunology: Catalytic Antibodies", *Science 252*: 659–667 (1991).
Barbas III, et al., "Assembly of Combinatorial Antibody Libraries on Phage Surfaces: The Gene III Site", *Proc. Natl. Acad. Sci. USA 88*: 7978–7982 (1991).
Janda, et al., "Direct Selection for a Catalytic Mechanism from Combinatorial Antibody Libraries", *Proc. Natl. Acad. Sci. USA 91*: 2532–2536 (1994).
Bach, "Catalytic Enantioselective C–C Coupling–Allyl Transfer and Mukaiyama Aldol Reaction", *Angew. Chem. Int. Ed. Engl. 33*: 417–419 (1994).
Morris, et al., "Lysine–146 of Rabbit Muscle Aldolase in Essential for Cleavage and Condensation of the C3–C4 Bond of Fructose 1,6–Bis(phosphate)", *Biochemistry 33*: 12291–12297 (1994).
Teraishi, et al., "Design of the Hapten for the Induction of Antibodies Catalyzing Aldol Reaction", *J. Mol. Graphics 12*: 282–285 (1994).
Carreira, et al., "Catalytic, Enantioselective Acetone Aldol Additions with 2–Methoxypropene", *J. Am. Chem. Soc. 117*: 3649–3650 (1995).
Reymond, et al., "Catalytic, Enantioselective Aldol Reaction with an Artificial Aldolase Assembled from a Primary Amine and an Antibody", *J. Org. Chem. 60*: 6970–6979 (1995).
Wagner, J., et al. (1995) Science 270, 1797–1800.*
Flanagan, M.E., et al. (1996) J. Am. Chem. Soc. 118, 6078–6079.*
Bjornestedt, R., et al. (1996) J. Am. Chem Soc. 118, 11720–11724.*

* cited by examiner

*Primary Examiner*—Charles L. Patterson, Jr.
(74) *Attorney, Agent, or Firm*—Thomas E. Northrup

(57) ABSTRACT

Catalytic antibodies, including 38C2 and 33F12, are capable of efficiently catalyzing a wide variety of ketone-ketone, ketone-aldehyde, aldehyde-ketone, and aldehyde-aldehyde intermolecular aldol reactions, and in some cases to catalyze their subsequent dehydration to yield aldol condensation products. A number of intramolecular aldol reactions have also been defined. Catalysis of all intramolecular aldol reactions examined yields the corresponding condensation products.

19 Claims, 45 Drawing Sheets

$R^1$ = (FG)-alkyl, (FG)-alkenyl, (FG)-aryl
$R^2$ = H, OH, F
X = $NCH_3$, O, S, $CH_2$, $C_6H_4$
FG = OH, $OCH_3$

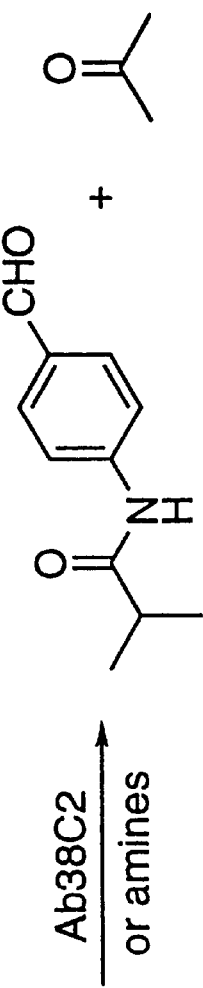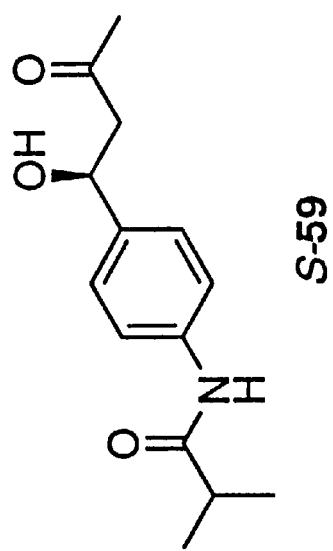
FIG. 12

| donor | product(s) | specific rate |
|---|---|---|
| acetone | 9: R-CH₂CH₂-CH(OH)-C(O)-CH₃ | 2.5 |
| 2-butanone | 10a: R-CH₂CH₂-CH(OH)-CH(CH₃)-C(O)-CH₃<br>10b: R-CH₂CH₂-CH(OH)-C(O)-CH₂CH₃ | 3.7 |
| 2-pentanone | 11a: R-CH₂CH₂-CH(OH)-CH(Et)-C(O)-CH₃<br>11b: R-CH₂CH₂-CH(OH)-C(O)-CH₂CH₂CH₃ | 0.4[a] |
| 3-pentanone | 12: R-CH₂CH₂-CH(OH)-CH(CH₃)-C(O)-CH₂CH₃ | 0.6[a] |
| cyclopentanone | 13 | 6.4 |
| cyclohexanone | 14 | nd[b] |
| hydroxyacetone | 15 | 54.3 |
| fluoroacetone | 16 | 5.5 |
| 2-hydroxycyclohexanone | 17 | nd[b] |

[a] Specific rate was determined with 200 mM donor. [b] Not determined.

FIG. 13

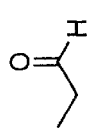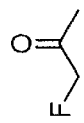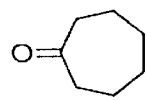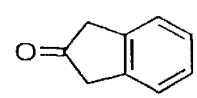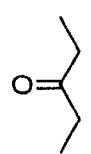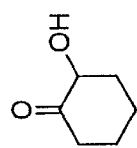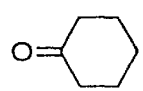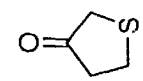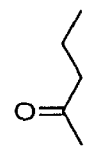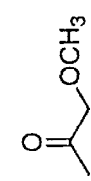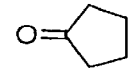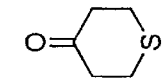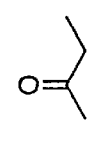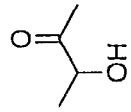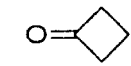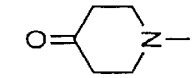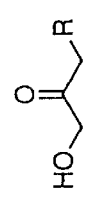
FIG. 14

FIG. 15
| acceptor | donor | product(s) | specific rate |
|---|---|---|---|
| 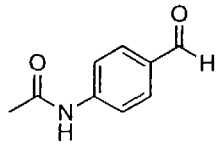 3 | acetone | 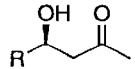 (18) | 18.1 |
| | cyclopentanone | 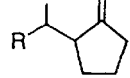 (19) | 0.4 |
| | hydroxyacetone | 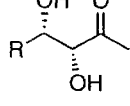 (20) | 71.6 |
| 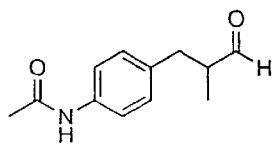 5 | acetone | 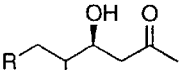 (21) | 21.5 |
| | cyclopentanone | 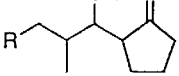 (22) | 15.9 |
| | hydroxyacetone | 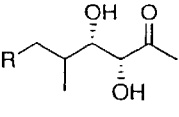 (23) | 42.5 |
| 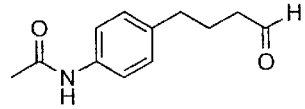 6 | acetone | 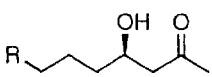 (24) | 4.3 |
| | cyclopentanone | 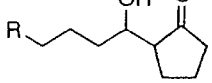 (25) | 142.1 |
| | hydroxyacetone | 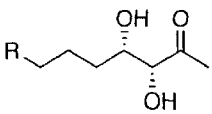 (26) | 103.9 |
| 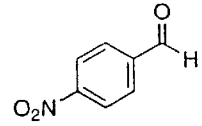 7 | acetone | 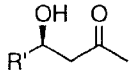 (27) | 92.3 |
| | cyclopentanone | 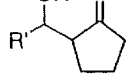 (28) | 82.1 |
| | hydroxyacetone | 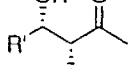 (29) | 219.9 |
| 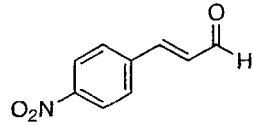 8 | acetone | 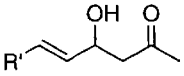 (30) | 35.9 |
| | cyclopentanone | 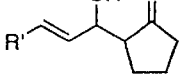 (31) | 11.1 |
| | hydroxyacetone | 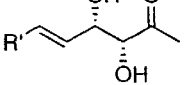 (32) | 96.2 |

| substrate | product/intermediate | specific rate |
|---|---|---|
| propanal | 2-methyl-2-pentenal (33) | 97.4 |
| acetone | mesityl oxide (34) | < 0.1 |
| cyclopentanone | cyclopentylidenecyclopentanone (35) | 0.1 |
| cyclopentanone | 2-(1-hydroxycyclopentyl)cyclopentanone (36) | 10.3 |
| 2-(1-hydroxycyclopentyl)cyclopentanone (36) | cyclopentylidenecyclopentanone (35) | 4.3 |

FIG. 16

| sub-strate | $K_M$ [mM] | $k_{cat}$ [min$^{-1}$] | $k_{uncat}$ [min$^{-1}$] | $k_{cat}/k_{uncat}$ |
|---|---|---|---|---|
| 39 | 2.05 | 0.082 | $6.7 \cdot 10^{-9}$ | $1.2 \cdot 10^7$ |
| 43 | 2.34 | 0.086 | $2.4 \cdot 10^{-8}$ | $3.6 \cdot 10^6$ |
| (S)-45 | 12.4 | 0.186 | nd[a] | nd[a] |
| (R)-45 | 2.45 | 0.126 | nd[a] | nd[a] |

[a] Not determined.

FIG. 17

| acceptor | donor | product | specific rate |
|---|---|---|---|
| n-C$_6$H$_{13}$CHO | cyclopentanone | 51 | 17 |
| n-C$_5$H$_{11}$CHO | cyclopentanone | 52 | 10 |
| n-C$_4$H$_9$CHO | cyclopentanone | 53 | 115 |
| n-C$_4$H$_9$CHO | hydroxyacetone | 54 | nd[a] |
| n-C$_4$H$_9$CHO | 2-hydroxy-cyclopentanone | 55 | nd[a] |
| n-C$_4$H$_9$CHO | 2-hydroxy-cyclohexanone | 56 | nd[a] |

[a] Not determined

FIG. 18

| product | | ee | |
|---|---|---|---|
| | | 38C2 | 33F12 |
| 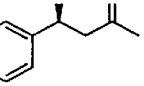 | (57) | > 99 % | > 99 % |
| 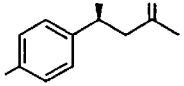 | (18) | 98 % | 99 % |
| 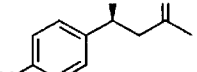 | (59) | > 99 % | > 99 % |
| 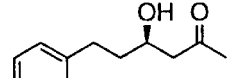 | (9) | 58 % | 69 % |
| 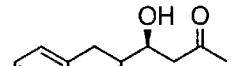 | (S-21) | de > 95 % | de > 95 % |
| 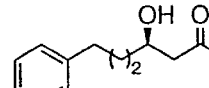 | (24) | 20 % | 3 % |
| 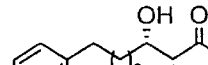 | (58) | 77 % (de > 99 %) | 70 % (de > 99 %) |
| 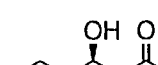 | (27) | 98 % | 99 % |
| 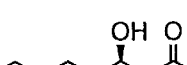 | (30) | 99 % | 98 % |
| 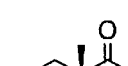 | S-(44) | > 95 % | > 95 % |
| 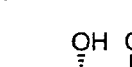 | (54) | > 98 % | 89 % |
FIG. 19

FIG. 20

| Amine/Solvent | $(k_{cat}/K_m)^a/K_{amine}$ | $k_{cat}/k_{amine}$ (M) |
|---|---|---|
| n-butylamine/MOPS[b] | $1.3 \times 10^8$ | $3.5 \times 10^4$ |
| n-butylamine/n-octanol | $2.1 \times 10^6$ | $5.6 \times 10^2$ |
| aminoacetonitrile/MOPS[b] | $2.9 \times 10^7$ | $7.8 \times 10^3$ |
| aminoacetonitrile/ n-octanol | $1.6 \times 10^7$ | $4.2 \times 10^3$ |

[a] $k_{cat}$ and $K_m$ of antibody 38C2 catalyzed retroaldolization (FIGURE 12).
[b] 100mM MOPS buffered water, pH 7.0, 25C.

FDP Aldolase Class I
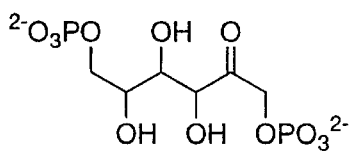
Ab 38C2 or 33F12
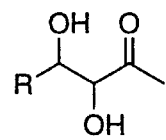
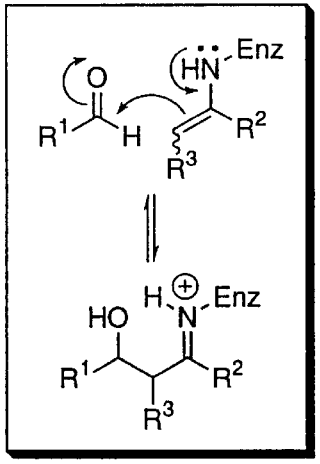
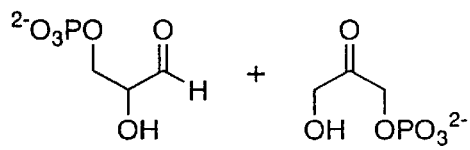
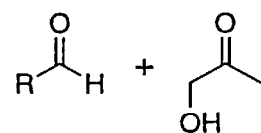
FIG. 25

FIG. 26

| substrate(s)/product | $k_{cat}$ [min-1] | $k_{cat}/k_{uncat}$ |
|---|---|---|
| | 0.086 | $3.6 \cdot 10^6$ |
| | 2.14 | nd |
| | $3 \cdot 10^{-4}$ | nd |
| | 1.02 | nd |

| COMPOUND | rate (a) | ee (%) | dr (syn:anti) |
|---|---|---|---|
| 8000α | 0.65 min⁻¹ (b) | >99 | 4:1 |
| 8000β | 0.03 min⁻¹ (b) | >99 | — |
| 11000α | 0.24 (c) | >99 | 5:1 |
| 11000β | 0.24 (c) | >99 | — |

FIG. 39

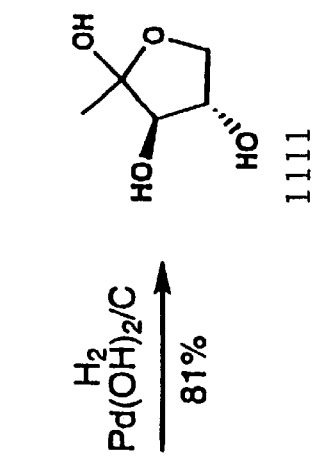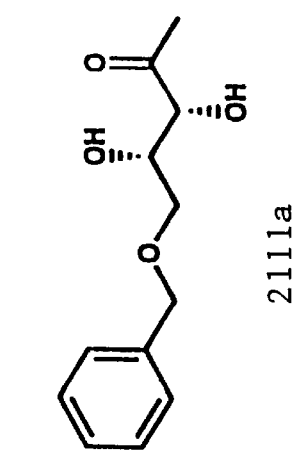
FIG. 41
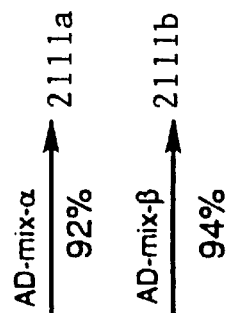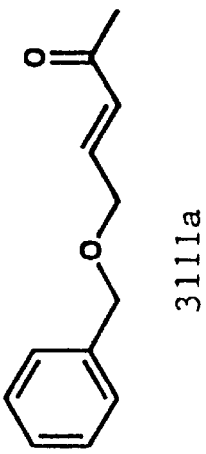
FIG. 42

*Enantioface*     *Enantiogroup*
*Differentiation*    *Differentiation*

Ab 38C2 : 94%, (96% ee)
(L)-Proline : 83%, (71% ee)

(L)-Proline : ~ 30%, (0-47% ee)

38C2: This work

| (S)-4 | R | ee |
|---|---|---|
| a | Ph | 42% |
| b | n-C₅H₁₁ | 46% |
| c | pAcNHC₆H₄CH₂CH₂ | 62% |

| (R)-4 | R | ee | |
|---|---|---|---|
| a | Ph | 47% | |
| b | n-C₅H₁₁ | 20% | |
| d | Me | 42% | ref. 15 |
| e | i-Pr | 8% | |
| f | t-Bu | 0% | |

ALDOL CONDENSATIONS BY CATALYTIC ANTIBODIES

CROSS REFERENCE TO RELATED APPLICATIONS

This application is a continuation-in-part of U.S. patent application Ser. No. 60/135,411 (filed May 21, 1999) and International Application No. PCT/US98/26942 filed Dec. 18, 1998, which is itself a continuation-in-part of U.S. patent application Ser. No. 60/068,049 (filed Dec. 18, 1997). The disclosures of all the above patent applications are incorporated herein by reference.

Funds used to support some of the studies reported herein were provided by the National Institutes of Health (CA27489). The United States Government may therefore have certain rights in this invention.

FIELD OF THE INVENTION

The invention is directed to the substrate specificity, synthetic scope, and efficiency of aldolase catalytic antibodies 38C2 and 33F12. More particularly, these antibodies are shown to catalyze intermolecular ketone-ketone, ketone-aldehyde, aldehyde-ketone, and aldehyde-aldehyde aldol addition reactions and in some cases to catalyze their subsequent dehydration to yield aldol condensation products. Substrates for intramolecular aldol reactions are also identified.

BACKGROUND

The aldol reaction is arguably one of the most important C—C bond forming reactions employed in synthetic transformations. Traditionally, the aldol reaction has been a proving ground for the development of asymmetric synthetic strategies. In the 1980's the aldol reaction experienced a renaissance with the development of numerous strategies to effect highly stereoselective aldols (For reviews of the adol reaction, see Heathcock, C. H. in *Asymmetric Synthesis*, Morrison, J. D., ed., Academic Press, New York, Vol. 3, 1984; Evans et al *Topics in Stereochemistry* 1982, 12, 1; Masamune et al. *Angew. Chem. Int. Ed. Engl.* 1985, 24, 1; Heathcock et al. *Aldrichim. Acta* 1990, 23, 99.; Heathcock, C. H. *Science* 1981, 214, 395.; Evans, D. A. ibid. 1988, 240, 420.; Masamune et al. *Angew. Chem. Int. Ed. Engl.* 1985, 24, 1.; Evans, D. A.; Nelson, J. V.; Taber, T. R. *Top Stereochem.* 1982, 13, 1.; Heathcock, C. H.; et al, in *Comprehensive Organic Synthesis*, Trost, B. M., Ed. (Pergamon, Oxford, 1991), Vol. 2, pp. 133–319; Peterson, I. *Pure Appl. Chem.* 1992, 64, 1821).

Generally, this has been most successfully achieved through the use of stoichiometric quantities of chiral auxiliaries. In recent years the design of stereoselective catalysts of the aldol reaction has become a topic of interest. Most notable of these approaches is the Carreira aldol reaction where a chiral Ti(IV) complex (2–10 mol %) catalyzes the enantioselective addition of 2-methoxypropene to aldehydes with 66–98% ee (Yanagisawa, A; Matsumoto, Y.; Nakashima, H.; Asakawa, K.; Yamamoto, H. *J. Am. Chem. Soc.* 1997, 119, 9319., and references therein; Bach, T. *Angew. Chem. Int. Ed. Engl.* 1994, 33, 417., and references therein; Yamada, Y. M. A.; Yoshikawa, N.; Sasai, H.; Shibasaki, M. *Angew. Chem. Int. Ed. Engl.* 1997, 36, 1871. (b) Carreira, E. M.; Lee, W.; Singer, R. A. *J. Am. Chem. Soc.* 1995, 117, 3649).

As a challenge to traditional organic methodology, the application of natural aldolase enzymes as synthetic catalysts has yielded numerous efficient syntheses of stereochemically complex molecules, particularly in the area of carbohydrate synthesis . Since no asymmetric catalysts exhibits the scope of reactivity required to meet every synthetic challenge there is a need for methodologies that allow for the development of asymmetric catalysts. This is true of both transition metal based as well as enzyme based catalysts. For example, while the Carreira Ti(IV) complex is limited in scope to the use of the enolate equivalent 2-methoxypropene, fructose 1,6-diphosphate aldolase is limited to the use of dihydroxyacetone phosphate as the aldol donor substrate (Gijsen, H. J. M.; Qiao, L.; Fitz,W.; Wong, C.-H. *Chem. Rev.* 1996, 96, 443. (b) Wong, C.-H.; Halcomb, R. L.; Ichikawa, Y.; Kajimoto, T. *Angew. Chem. Int. Ed. Engl.* 1995, 34, 412–432. (b)Henderson, I.; Sharpless, K. B.; Wong, C.-H. *J. Am. Chem. Soc.* 1994, 116, 558. (c) Wong, C.-H.; Whitesides, G. M. *Enzymes in Synthetic Organic Chemistry* (Pergamon, Oxford, 1994); Bednarski, M. D., in *Comprehensive Organic Synthesis*, Trost, B. M., Ed (Pergamaon, Oxford, 1991), vol. 2, 455; Gijsen, H. J. M., Wong, C.-H. ibid. 1995, 117, 2947; Wong, C.-H. et al. ibid. 1995, 117, 3333; Chen, L.; Dumas, D. P., Wong, C.-H. ibid. 1992, 114, 741).

To address the problem of the de novo generation of protein catalysts of the aldol reaction, we recently described the development of two aldolase catalytic antibodies 38C2 and 33F12. These antibodies were raised against the β-diketone hapten 1 which served as a chemical trap to imprint the lysine-dependent class I aldolase mechanism in the active site of the antibody. The suggested mechanism for the selection process of antibodies 38C2 and 33F12 during immunization is shown in FIG. 6. The ε-amino group of the lysine residue reacts with a carbonyl function of the β-diketone moiety of 1 to form a β-keto hemiaminal followed by dehydration to give a β-keto imine that finally tautomerizes into a stable enaminone 2. Consequently, the hapten is now covalently bound in the binding pocket. The mechanistic similarity between this stoichiometric reaction and the accepted enamine mechanism of class I aldolase enzymes has been discussed in detail elsewhere (Wagner, J.; Lerner, R. A.; Barbas III, C. F. *Science* 1995, 270, 1797. (b) Zhong, G.; Hoffmann, T.; Lerner, R. A.; Danishefsky, S.; Barbas III, C. F. *J. Am. Chem. Soc.* 1997, 119, 8131. (c) Barbas III, C. F.; Heine, A.; Zhong, G.; Hoffmann, T.; Gramatikova, S.; Björnestedt, R.; List, B.; Anderson, J.; Stura, E. A.; Wilson, E. A.; Lerner, R. A. *Science* 1997, 278, 2085).

The formation of the enaminone has been monitored by UV spectroscopy (with hapten 1: lmax=318 nm, ε~15000) and is complete within seconds to a few minutes, depending on whether antibodies were incubated with hapten 1, or other diketones such as 2,4-pentanedione or 3-methyl 2,4-pentanedione. Antibodies 38C2 and 33F12 have been previously shown to catalyze aldol reactions of some aliphatic ketones donors with two different aldehyde acceptors having a 4-acetanilide substituent in the β-position as well as intramolecular aldol reactions that allowed for our recent antibody catalyzed synthesis of the Wieland-Miescher ketone (Zhong et al., ibid). Moreover, both antibodies were found to catalyze the decarboxylation reactions of aromatic β-keto acids by the formation of a Schiff base between the ε-amino group of the lysine residue and the keto group of the substrate (Björnestedt, R.; Zhong, G.; Lerner, R. A.; Barbas III, C. F. *J. Am. Chem. Soc.* 1996, 118, 11720).

What is needed is antibodies which can catalyze many aldol addition reactions with varying substrates producing desired enantiomeric outcomes and in some cases to catalyze their subsequent dehydration to yield aldol condensation products.

BRIEF SUMMARY OF THE INVENTION

The invention is directed to the use of catalytic antibodies for catalyzing aldol condensation reactions and retroaldol reactions.

One aspect of the invention is directed to a method for catalyzing an aldol condensation between an aldol donor substrate and an aldol acceptor substrate for producing a β-hydroxy ketone. A catalytically effective amount of a catalytic antibody having aldol addition activity or of a catalytically active molecule containing an antibody combining site portion of the catalytic antibody is admixed with sufficient amounts of the aldol donor substrate and aldol acceptor substrate in a reaction medium for producing a reaction admixture. The aldol donor substrate is of a type which includes a reactive carbonyl group and an unbranched carbon adjacent to the carbonyl group. The catalytic antibody or the catalytically active molecule is of a type which includes a lysine residue which forms a Schiff's base intermediate with the reactive carbonyl group of the aldol donor substrate. The above reaction admixture is then maintained for a period of time sufficient for the catalytic antibody or catalytically active molecule to catalyze the aldol condensation between the aldol donor substrate and the aldol acceptor substrate for producing the β-hydroxy ketone. The aldol donor substrate is either a ketone donor substrate or an aldehyde donor substrate. The aldol acceptor substrate is either a ketone acceptor substrate or an aldehyde acceptor substrate. However, the following proviso applies: if the aldol donor substrate is the ketone donor substrate and the aldol acceptor substrate is the aldehyde acceptor substrate, then the ketone donor substrate is not an unfunctionalized open chain aliphatic ketone. In a preferred mode of this aspect of the invention, the aldol acceptor substrate is an aldehyde acceptor substrate and the aldol donor substrate is an ketone donor substrate selected from the group consisting of aliphatic cyclic ketones, functionalized open chain aliphatic ketones, and functionalized cyclic ketones. The aldol condensation may be intermolecular or intramolecular. If it is intramolecular, both the aldol donor substrate and the aldol acceptor substrate form a single reactant molecule and the aldol condensation causes a cylization of the single reactant molecule for forming, a cyclic β-hydroxy ketone. The substrates may be heterogeneous, i.e., the donor and acceptor differ from one another, or homogeneous, i.e., the donor and acceptor are identically the same and are a single ketone reactant molecule.

Optionally, an addition step may be added to the above method wherein the above reaction admixture is maintained for a further period of time in the presence of the catalytic antibody or the catalytically active molecule for converting the β-hydroxy ketone to a β-unsaturated ketone product by an elimination reaction.

Alternatively, a different additional step may be added to the above method wherein the β-hydroxy ketone is converted to a dihydroxy product by reduction.

In an alternative mode of the invention, the aldol donor substrate is represented by the following structure:

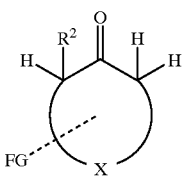

The aldol acceptor substrate is represented by the following structure:

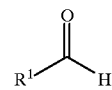

The β-hydroxy ketone is represented by the following structure:

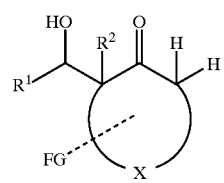

In the above structures, $R^1$ is a radical selected from the group consisting of (FG)-alkyl, (FG)-alkenyl, and (FG)-aryl; $R^2$ is a radical selected from the group consisting of H, OH, and F; X is a radical selected from the group consisting of $NCH_3$, O, S, $CH_2$, and $C_6H_4$; and FG is a radical selected from the group consisting of OH and $OCH_3$.

Another aspect of the invention is directed to another method for catalyzing an aldol condensation between an aldol donor substrate and an aldol acceptor substrate for producing a β-hydroxy ketone. The aldol donor substrate is either a ketone donor substrate or an aldehyde donor substrate. The aldol acceptor substrate is either a ketone acceptor substrate or an aldehyde acceptor substrate. A catalytically effective amount of a catalytic antibody having aldol addition activity or of a catalytically active molecule containing an antibody combining site portion of the catalytic antibody is then admixed with sufficient amounts of the aldol donor substrate and of the aldol acceptor substrate in a reaction medium for producing a reaction admixture. The catalytic antibody or the catalytically active molecule is of a type which includes a lysine residue which forms a Schiff base intermediate with the aldol donor substrate. The aldol donor substrate is unbranched at a non-bond-forming α position. The above reaction admixture is then maintained for a period of time sufficient for the catalytic antibody or the catalytically active molecule to catalyze the aldol condensation between the aldol donor substrate and the aldol acceptor substrate for producing the β-hydroxy ketone and for converting the β-hydroxy ketone to a β-unsaturated ketone product by an elimination reaction.

Another aspect of the invention is directed to a method for catalyzing a retroaldol reaction for converting a β-hydroxy ketone into a first and a second carbonyl product. The first and second carbonyl products are independently either a ketone product or an aldehyde product. A catalytically effective amount of a catalytic antibody having aldol addition activity or of a catalytically active molecule containing an antibody combining site portion of the catalytic antibody is admixed with the β-hydroxy ketone in a reaction medium for producing a reaction admixture. The catalytic antibody or the catalytically active molecule is of a type which includes a lysine residue which forms a Schiff base intermediate with the first carbonyl product. The first carbonyl product is unbranched at an α position. The above reaction admixture is then maintained for a period of time sufficient for the catalytic antibody or the catalytically active molecule to catalyze the retroaldol reaction for converting the β-hydroxy ketone to the first and second carbonyl products. In one mode of this aspect of the invention, the first and second carbonyl products may each be ketone products. In another mode of this invention, the first and second carbonyl products are each aldehyde products. And, in a further mode of this invention, the first carbonyl product is the aldehyde product and the second carbonyl product is the ketone product. The β-hydroxy ketone may be either open chained or cyclic. If the β-hydroxy ketone is cyclic, then the retroaldol reaction opens the cyclic β-hydroxy ketone for forming a single open chain product containing both the first and second carbonyl products as a single product molecule. In another mode of this aspect of the invention, the retroaldol reaction is a reverse self-aldol condensation wherein the first and second carbonyl products are identical to one another. In a preferred mode of this aspect of the invention, the β-hydroxy ketone is represented by the following structure:

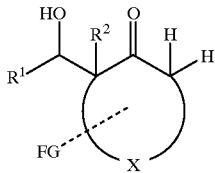

The first carbonyl product is represented by the following structure:

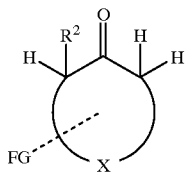

The second carbonyl product is represented by the following structure:

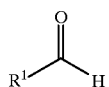

In the above structures, $R^1$ is a radical selected from the group consisting of (FG)-alkyl, (FG)-alkenyl, and (FG)-aryl; $R^2$ is a radical selected from the group consisting of H, OH, and F; X is a radical selected from the group consisting of $NCH_3$, O, S, $CH_2$, and $C_6H_4$; and FG is a radical selected from the group consisting of OH and $OCH_3$.

DESCRIPTION OF FIGURES

FIG. 12 illustrates antibody or amine catalyzed retro-aldol reaction of substrate 59.

FIG. 13 illustrates donor promiscuity: Specific rates [mmol product·$d^{-1}$·$mmol^{-1}$ ab] for antibody catalyzed cross aldol reactions of a variety of ketones with aldehyde 4 under the following defined conditions: 1 M of donor, 500 mM of 4 and 0.4 mol-% of antibody (2 mM). R=4-acetamidophenyl.

FIG. 14 illustrates donor substrates of aldolase antibodies 38C2 and 33F12.

FIG. 15 illustrates acceptor promiscuity: Specific rates [mmol product·$d^{-1}$·$mmol^{-1}$ ab] for antibody catalyzed cross aldol reactions of acetone, cyclopentanone and hydroxyacetone with aldehydes 3 and 5–8 under the following defined conditions: 1 M of donor, 500 mM of 4 and 0.4 mol-% of antibody (2 mM). R=4-acetamidophenyl, R'=4-nitrophenyl.

FIG. 16 illustrates specific rates [mmol product·$d^{-1}$·$mmol^{-1}$ ab] for antibody catalyzed self-aldol reactions of propionaldehyde, acetone, cyclopentanone and for the elimination of water from 36 to 35 under the following defined conditions: 0.1 M of ketone or aldehyde and 0.005 mol-% of antibody (5 mM). These reactions take place predominantly in the absence of an aldehyde acceptor for cross-aldol reactions.

FIG. 17 illustrates kinetic parameters (Michaelis-Menten kinetics) for intramolecular aldol condensations of substrates 39, 43 and 45.

FIG. 18 illustrates specific rates [mmol product·$d^{-1}$·$mmol^{-1}$ ab] for antibody catalyzed cross-aldol reactions of cyclopentanone and hydroxyketones with aliphatic aldehydes under the following defined conditions: 1 M of donor, 500 mM of aldehyde and 0.4 mol-% of antibody (2 mm).

FIG. 19 illustrates stereochemical purity of some products as determined by chiral phase HPLC and GC.

FIG. 20 illustrates comparison of antibody 38C2 catalyzed retro-aldolization of 59 with amine catalyzed retroaldolization in aqueous and organic solvents.

| PROTEIN EVOLUTION | IMMUNE RESPONSE |
|---|---|
| Exon Shuffling Recombination | VDJ rearrangement |
| Gene duplication | Batteries of V, D and J gene elements |
| Accumulation of point mutations | Somatic hypermutation, gene conversion |
| Natural Selection for organismal fitness | Clonal selection for binding |
| Timescale: 102–109 years | Timescale: week |

Figure 22:
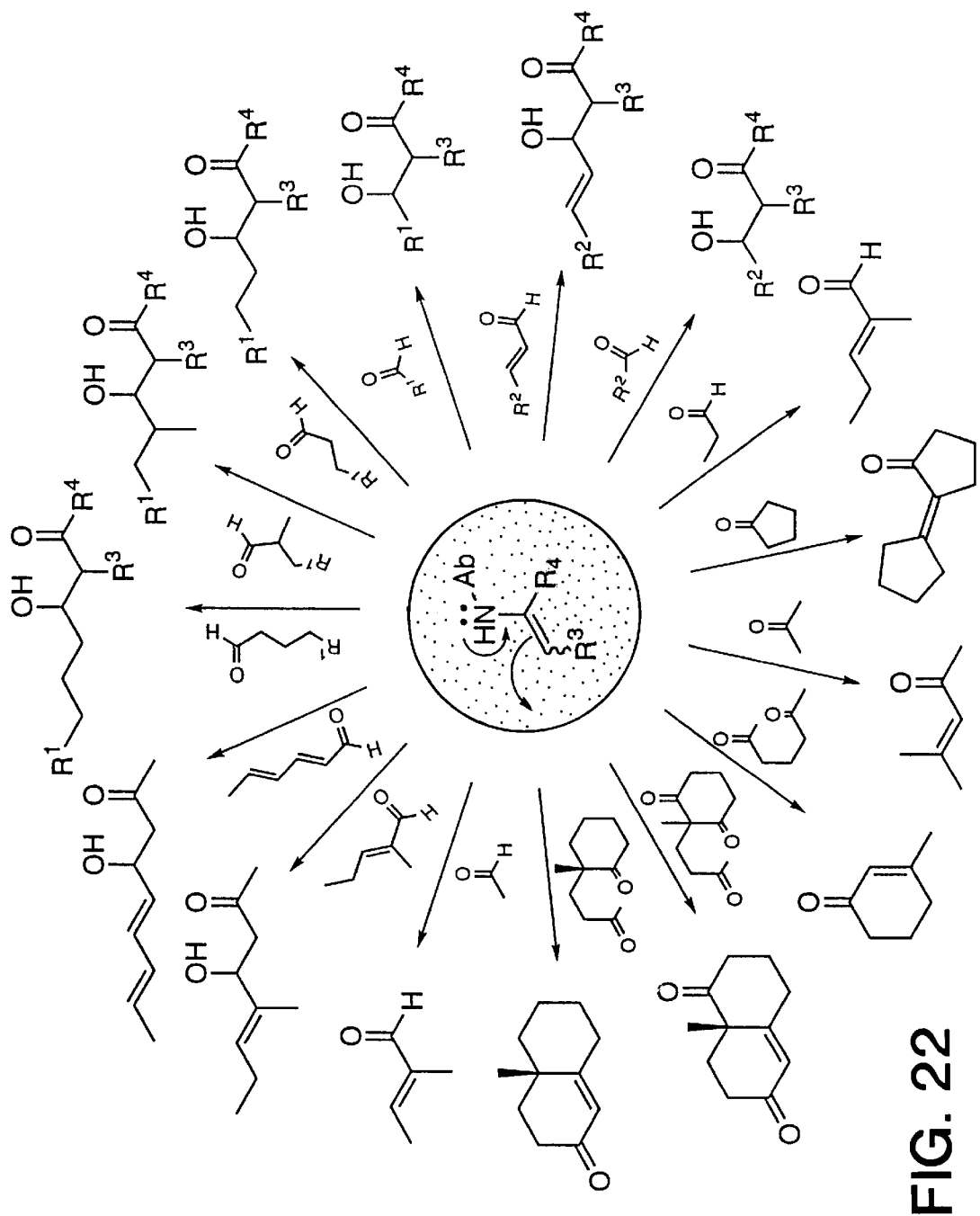

FIG. 22 illustrates different ketones or aldehydes used as substrates, and more than 100 aldehyde-aldehyde, aldehyde-ketone, and ketone-ketone aldol addition or condensation reactions have been catalyzed. $R_1$=4-acetamidobenzyl, $R_2$=4-nitrobenzyl, and $R_3$ and $R_4$ depend on the donor.

Figure 23:
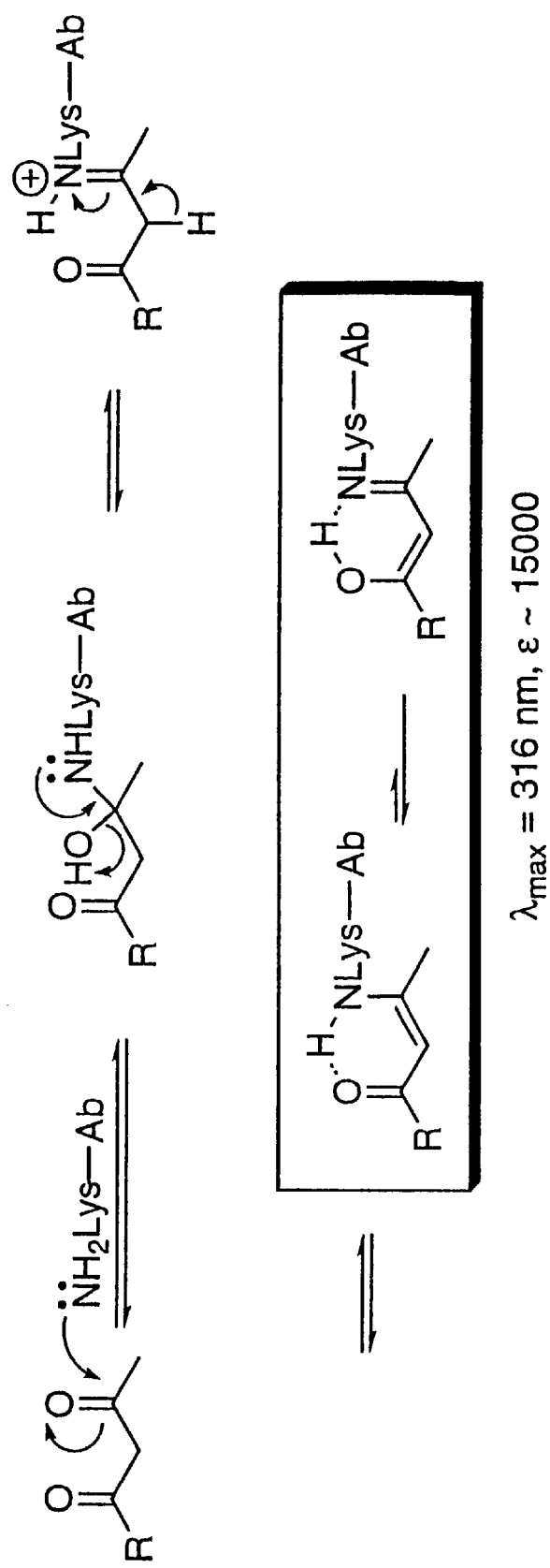

FIG. 23 illustrates a stable covalent interaction with the antibody is formed when the Schiff base tautomerizes to an enamine that, because of a second carbonyl functionality in the α-position, is a stable vinylogous amide.

Figure 24:
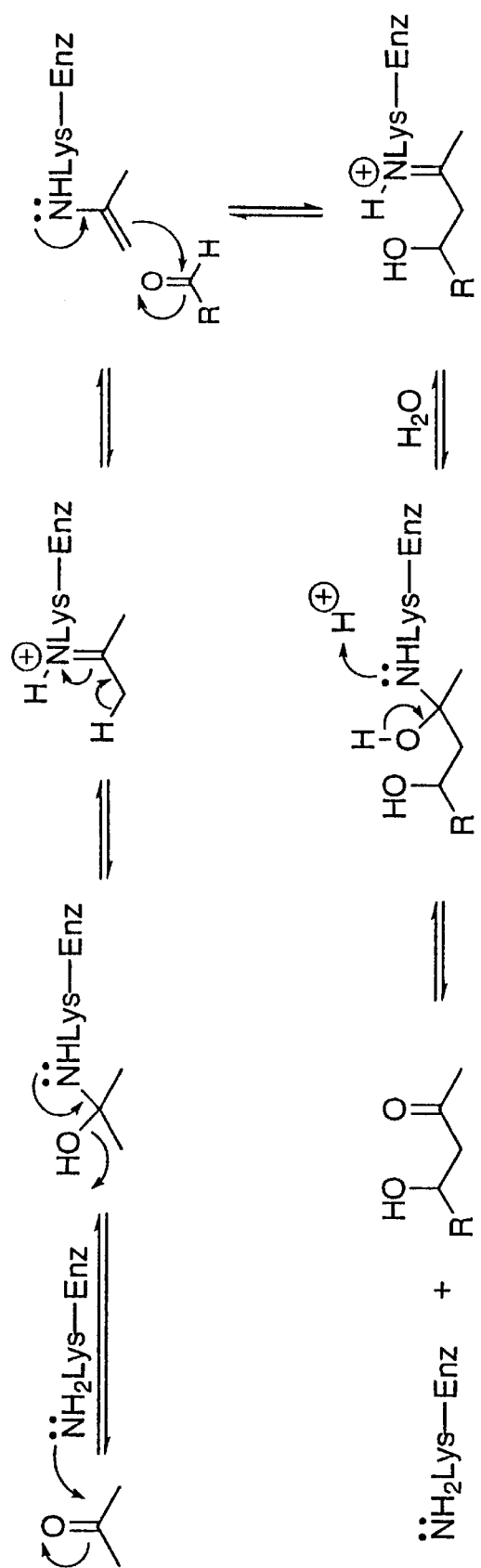

FIG. 24 illustrates that class I aldolase enzymes proceed by the enamine mechanism. The mechanistic symmetry about the C—C bond forming step allows the β-diketone selection to direct mechanistically identical reaction coordinates around this step.

FIG. 25 illustrates the comparison of the optimal reactions catalyzed by FDP aldolase class I and the antibody aldolases. R=4-isobutyramidobenzyl or n-butyl.

FIG. 26 illustrates a variety of reactions wherein the antibody avoids the need for the charged phosphate handles on the natural substrate. The catalytic turnover achieved by the antibodies is within 10 times that of the natural enzyme in this case. Further, the turnover efficiency is maintained for a variety of reactions as shown. Kinetic parameters for a selection of antibody catalyzed aldol and retro-aldol reactions, reflecting the ability of the biocatalyst to accept substrates that clearly differ with respect to their geometry.

Figure 27:
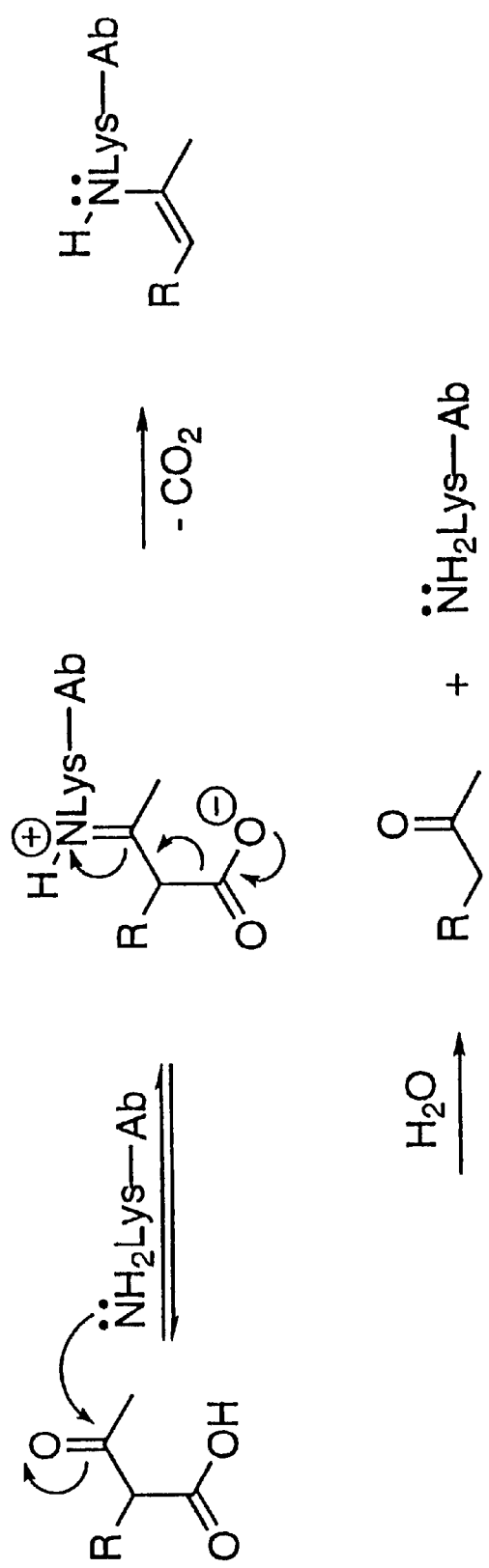

FIG. 27 illustrates that in addition t o the aldol reaction, the antibody catalyzes the decarboxylation β-keto acids with a protonated Schiff serving as the electron sink. Indeed, a few natural aldolases have been shown to catalyze biologically relevant decarboxylation reactions in a mechanistically analogous fashion.

Figure 28:
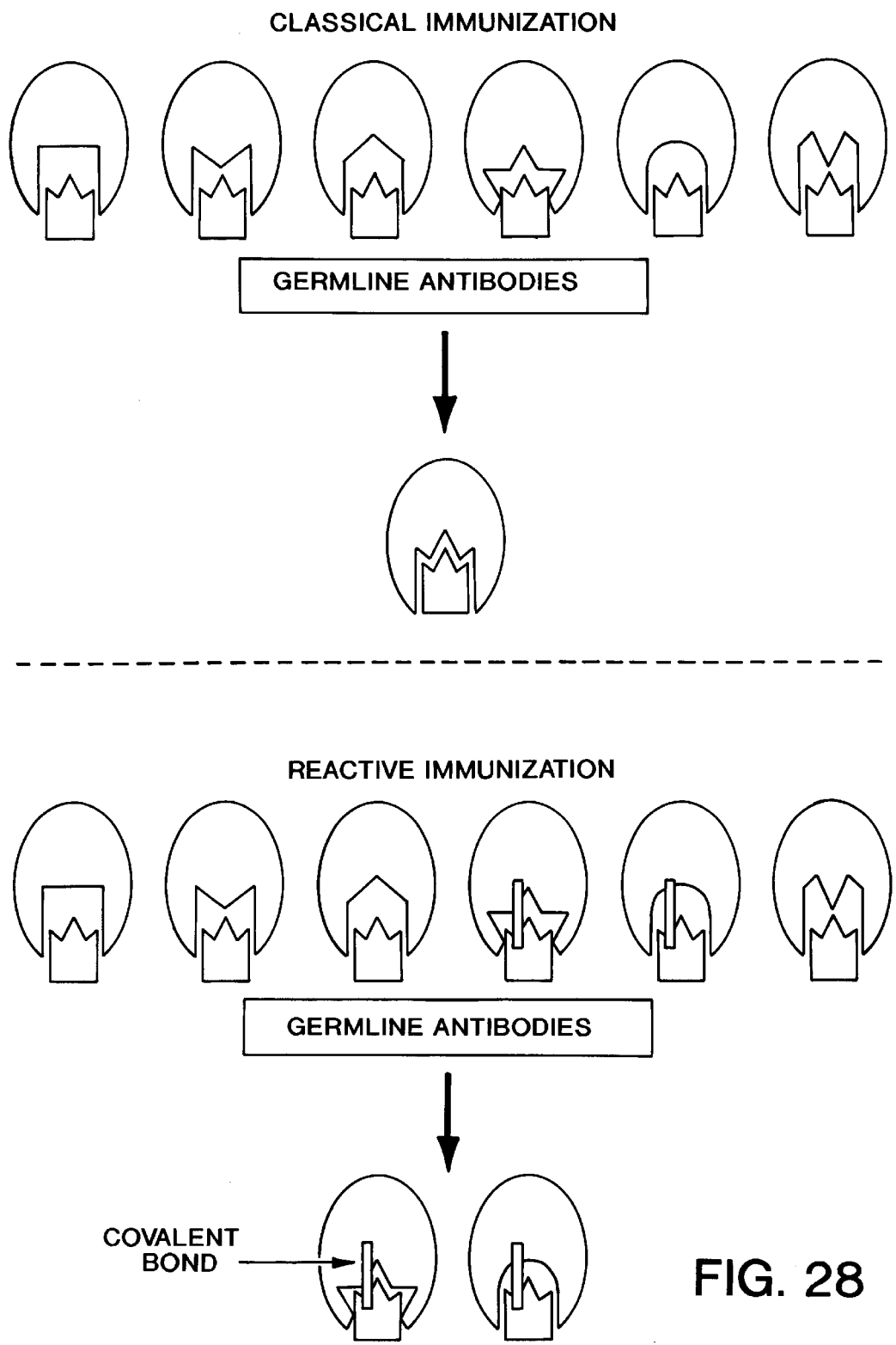

FIG. 28 illustrates comparison of the structural consequences of classical immunization with reactive immunization.

Figure 29:
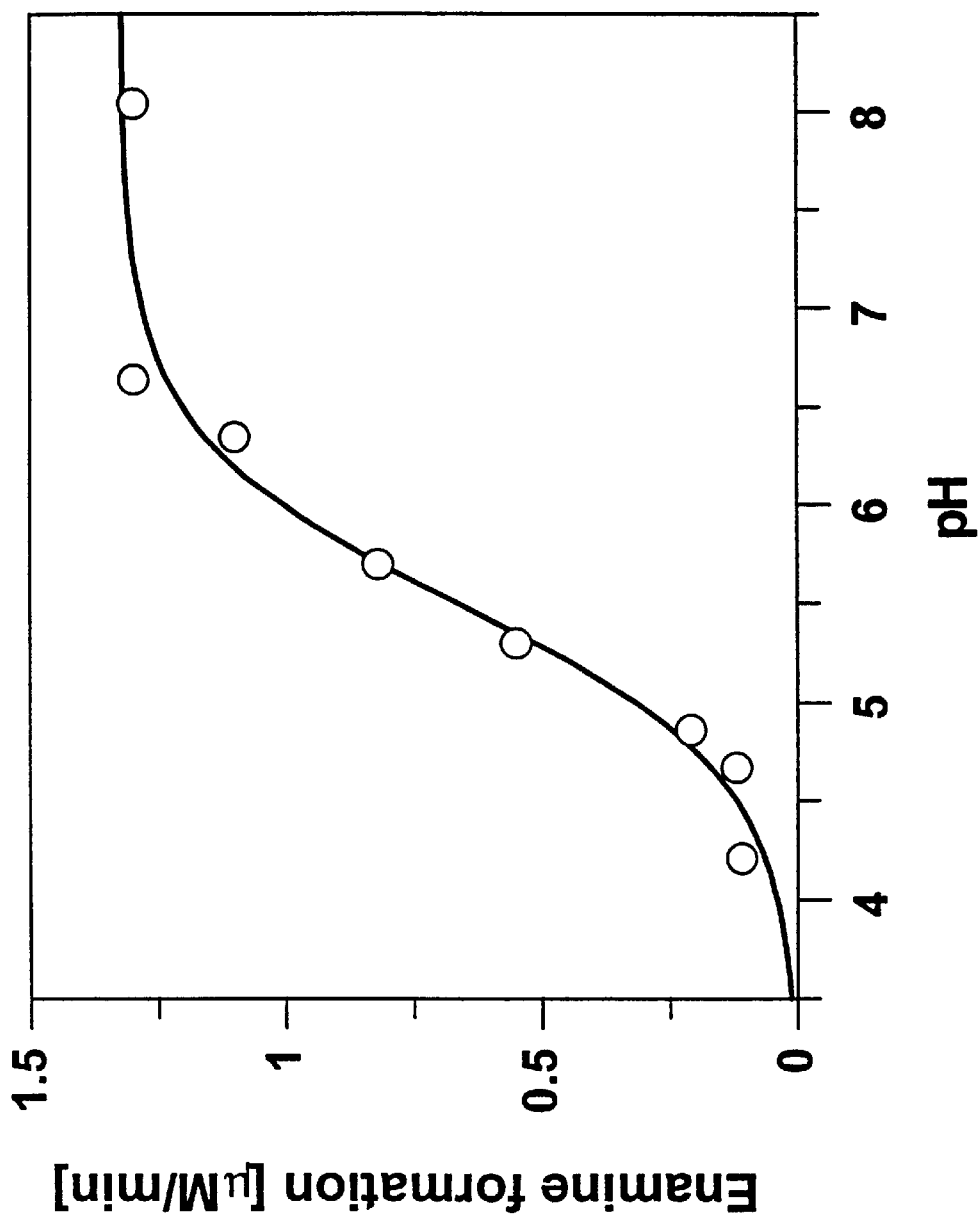

FIG. 29 illustrates rate of enamine formation as a function of pH. Enamine formation between antibody 33F12 and 3-methyl-2,4-pentanedione was followed spectrophotometrically at 335 nm, at 15° C. The incubation mixtures contained 7.5 µM antibody and 250 µM 3-methyl-2,4 pentanedione in citrate/phosphate buffer in the pH range from 4.2 to 8. The reaction velocities were calculated with the use of the experimentally determined extinction coefficient $\epsilon_{335}$= 9.1 $mM^{-1}cm^{-1}$.

Figure 30:
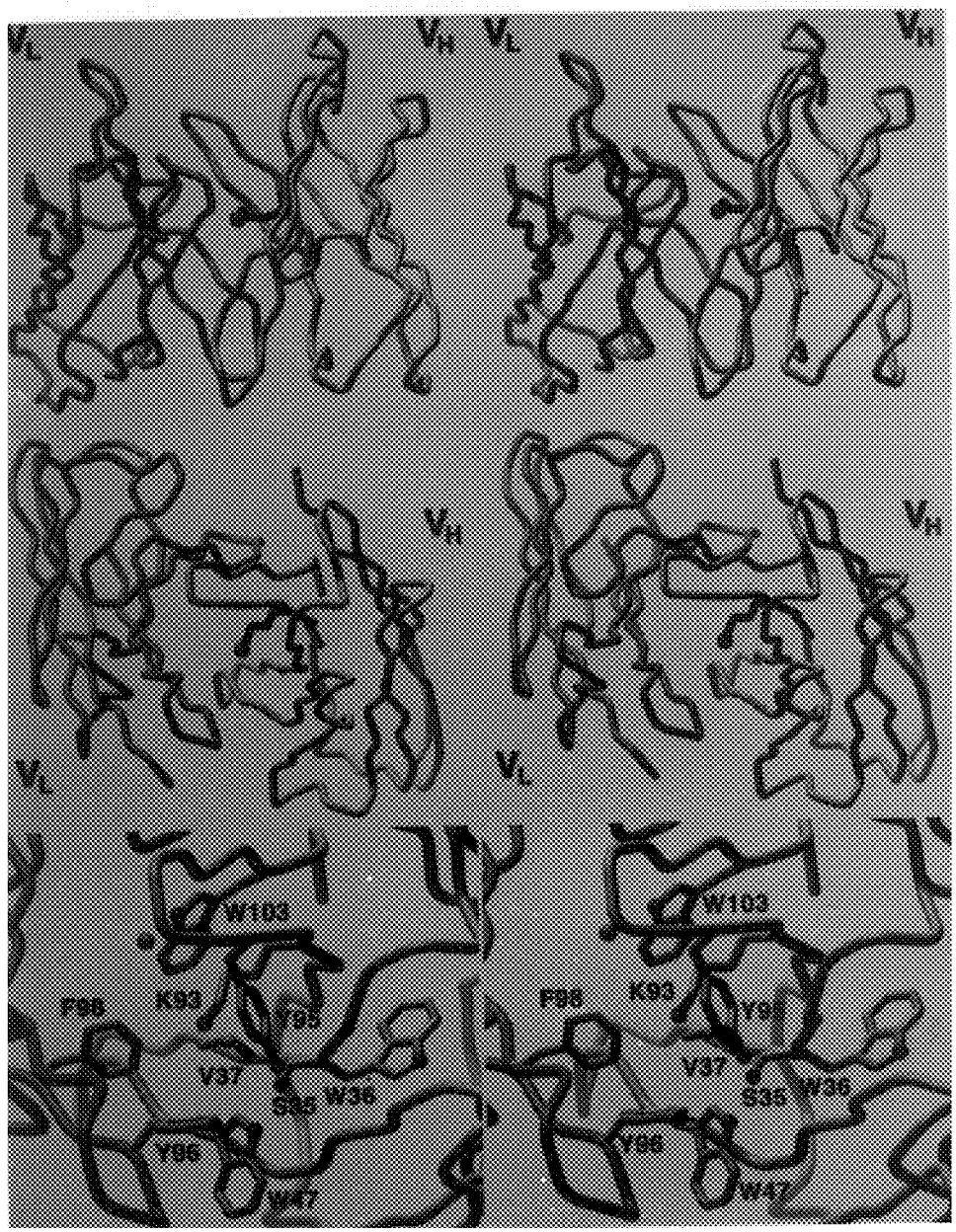

FIG. 30 illustrates the stereoview of the variable region of antibody 33F12. (a) The side view shows the position of LysH93 at the bottom of hypervariable loop H3. (b) Rotation by 90– shows the corresponding top view, looking into the binding site. (c) Stereoview of the Fab' 33F12 binding site, showing only side chains for the residues which are 4 Å or less within the vicinity of LysH93. The light chain is colored in lavender and the heavy chain in cyan. Labels in lavender indicate residues of the light chain, labels in cyan of the heavy chain, respectively.

Figure 31:

FIG. 31 illustrates the stereoview of the 33F12 Fab' binding pocket. Shown is a slice through the molecular surface calculated with a 1.4 Å sphere radius. Only the tip of residue LysH93 Nz is in contact with the molecular surface and located almost at the bottom of the antigen combining site. The light chain is shown in lavender, the heavy chain in cyan.

Figure 32A:
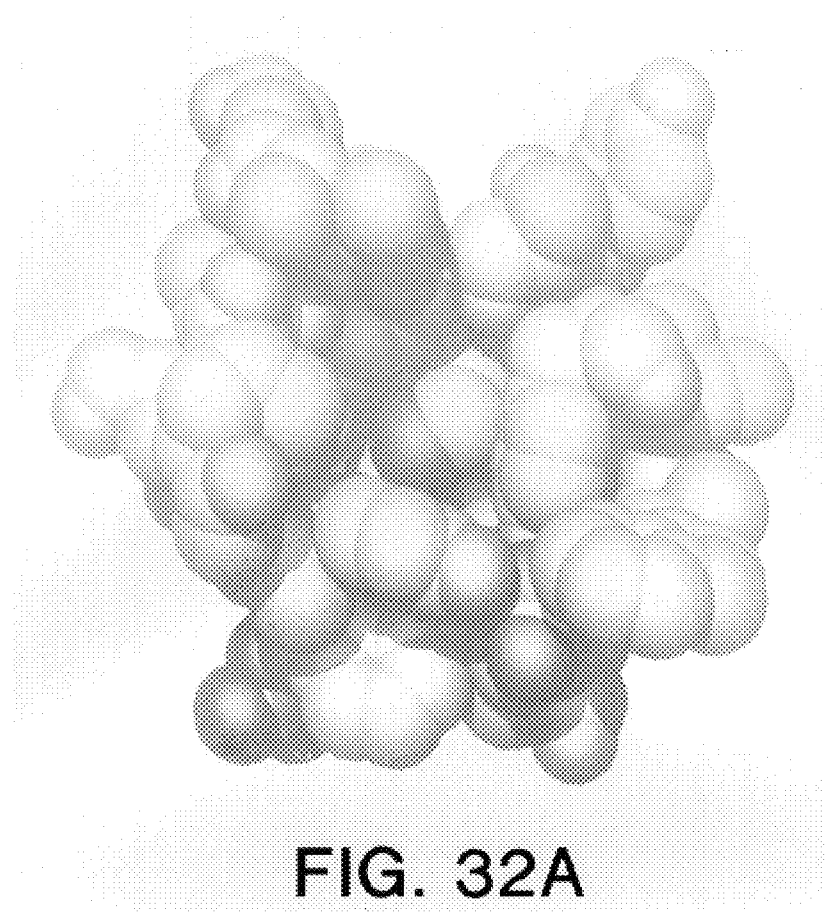

FIG. 32 illustrates the comparison of antibody combining sites, showing the different hydrophobic environment of LysH93 in antibody Fab' 33F12 (A) and antibody Fab 17E8 (27) (pdb code leap) (B). The residues in an 8 Å sphere around the LysH93 Nz are shown. CPK representation showing the hydrophobic atoms in yellow, polar nitrogen and oxygen atoms in cyan and salmon, respectively. Charged basic residues have their nitrogen atoms colored dark-blue and charged oxygen atoms are colored in red. The LysH93 Nz atom is colored in blue.

Figure 33:
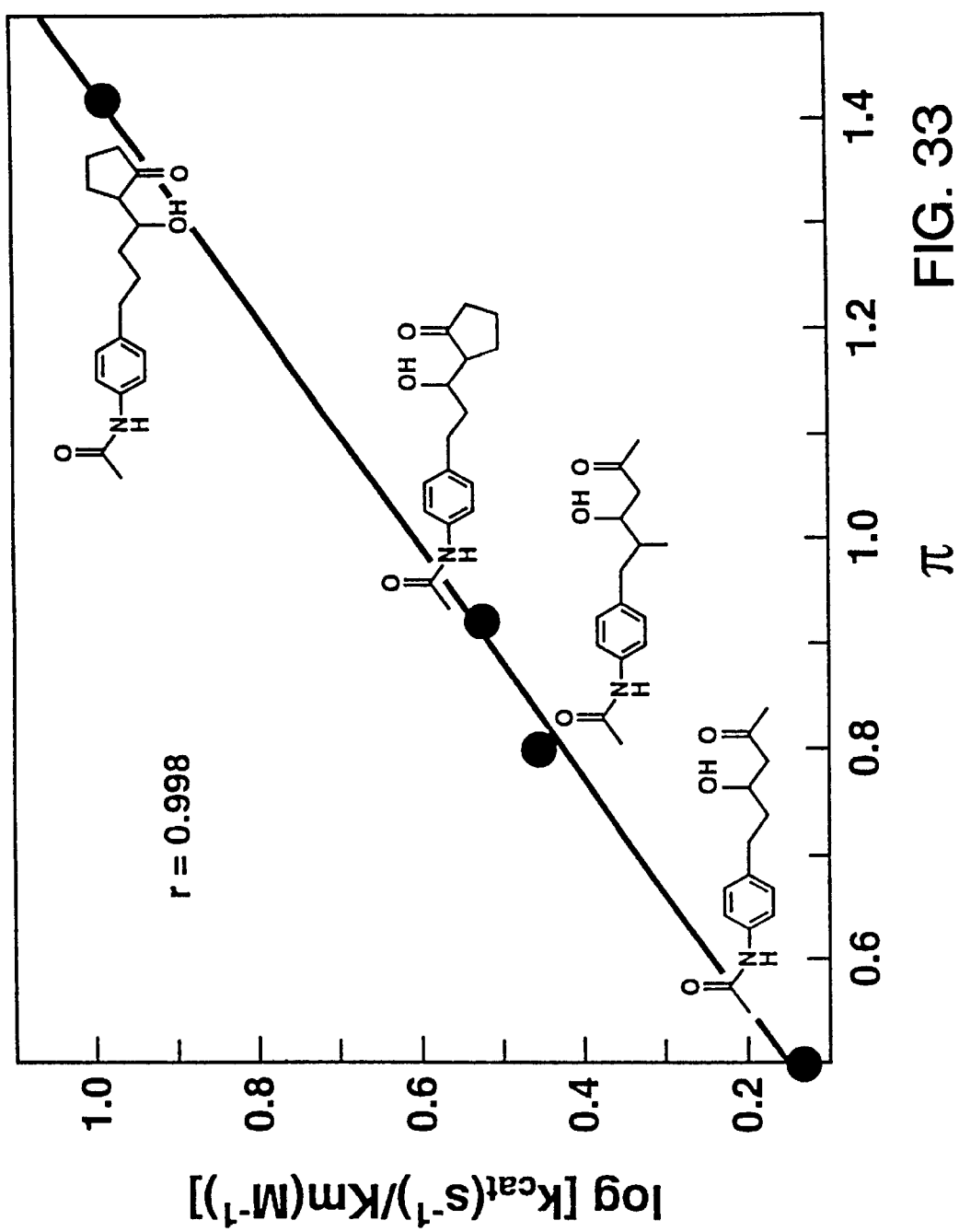

FIG. 33 illustrates the Hansch plot for the determination of the relative hydrophobicity of the active site. The kinetic constants ($k_{cat}/K_m$) for antibody 33F12-catalyzed retro-aldol reaction of a series of aldols, $R^1CH(OH)CHR^2C(O)R^3$, were plotted as a function of the hydrophobicity constant ρ of the corresponding R substituents. The ρ values were calculated as described.

Figure 34:
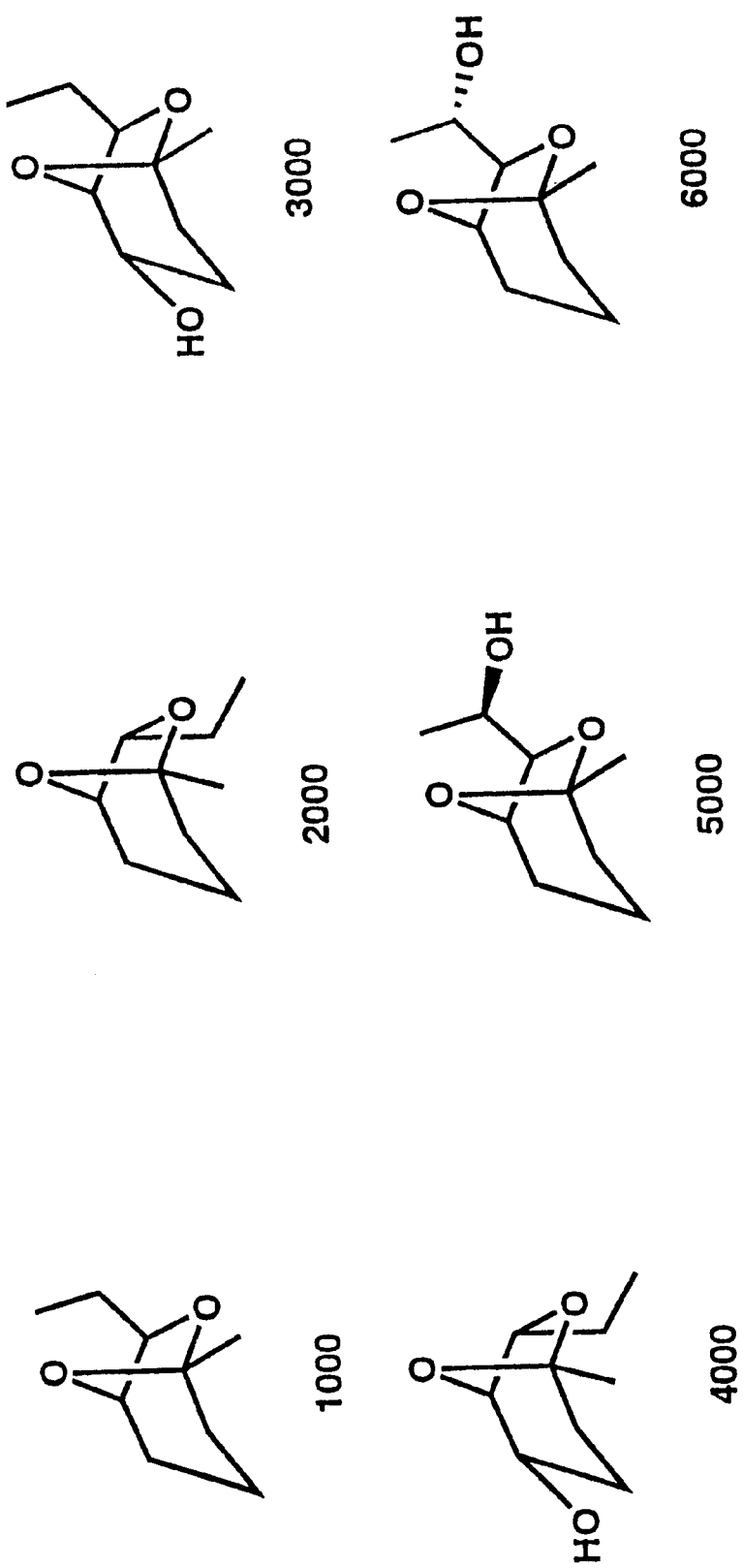

FIG. 34 illustrates structure of some Brevicomins: (+)-Exo-brevicomin (1000); (+)-Endo-Brevicomin (2000); (1R, 2S,5S,7R)-2-Hydroxy-exo-brevicomin (3000); (1R,2S,5S, 7S)-2-Hydroxy-endo-brevicomin (4000); (1R,1'R,5'R,7'R)-1-Hydroxy-exo-brevicomin (5000); (1S,1'R,5'R,7'R)-1-Hydroxy-exo-brevicomin (6000).

Figure 35:
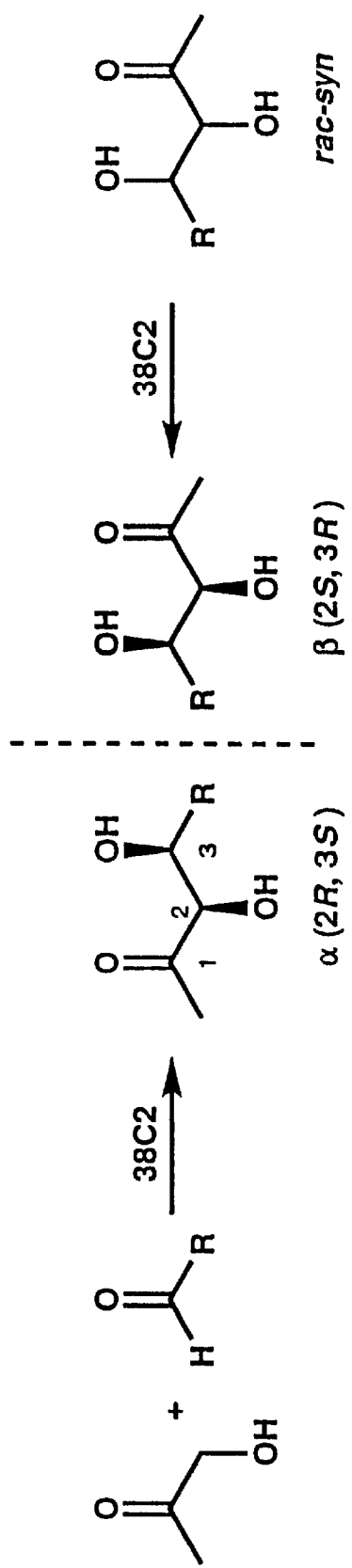

FIG. 35 illustrates the sterochemical course of 38C2 catalyzed aldol and retroaldol reactions involving hydroxyacetone.

Figure 36:
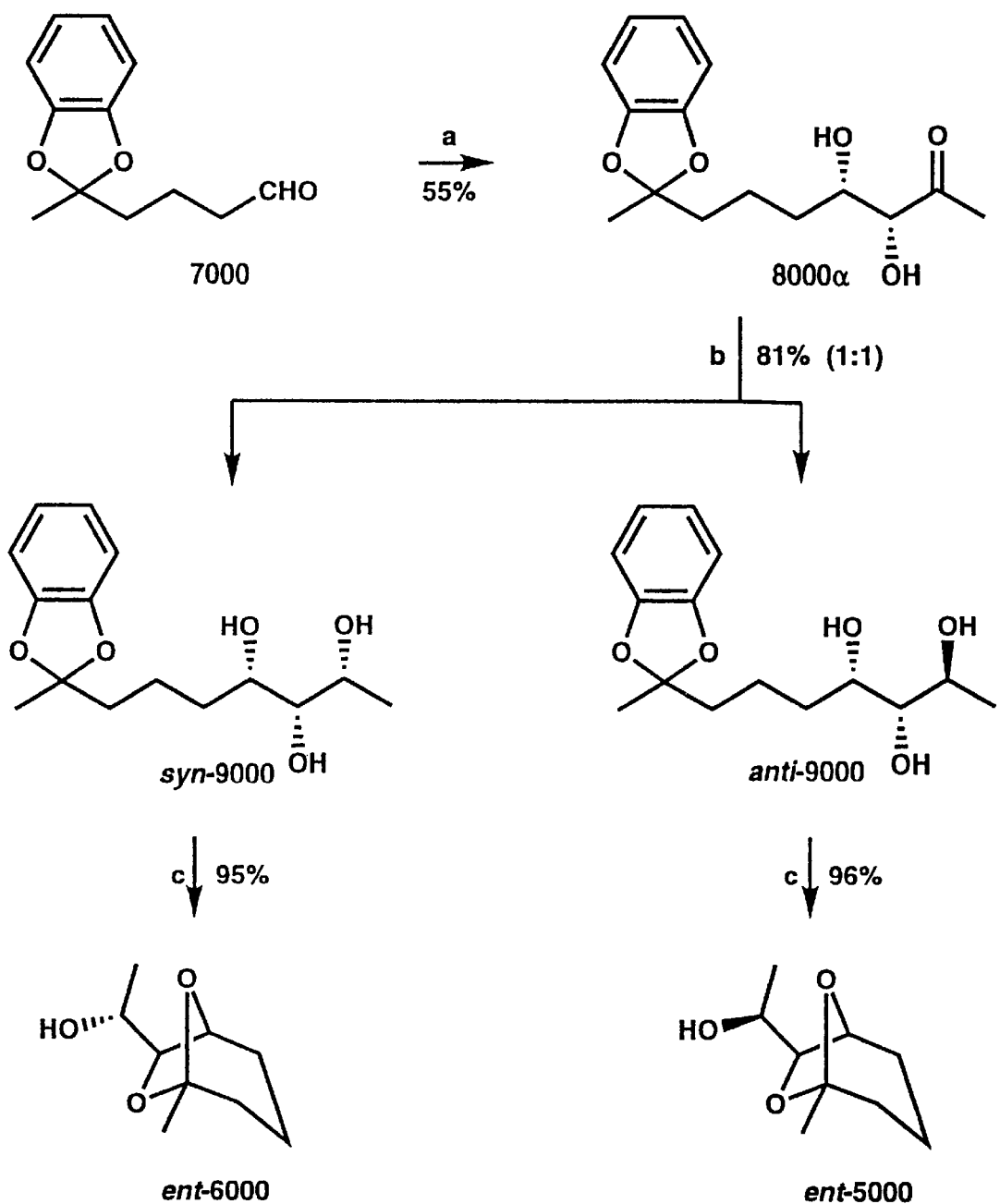

FIG. 36 illustrates the processes to make 5000, and 6000 from syn-9000 and anti-9000 with the following conditions: a) Antibody 38C2 (0.66 mol %), hydroxyacetone (5 vol %), phosphate buffered saline (PBS, pH 7.4) b) $NaBH_4$, MeOH; HPLC separation; c) pTsOH, $C_6H_6$, 60° C.

Figure 37:
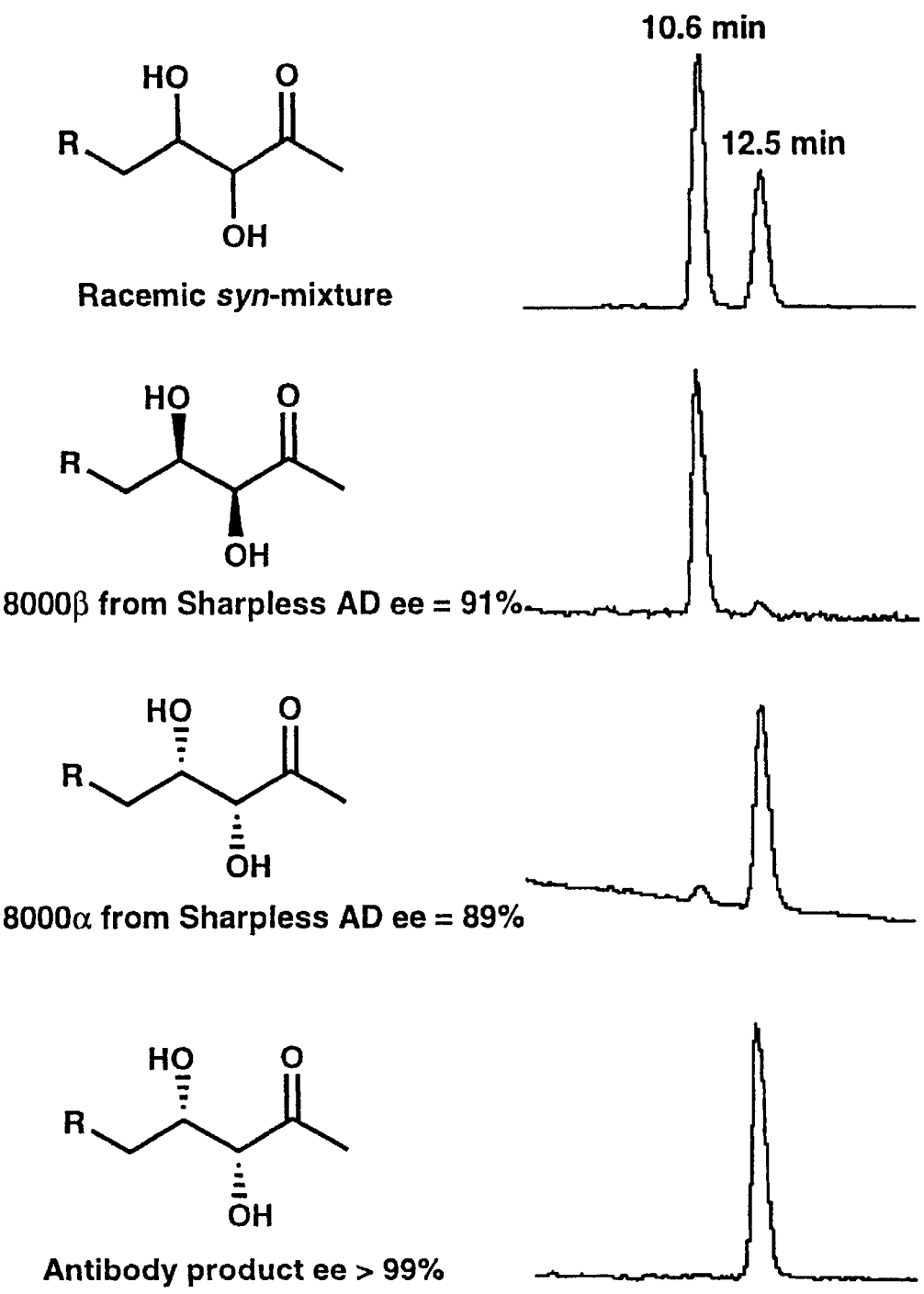

FIG. 37 illustrates determination of the absolute configuration and enantiomeric purity of aldol 8000α from an analytical scale reaction. Chiracell AD column (12% i-PrOH/hexane, 1 ml/min, wavelength (λ)=284 nm).

Figure 38:
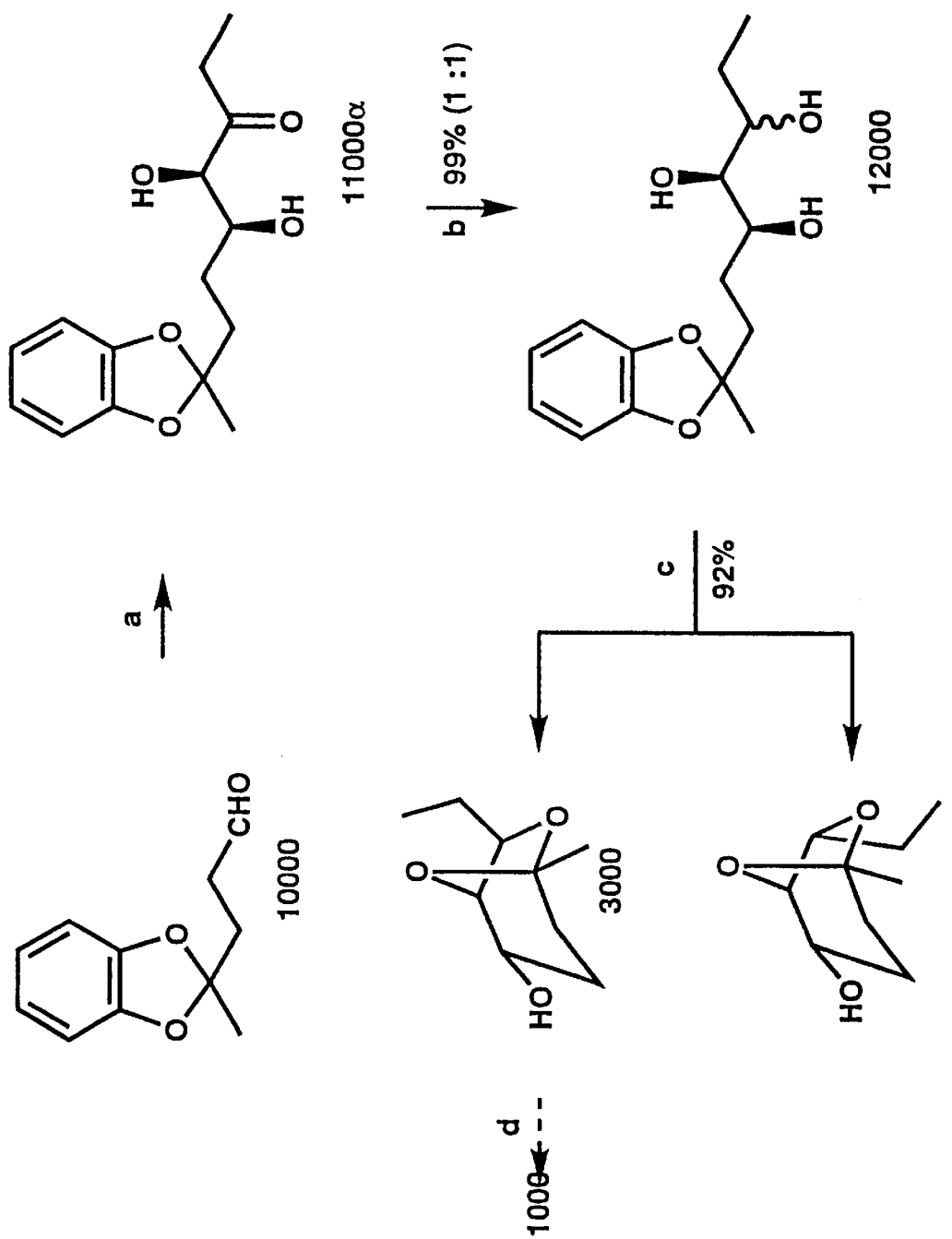

FIG. 38 illustrates the synthesis of 1000 from 10000 with the following conditions: a) Analytical scale reaction: antibody 38C2 (0.6 mol %), 1-hydroxy-2-butanone (5 vol %), PBS (pH 7.4) b) NaBH$_4$, MeOH c) pTsOH, C$_6$H$_6$, 60° C., column chromatography d) following conditions exactly as described in Taniguchi, H. Ohnishi, K. Ogasawara, *Chem. Commun.* 1996, 1477–1478.

FIG. 39 shows a table which indicates kinetic parameters of antibody catalyzed reactions. [a] No product formation was observed in the background reactions after three days. [b] k$_{cat}$ obtained from Lineweaver-Burk plots. [c] Rates were measured at a single concentration and are relative to the rates found for compounds 8000α and 8000β.

Figure 40:
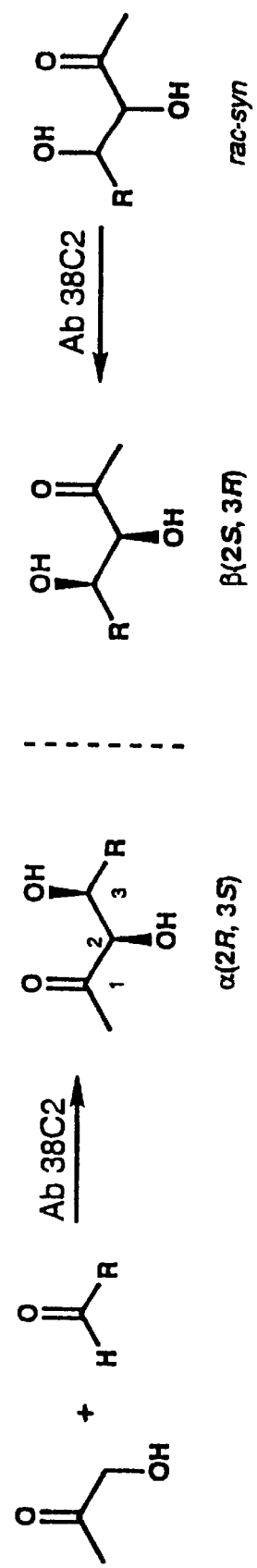

FIG. 40 illustrates that hydroxyacetone reacts with different aldehydes, highly regio-, diastereo-, and enantioselectively, to give the corresponding α-(2R,3S)-dihydroxy ketones. The corresponding β-(2S,3R)-isomer can be obtained from the racemic mixture via 38C2 catalyzed enantioselective retro-aldol reaction). This strategy has been successfully demonstrated with the kinetic resolution of many aldols and in the total synthesis of ten different brevicomins.

FIG. 41 illustrates Ketone 2111a was easily transformed to 1-deoxy-L-xylulose (1111) by hydrogenation. Benzyloxyacetaldehyde (80 mg, 0.53 mmol) in ) in ) 0.5 mL of acetonitrile, was added to 9 mL of a solution of antibody 38C2 (35 mg, 0.23 mmol) in PBS (phosphate buffer saline, 100 mM), followed by the addition of of hydroxyacetone. (0.5 mL, 6.3 mmol). After 48 hr at room temperature the reaction reached 56% conversion and the mixture was freeze dried. The remaining residue was extracted with methylene chloride. The solvent was removed under reduced pressure and the crude product was purified by column chromatography (silica gel, ethyl acetate/hexane, 1/1) to give pure 2111a (39 mg, 0.17 mmol, 32%) in 97% ee. Benzyl ether 2111a (39 mg, 0.17 mmol) was dissolved in 1 mL of methanol and hydrogenated with a catalytic amount of palladium hydroxide on carbon. After two hr, the mixture was filtered through celite and the solvent was removed under reduced pressure to give pure 1-deoxy-L-xylulose (19 mg, 0.14 mmol, 81%).

FIG. 42 illustrates that in order to determine the enantiomeric purity of the aldol product, we synthesized reference compounds. Horner-Wadsworth-Emmons reaction of diethyl-2-oxopropyl-phosphonate with benzyloxyacetaldehyde gave the known olefin 3111 which was dihydroxylated according to the Sharpless procedure to give reference aldols 2111a and 2111b in high ee's.

Figure 43:
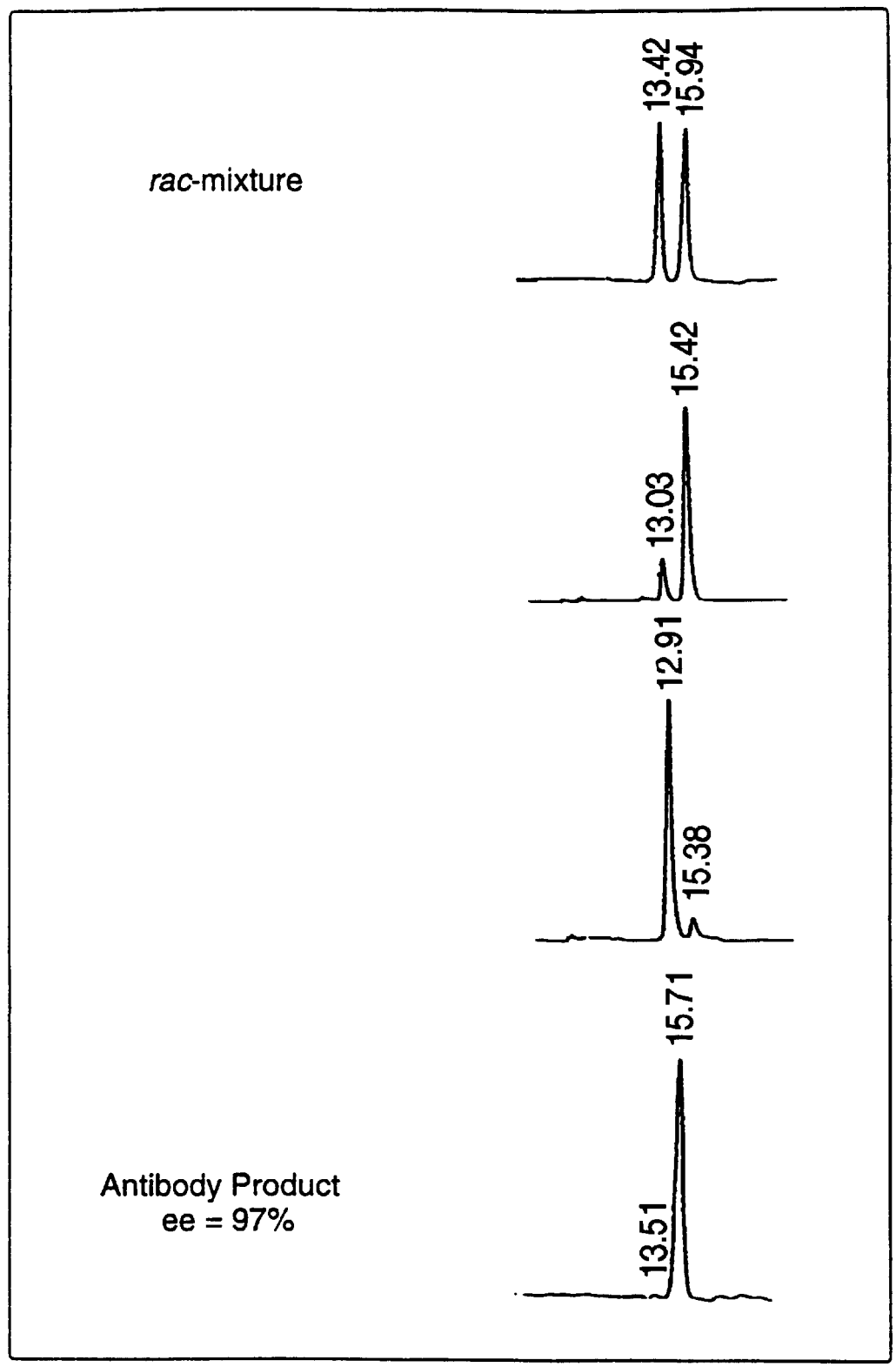

FIG. 43 illustrates the determination of the absolute configuration and enantiomeric purity of aldol 2111α from an antibody catalyzed reaction. Chiracell AD column (12% i-PrOH/hexane, 1 ml/min, λ=254 nm).

Figure 44:
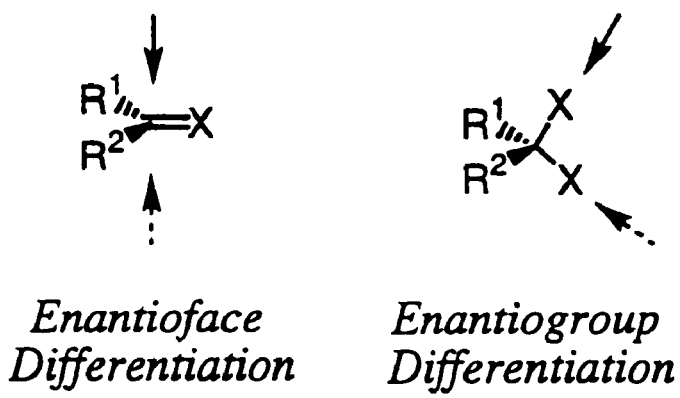

FIG. 44 shows enantioselectivity in reactions where two enantiotopic groups are differentiated.

Figure 45:
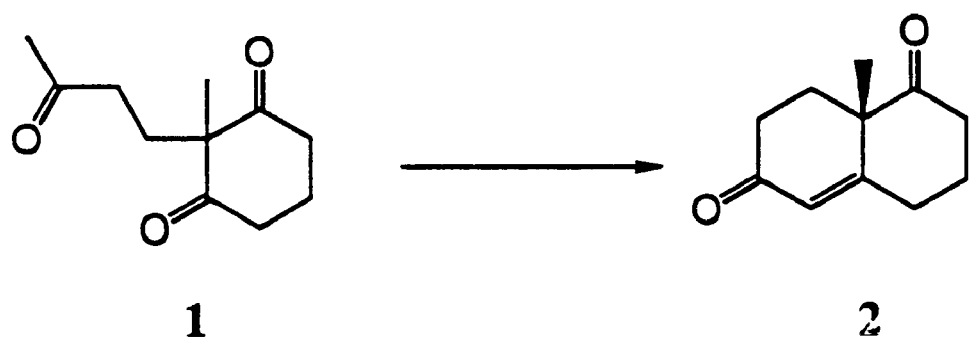

FIG. 45 shows the synthesis of a Wieland-Miescher ketone.

Figure 46:
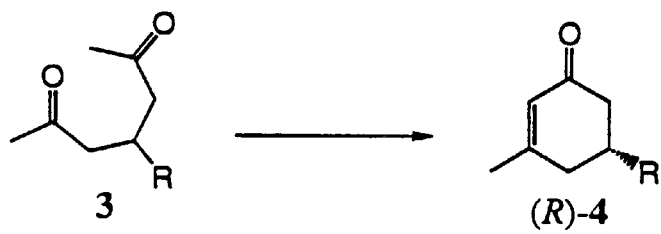

FIG. 46 shows a proline catalyzed enantioselective cyclodehydration.

Figure 47:
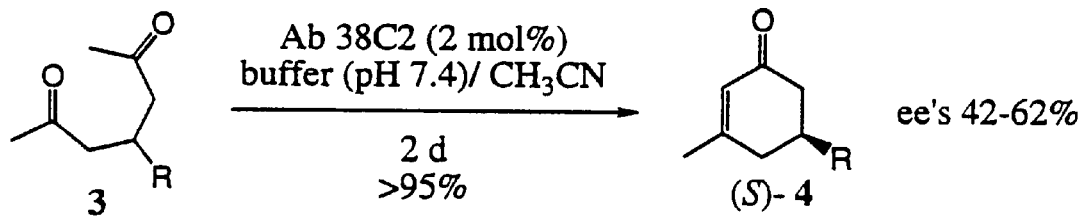

FIG. 47 shows a catalyzed reaction of this invention.

Figure 48:
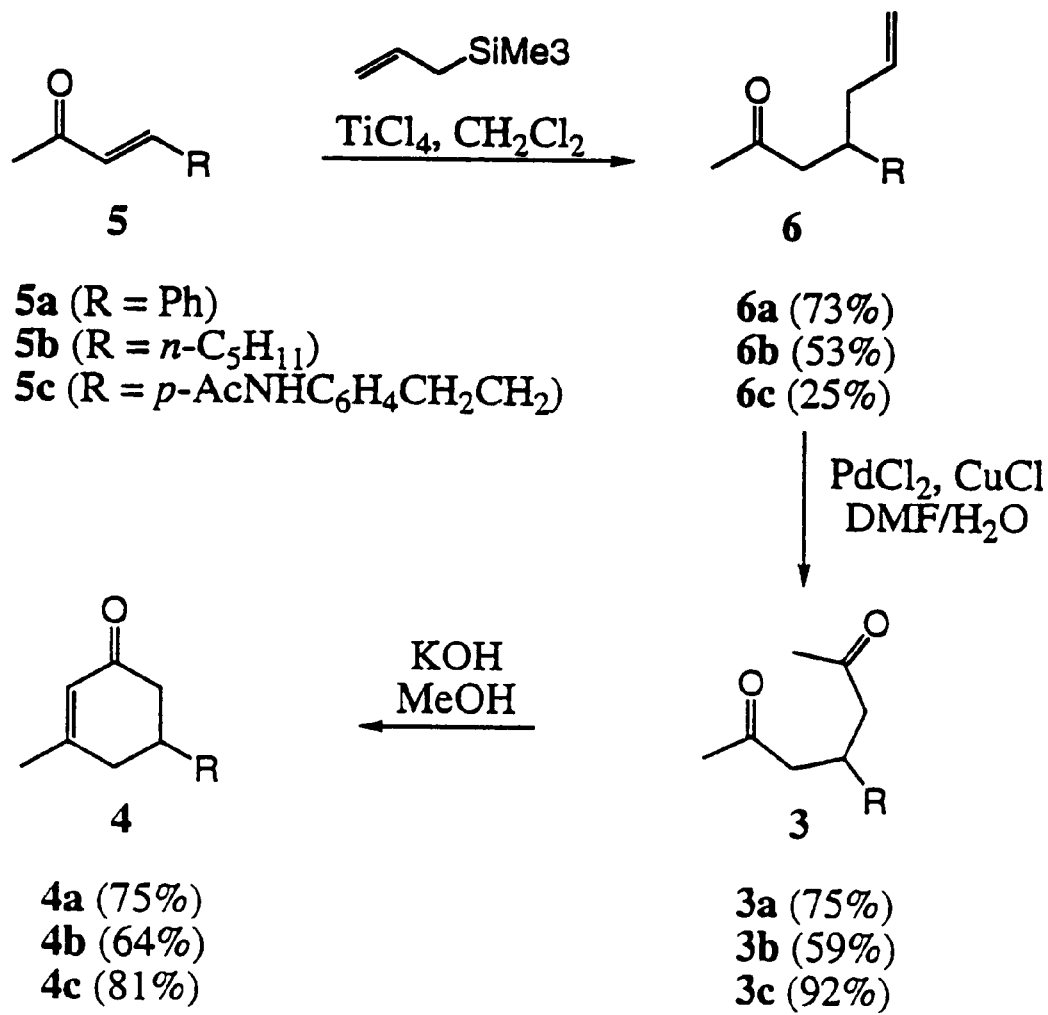

FIG. 48 shows a synthetic scheme involving base treatment of ketones.

Figure 49:
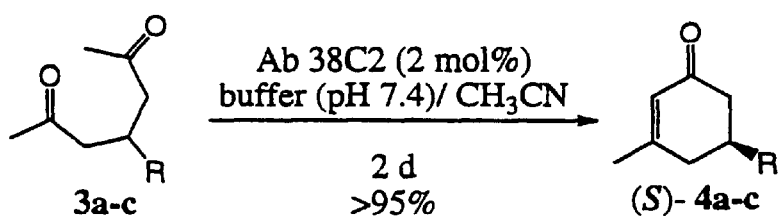

FIG. 49 shows antibody catalyzed cyclization of ketones.

Figure 50:
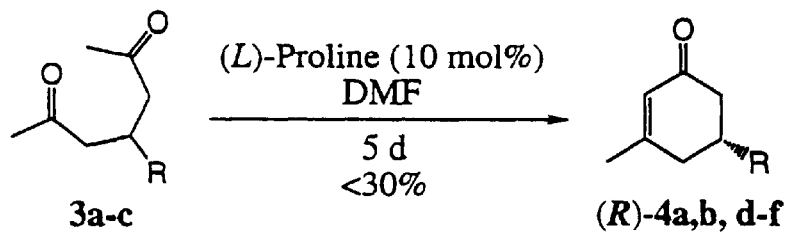

FIG. 50 shows a synthetic scheme for preparation of isomeric enones.

DETAILED DESCRIPTION OF THE INVENTION

The invention is directed to the substrate specificity, synthetic scope, and efficiency of aldolase catalytic antibodies 38C2 and 33F12. These antibodies use the enamine mechanism common to the natural Class I aldolase enzymes. Substrates for these catalysts, 23 donors and 16 acceptors, have been identified. The aldol acceptor specificity is expected to be much broader than that defined here since all aldehydes tested, with the exception polyhydroxylated aldehydes, were substrates for the antibodies. 38C2 and 33F12 have been shown to catalyze intermolecular ketone-ketone, ketone-aldehyde, aldehyde-ketone, and aldehyde-aldehyde aldol addition reactions and in some cases to catalyze their subsequent dehydration to yield aldol condensation products. Substrates for intramolecular aldol reactions have also been defined. With acetone as the aldol donor substrate a new stereogenic center is formed by attack on the si-face of the aldehyde with ee's in most cases exceeding 95%. With hydroxyacetone as the donor substrate, attack occurs on the re-face generating an α,β-dihydroxyketone with two stereogenic centers of the α-syn configuration in 70 to >98% ee. With fluoroacetone donor reactions, the major product is a syn α-fluoro-β-hydroxyketone with 95% ee. Studies of retro-aldol reactions demonstrate that the antibodies provide up to 108-fold enhanced efficiency relative to simple amine catalyzed reactions.

EXAMPLE 1

Aldolase Antibodies of Remarkable Scope

With antibodies 38C2 and 33F12 we have addressed four issues: i) scope and limitations of substrates for intermolecular crossed and self-aldols as well as intramolecular aldols, ii) their stereoselectivity, iii) kinetic parameters for these reactions to understand the nature of the binding pocket and iv) additional mechanistic studies to gain further insight into these catalysts.

Cross-Aldol Reactions

Figure 1:
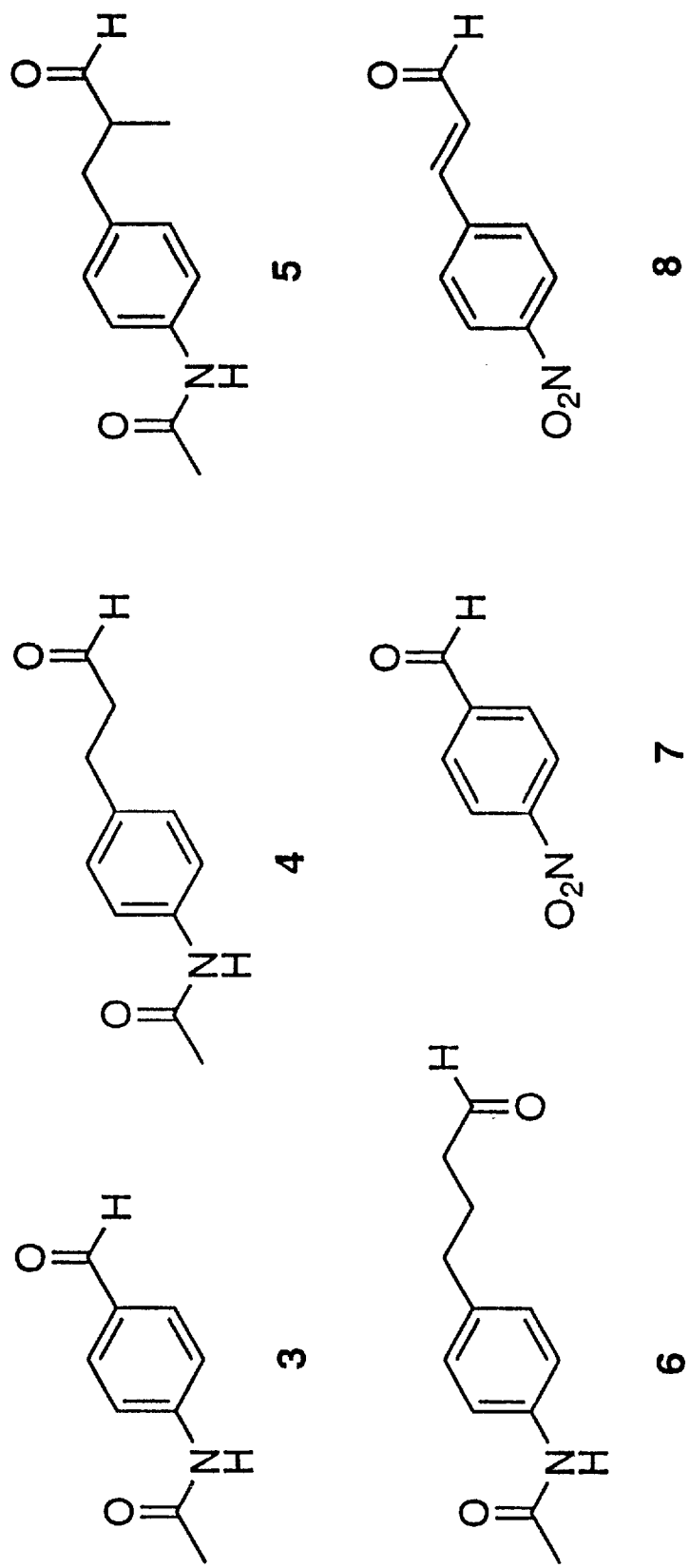
FIG. 1 illustrates aldehydes 3–8 as acceptors in the antibody catalyzed cross-aldol reactions.

To define the scope of antibody catalysts 38C2 and 33F12 for the cross-aldol reaction we tested a wide variety of commercially available ketones as donors and a set of six different aldehydes (4-acetamidobenzaldehyde 3, 3-(4'-acetamidophenyl-)propanal 4, 3-(4'-acetamidophenyl)-2-methylpropanal 5, 4-(4'-acetamidophenyl)butanal 6, 4-nitrobenzaldehyde 7, and 4-nitrocinnamaldehyde 8; FIG. 1) as acceptors. To screen for donor activity, aldehyde 4 was chosen as the standard acceptor aldehyde since it bears a 4-acetamidophenyl group at C3. This portion of the molecule is closely related to the hapten structure 1 and may be specifically recognized by the antibodies.

For ease of comparison we determined specific rates for these reactions under the following defined conditions: 1 M of donor, 500 mM of aldehyde 4 and 0.4 mol-% of antibody . As can be seen from FIG. 13, a wide variety of different ketones undergo the aldol reaction with aldehyde 4 as proven by comparison of the retention times of the products using high performance liquid chromatography (HPLC) with independently chemically synthesized standards: aliphatic open chain (acetone, butanone, 2-pentanone and 3-pentanone), aliphatic cyclic (cyclopentanone and cyclohexanone), functionalized open chain (hydroxyacetone and fluoroacetone) and functionalized cyclic (2-hydroxy cyclohexanone) ketones. A large variety of other ketones were also studied with aldehyde 4 with monitoring of the consumption of 4 and appearance of a new peak tentatively assigned as the β-hydroxyketone product. Substrate ketones from all studies are summarized in FIG. 14. The antibody catalyzed aldol reactions were inhibited by addition of equimolar amounts of the hapten 1 or 2,4-pentanedione. Further control experiments were carried out using lysine or bovine serum albumin instead of the antibodies. No catalysis of the aldol reactions studied here was observed in these cases. A number of ketones, e.g. octanone, demonstrated limited solubility in aqueous medium perhaps precluding their availability to the catalysts. Further study of mixed solvent systems may allow conditions to be defined where substrates such as these are accepted by the catalyst. Of the ketones studied, reactions involving hydroxyacetone as the donor were the most efficient.

The astonishingly high promiscuity of ab 38C2 for these physico-chemically very different ketones is in remarkable contrast to the natural aldolases which tolerate minor, if any, change in the structure of the donor (Gijsen, H. J. M.; Qiao, L.; Fitz,W.; Wong, C.-H. *Chem. Rev.* 1996, 96, 443. (b) Wong, C.-H.; Halcomb, R. L.; Ichikawa, Y.; Kajimoto, T. *Angew. Chem. Int. Ed. Engl.* 1995, 34, 412–432. (b)Henderson, I.; Sharpless, K. B.; Wong, C.-H. *J. Am. Chem. Soc.* 1994, 116, 558. (c) Wong, C.-H.; Whitesides, G. M. *Enzymes in Synthetic Organic Chemistry* (Pergamon, Oxford, 1994); Bednarski, M. D., in *Comprehensive Organic Synthesis,* Trost, B. M., Ed (Pergamaon, Oxford, 1991), vol. 2, 455; Gijsen, H. J. M., Wong, C.-H. ibid. 1995, 117, 2947; Wong, C.-H. et al. ibid. 1995, 117, 3333; Chen, L.; Dumas, D. P., Wong, C.-H. ibid. 1992, 114, 741).

Next, we focused on defining the specificity for acceptor aldehydes. We selected acetone, cyclopentanone and hydroxyacetone as representative donors from the variety of ketones listed in FIG. 13 and tested these in the aldol reaction with aldehydes 3 and 5–8 (FIG. 1). Again, identical conditions (as described above) were used for the determination of the corresponding specific rates (FIG. 15). All substrate combinations gave the expected products. Simple aliphatic aldehyde acceptors are described below (see Miscellaneous Aldol Reactions). A variety of polyhydroxylated acceptor aldehydes, glyceraldehyde, glucose, and ribose were also studied. These substrates were not accepted by these antibodies presumably due to the hydrophobic nature of the active site. These studies, together with those described below, suggest an acceptor specificity that is very broad, albeit limited to hydrophobic aldehydes.

To gain more detailed information about the catalytic system we chose some of the described reactions and studied initial rates varying the substrate concentrations of either the donor or the acceptor while keeping the concentrations of the second reactant constant. All reactions with aldehydes 4–8 followed typical Michaelis-Menten kinetics by treating the data according to pseudo-first order kinetics. Generally, no substrate or product inhibition was observed. Using 4-acetamidobenzaldehyde 3 at higher concentrations (2 mM and higher) substrate inhibition was found, presumably because of a reversible Schiff base formation between the active site lysine and the aldehyde. Typical values for the Michaelis constants $K_m$ of the donors range from 1 mM to 1 M, reflecting the ability of the antibody to accept a wide variety of different ketones. Values for $K_m$ of the acceptors 3–8 range from 10 to 500 mM. Obviously, the aromatic portion of these molecules is responsible for an increased recognition by the active site. Characteristic values for $k_{cat}$ range from 10-3 to 1 $min^{-1}$ and show a ratio of $k_{cat}/K_{uncat}$ of 105 to 107 (see below for additional kinetic data). All data is reported per antibody active site where the antibody molecule has two active sites.

Self-Aldol Reactions

During the course of our investigations we also addressed the question whether antibodies 38C2 and 33F12 are capable of catalyzing self-aldol reactions. Self-aldolization was observed with propionaldehyde, acetone, and cyclopentanone but not for compounds 4–6 (FIG. 16). Again, for ease of comparison, specific rates were determined using the following defined conditions: 0.1 M of ketone or aldehyde and 0.005 mol-% of antibody. With these substrates the antibodies catalyzed the aldol condensation reaction which consists of two consecutive steps: the aldol addition and the subsequent elimination of water. Using propionaldehyde as substrate, the aldol addition product, 3-hydroxy-2-methylpentanal, was not detected as an intermediate but exclusively trans-2-methyl-2-pentenal 33 was detected, suggesting that the elimination of water is also catalyzed (vide infra). Compound 33 was obtained as single product and is not a substrate for a consecutive aldol addition reaction with a third propionaldehyde molecule. Interestingly, compound 33 acts as an acceptor if acetone is used as donor (see paragraph Miscellaneous Aldol Reactions). Acetone itself and cyclopentanone undergo the self-aldol condensation to give mesityl oxide 34 and compound 35, respectively, if no aldehyde acceptor for a cross-aldol reaction is present which binds preferentially to the active site. These ketone self-aldol reactions are substantially slower, typically more than 500-fold slower, than the cross-aldol reactions involving these donors described above. In the cross-aldol reactions described above with acetone and cyclopentanone as donors, the acetone-acetone and cyclopentanone-cyclopentanone self-condensation products were not observed. Thus, self-aldolization activity in the cross-aldol reaction does not compromise isolation of the cross-aldol product. To elucidate the general mechanism of the self-aldol condensation reactions described above, we chose cyclopentanone as substrate and monitored the appearance of the aldol addition product 36 and it's elimination product 35 by HPLC and gas chromatography (GC). In addition, ab 38C2 was incubated with independently synthesized intermediate 36 and the appearance of 35 was monitored by HPLC. Indeed, both reaction steps are catalyzed with the aldol addition occurring faster than the elimination step. Kinetic study of the overall transformation of cyclopentanone to 35 revealed $K_m$=845 mM, $k_{cat}$=2×10−4 min−1 The elimination reaction from 36 to 35 also followed Michaelis-Menten kinetics ($K_m$=750 mM, $k_{cat}$=9×10−4 min−1 and $k_{cat}/K_{uncat}$=2240).

Figure 7:
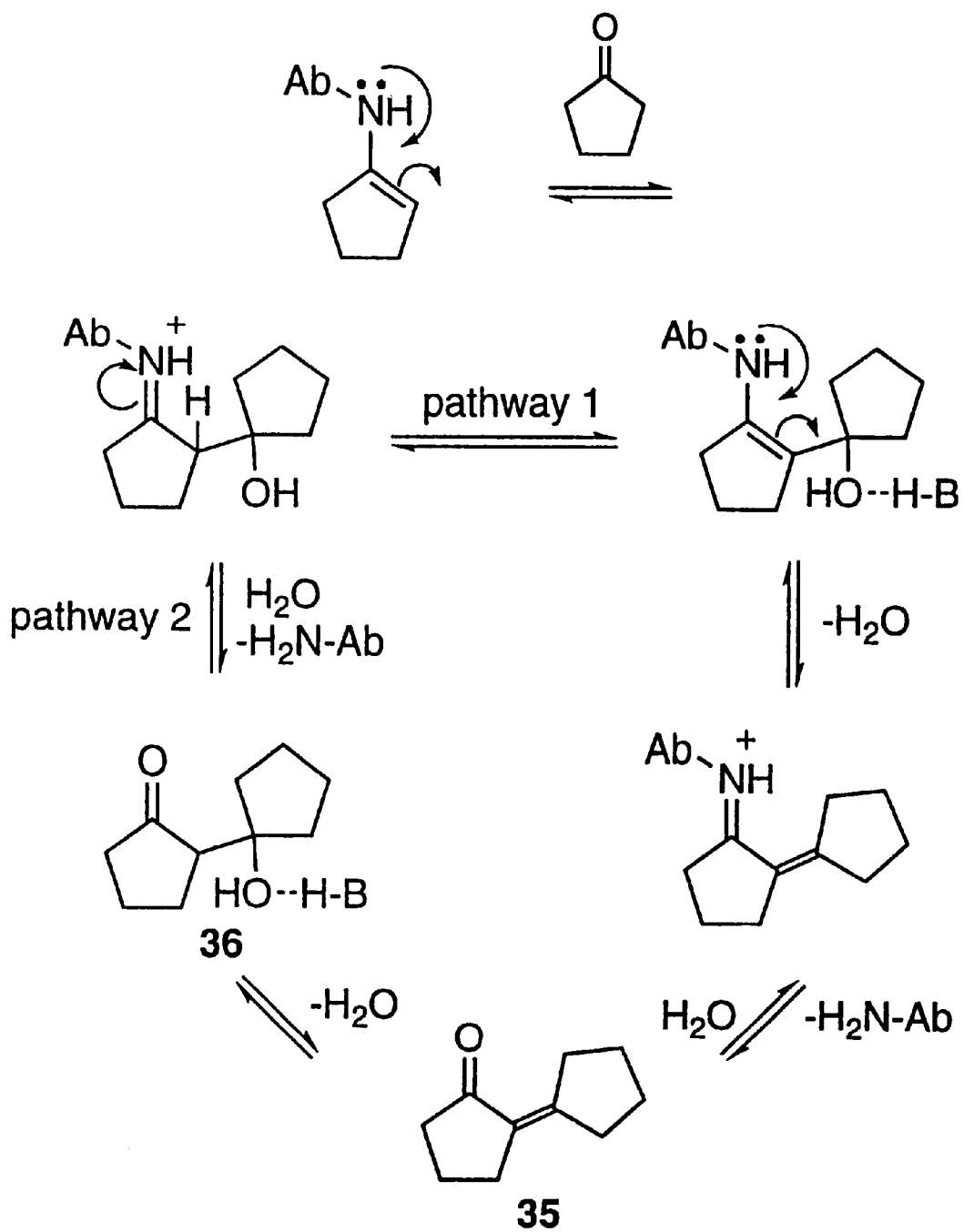
FIG. 7 illustrates the proposed mechanism (pathway 1) for the antibody catalyzed self-aldol condensation of cyclopentanone. Both steps, the addition and the elimination, are catalyzed by the antibodies. The less favored mechanism (pathway 2) in which water elimination occurs via free 36 is also shown.

From these experiments we suggest a mechanism for the self-aldol condensation reaction of cyclopentanone as shown in FIG. 7 (pathway 1). The β-hydroxy iminium cation (formed in the active site after attack of the enamine of cyclopentanone at the carbonyl C-atom of a second molecule cyclopentanone) tautomerizes after loss of a proton into a β-hydroxy enamine which then loses water. This process is assisted by the electron donation from the enamine nitrogen atom (Hupe, D. J.; Kendall, M. C. R.; Spencer, T. A. *J. Am. Chem. Soc.* 1973, 95, 2271). The α,β-unsaturated iminium cation is finally hydrolyzed and the aldol condensation product 35 is released while the lysine residue of ab 38C2 re-enters the catalytic cycle.

An alternate mechanism in which the elimination step occurs in the background via free 36 is also shown in FIG. 7 (pathway 2) but seems less likely, since the elimination was shown to be catalyzed by ab 38C2 and inhibited by acetylacetone. No background reaction for the overall conversion of cyclopentanone to 35 in the absence of antibody could be observed following extended incubation for 2 months.

Intramolecular Aldol Condensations

Figure 8:
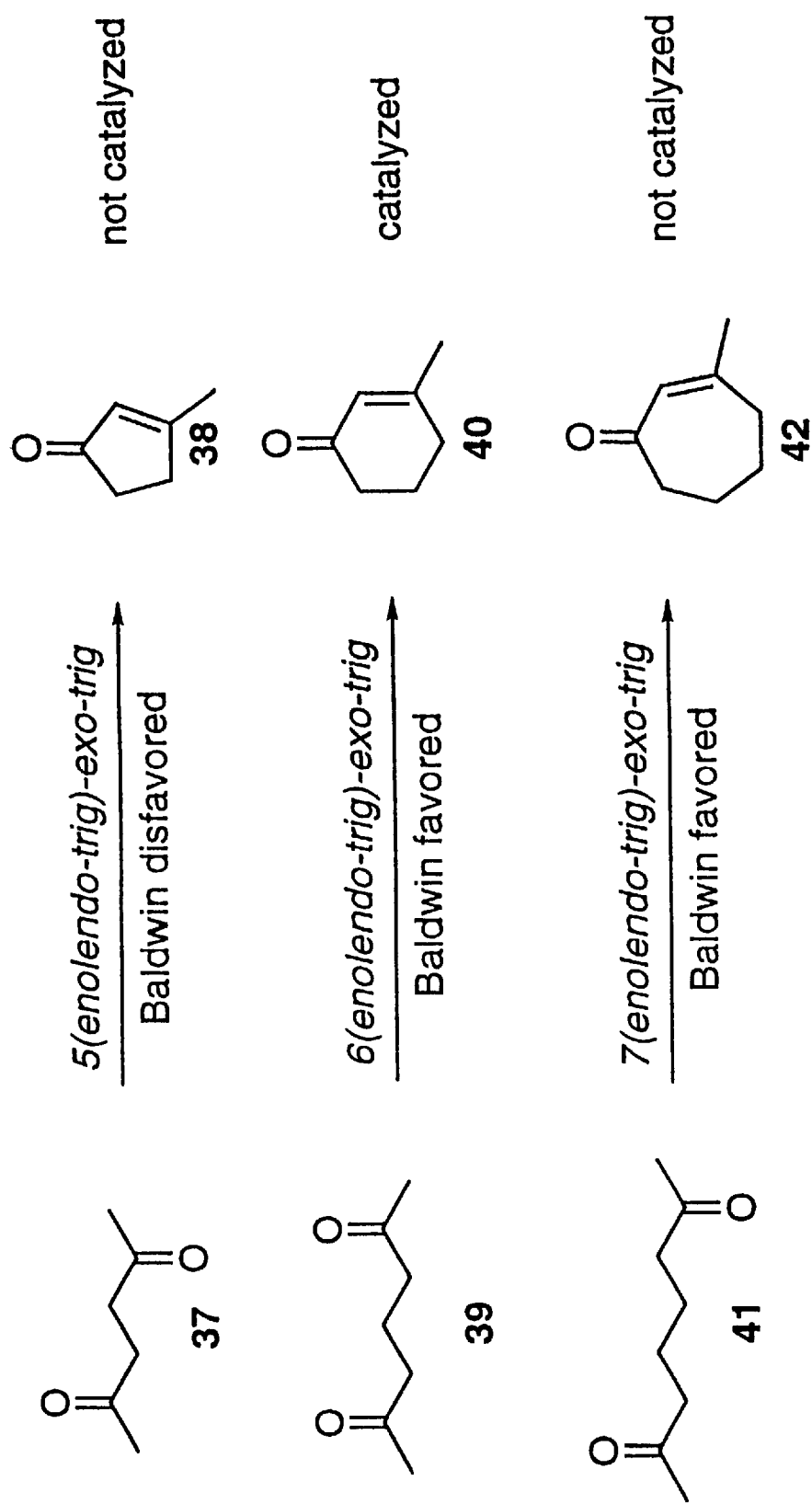
FIG. 8 illustrates diketones 37, 39, and 41 tested as substrates in the antibody catalyzed intramolecular aldol condensation. Only the 6(enol-endo-trig)-exo-trig process, leading to 40 from 39 is catalyzed.

To study intramolecular aldol reactions, 38C2 was incubated with three different aliphatic diketones: 2,4-hexanedione 37, 2,5-heptanedione 39 and 2,6-octanedione 41 (FIG. 8). No catalysis was observed in the reaction pathway from 37 to 3-methylcyclopent-2-enone 38, presumably because of the Baldwin 7 disfavored 5(enolendo-trig)

process involved in the attack of the enamine at C2 in substrate 37. Although the corresponding ring closure (followed by water elimination) of 41 to give 3-methylcyclohept-2-enone 42 is Baldwin favored (a 7(enolendo-trig) process) also in this case no product formation was observed. In contrast, the Baldwin favored ring closure reaction of 2,5-heptanedione 39 (a 6(enolendo-trig) process) followed by elimination of water and giving 3-methylcyclohex-2-enone 40 was catalyzed by ab 38C2.

Figure 9:
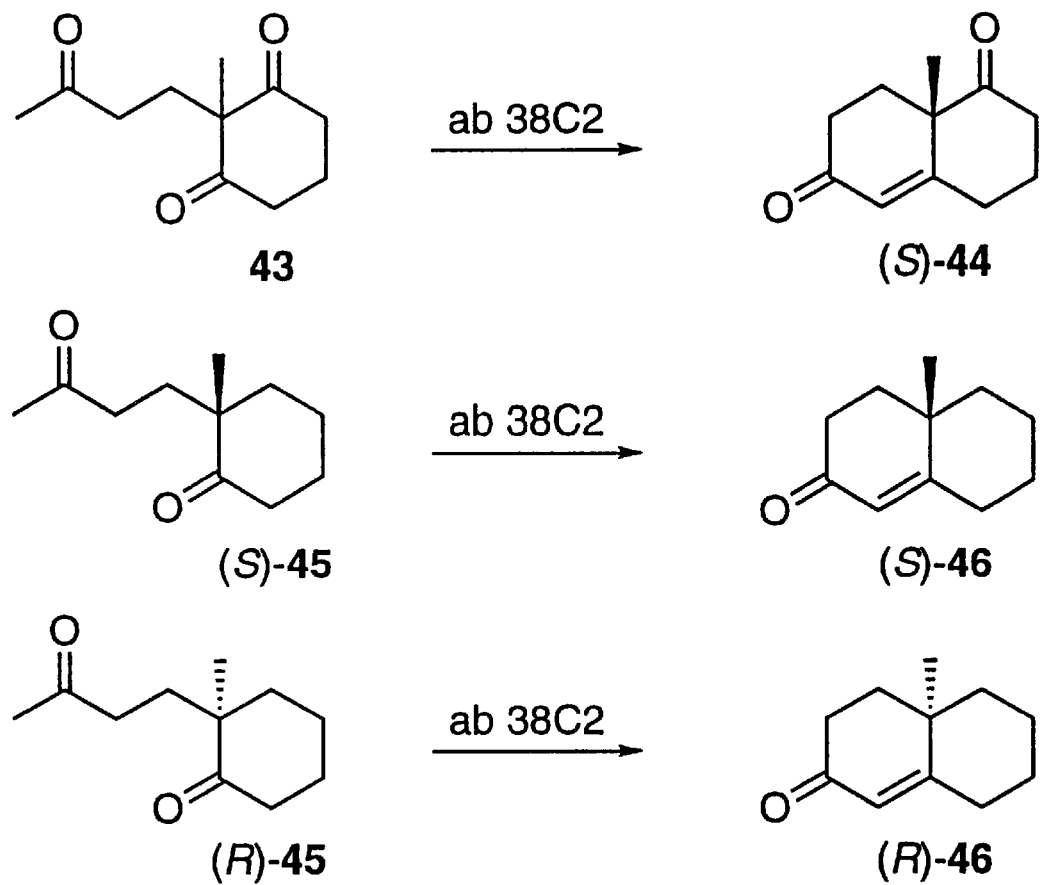
FIG. 9 illustrates antibody catalyzed synthesis of steroid partial structures (S)-44 (Wieland Miescher ketone), (S)-46 and (R)-46.

Appearance of the product 40—which is the sex pheromone of the Douglas Fir beetle 8—was monitored by HPLC. The reaction followed Michaelis-Menten kinetics (FIG. 17) and showed an excellent rate acceleration. The antibody was also incubated with the corresponding intermediate, 3-hydroxy-3-methylcyclo-hexanone. As seen in the self-aldol condensation of cyclopentanone, the elimination step leading to 40 was also catalyzed by ab 38C2. In reported experiments, 4b we tested the triketone 43 and the enantiomerically pure diketones (S)-45 and (R)-45 as substrates (FIG. 9). In all cases product formation (Wieland-Miescher ketone (S)-44 and the ketones (S)-46 and (R)-46), respectively) was catalyzed by 38C2 and proceeded with a rate which is comparable to the one found using the simple diketone 39 as substrate. All reactions followed Michaelis-Menten kinetics, the parameters of which are summarized in FIG. 17. We also examined 2-methyl-2-(3'oxopentyl)-1,3-cyclohexanedione, 2-methyl-2-(3'oxobutyl)-1,3-cyclopentanedione, and 2-methyl-2-(4'oxopentyl)-1,3-cyclohexanedione as potential substrates for these antibodies, however, no reactions with these substrates were observed.

Miscellaneous Aldol Reactions

Figure 10:
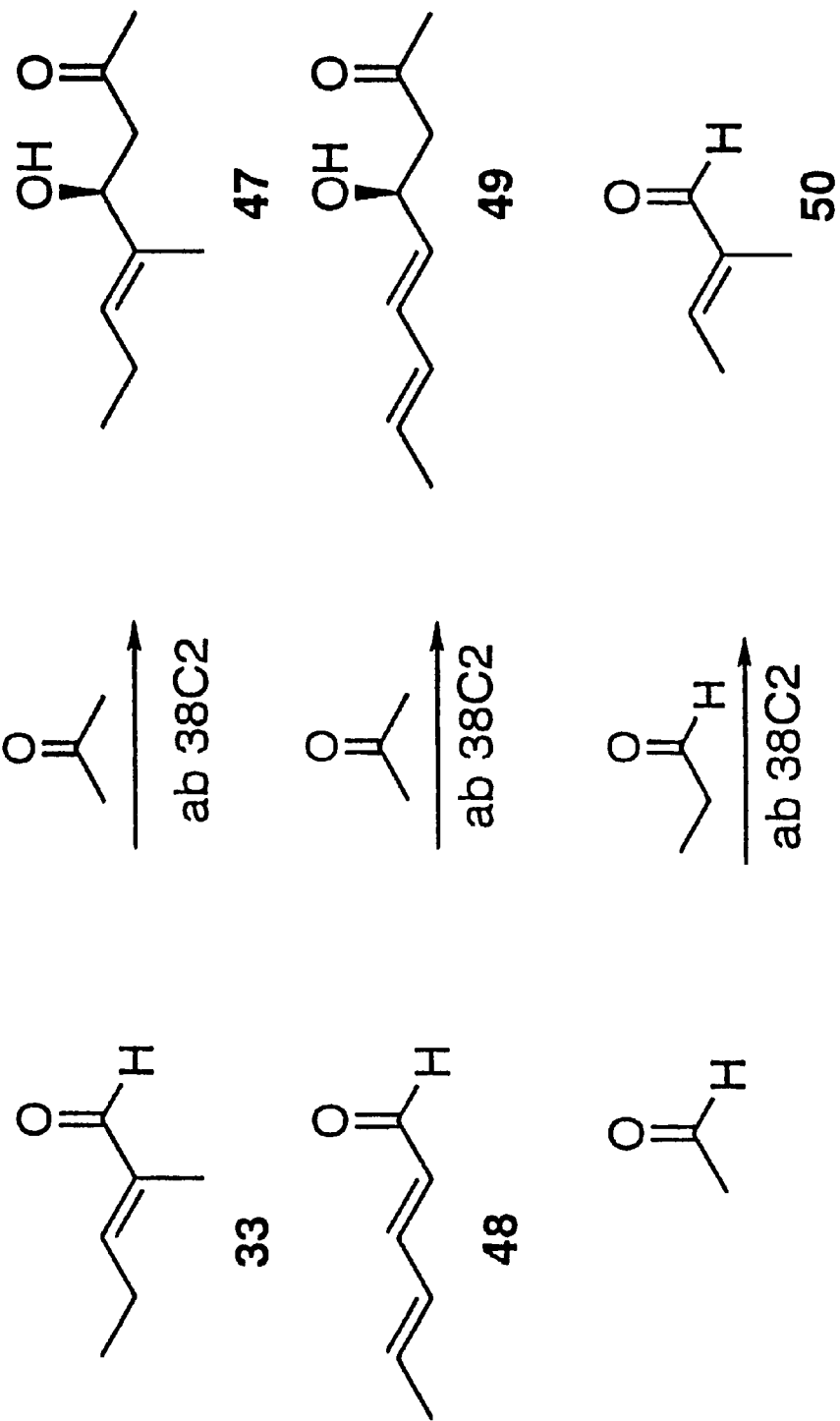
FIG. 10 illustrates aldehydes 33, 48, and acetaldehyde as acceptors in the antibody catalyzed cross-aldol reactions.

As described above, the self-aldol condensation of two molecules propionaldehyde terminates after the condensation step. The product, trans-2-methyl-2-pentenal 33 is not a substrate for a subsequent aldol addition (or condensation) of a third molecule propionaldehyde. In contrast, aldehyde 33 is a substrate if acetone is present as donor (FIG. 10). Surprisingly, the elimination of water from product 47 is not catalyzed by the antibody, although a thermodynamically favored $\alpha,\beta,\gamma,\delta$-unsaturated ketone could result. The binding pocket also accepts chain elongation in the acceptor structure as rationalized in 2,4-hexadienal 48. As seen with product 47, the antibody does not catalyze the elimination of water from the aldol addition product 49 either. We also investigated whether propionaldehyde might be a donor for other aldehydes, which would bind preferentially to the binding pocket and would give a $\beta$-hydroxy aldehyde as product or, after elimination of water, the $\alpha,\beta$-unsaturated aldehyde. To suppress the self-aldol addition, a lower concentration of the donor and a higher concentration of the acceptor aldehyde was used. A interesting situation was observed with acetaldehyde. It was found to act solely as an acceptor to give 2-methyl-2-butenal 50 with propionaldehyde as donor. 2-Hexenal, the cross-aldol condensation product of the reversed reactivity (acetaldehyde as donor and propionaldehyde as acceptor) was not detected.

As shown in FIG. 18, the antibodies catalyze cross-aldol reactions where simple aliphatic aldehydes act as acceptor substrates. The cross-aldol reaction between cyclopentanone and pentanal yielding 53 proved to be very efficient and kinetic studies revealed a $k_{cat}$ of 1.1 min–1 and a $K_m$ for pentanal of 3.9 mM. Pentanal was also a very efficient acceptor substrate when paired with hydroxyacetone as the donor. Retro-aldol reactions involving the pentanal derived products 55 and 56 were also catalyzed.

Stereoselectivity and Absolute Configurations of the Aldol Products

Both aldolase antibodies 38C2 and 33F12 catalyze highly stereoselective aldol reactions. As a general rule, acetone adds to aldehydes with si-facial selectivity whereas with hydroxyacetone a reversal of enantioface selectivity results in addition to the re-face. The products were formed in ee's up to >99% (FIG. 19). The ee's were determined by chiral HPLC and chiral GC. To assign absolute configurations, the products were synthesized by either of two ways. In case of the acetone products, we used the method developed by Paterson et al. (Paterson et al Tetrahedron 1990, 46, 4663) utilizing the diisopinocamphenyl enol borinate, prepared in situ from (–)-Ipc$_2$BOTf and acetone. The hydroxyacetone products were prepared from the corresponding $\alpha,\beta$-unsaturated ketones via Sharpless asymmetric dihydroxylation (Kolb et al. *Chem. Rev.* 1994, 94, 2483; Walsh, P. J., Sharpless, K. B. *Synlett* 1993, 605).

Figure 11:
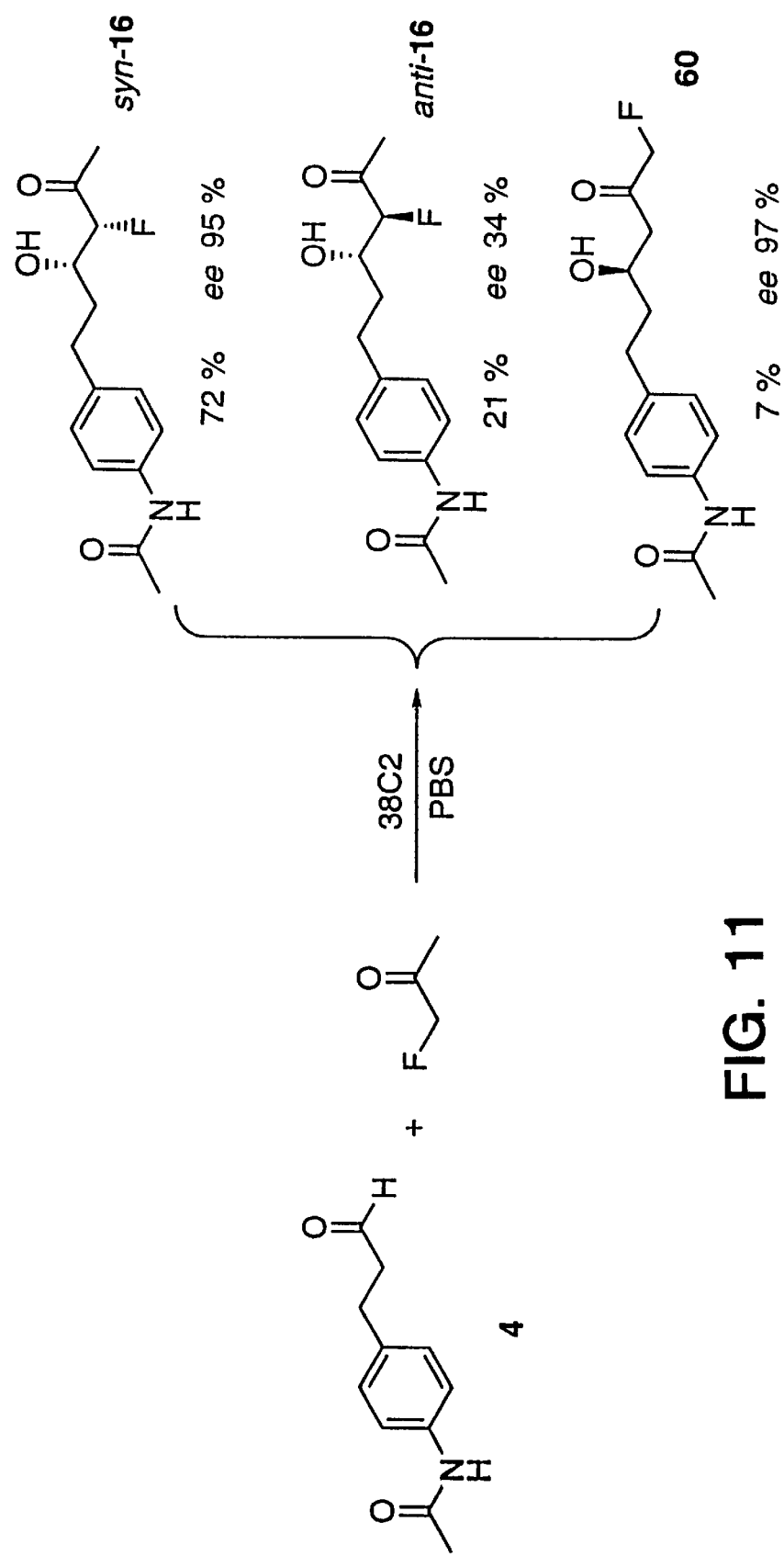
FIG. 11 illustrates the preparation of fluorinated aldols (syn-16, anti-16, and 60) by antibody catalyzed aldol reaction.
Figure 21:
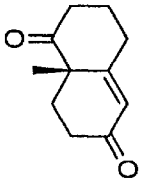
FIG. 21 illustrates the a comparison of the processes by which evolution and the immune system develop new protein functions. First, the immune system has a counterpart to each of the powerful genetic maneuvers that evolution uses. The key differences between the two processes are in the time parameter and the selection criteria following: * No background reaction observed. The value was estimated using $K_{uncat}=2.28.10-7$ M–1min–1 for the aldol addition of acetone to an aldehyde and by the fact that $k_{cat}/K_{uncat}$ for the elimination step was determined to 2250; ** $K_{uncap}=2.28.10-7$ M–1min–1 for the addition of acetone to an aldehyde. A comparison of strategies for the evolution of enzymes with those used in the evolution of an antibody response.

The highest enantioselectivities were observed for aldol reactions where conjugated aldehydes, allylic or benzylic, served as acceptors with acetone as donor. In these cases the observed enantioselectivities were always over 98% ee with either antibody catalyst. Lower enantioselectivities were obtained with aldol acceptors containing an sp3 center in the $\alpha$-position, though enantioselectivity may be increased by addition of steric bulk at this carbon center as suggested with compound 21. With acceptors of this class, the two catalysts exhibited differential degrees of stereoselectivity. The lowest degree of enantioselectivity is obtained with 4-(4'-acetamidophenyl)butyraldehyde as an acceptor and acetone as a donor to yield compound 24. The ee in this case is 20% and 3% ee, with catalysts 38C2 and 33F12, respectively. Donor, acceptor, and catalyst all exert an effect on the enantioselectivity of the reaction since use of hydroxyacetone as an aldol donor instead of acetone in the reaction with 4-(4'-acetamidophenyl)butyraldehyde provides product 58 in 77% ee. The regioselectivity of this reaction with respect to bond formation at either a position on hydroxyacetone is perfect. Only product formed by reaction at the $\alpha$-hydroxy bearing side of hydroxyacetone was detected. Study of the reaction of fluoroacetone with aldehyde 4 catalyzed by 38C2 also demonstrated regioselectivity of bond formation towards the $\alpha$-substituted carbon of fluoroacetone, however, 7% of the other regioisomer 60 was also isolated (FIG. 11). The syn-16, constituted 72% of the isolated product and was formed in 95% ee, while the anti-16, 21% of the isolated product, was formed with 34% ee. The absolute stereochemistry of these products remains to be assigned. The regioselectivity of the aldol addition of fluoroacetone catalyzed by these antibodies is opposite that observed with the natural aldolase, deoxyribose-5-phosphate aldolase, where only addition to the unsubstituted side of fluoracetone was observed (Barbas III, C. F., Wang, Y.-F., Wong, C.-H. *J. Am. Chem. Soc.* 1990, 112, 2013).

There are no known catalysts or general methodologies for the asymmetric synthesis of $\alpha$-fluoro-$\beta$-hydroxyketones such as syn-16 (Welch, J. T.; Seper, K.; Eswarakrishnan, S.; Samartino, J. *J. Org. Chem.* 1984, 49, 4720; House, H. O.; Fischer, W. F.; Gall, M.; McLaughlin, T. E.; Peet, N. P. *J. Org. Chem.* 1971, 36, 3429–3437; Kowalski, C.; Creary, X.; Rollin, A. J.; Burke, M. C. *J. Org. Chem.* 1978, 43, 260). Stereoselection involving reactions of $\alpha$-aliphatic substituted ketones, for example cyclopentanone were not studied in detail in this case due to the stereochemical lability at the $\alpha$-position of products formed with these donors in buffered aqueous solvent (Iriye, R.; Takai, K.; Noguchi, M. *Bioorg. Med. Chem. Ltrs.* 1997, 7,199; Konieczny, M. T.; Toma, P.

H.; Cushman, M. *J. Org. Chem.* 1993, 58, 4619). The anti/syn selectivity of reactions with cyclopentanone as the donor in reaction with aliphatic ketones are given below as compared to the product distribution obtained with kinetically controlled synthesis (LDA, −78C). With n-pentanal as the acceptor, 53 is produced via antibody catalysis with α anti/syn ratio nearly identical to that obtained under kinetically controlled synthesis. A reversal of selectivity is noted with heptanal as the acceptor where the syn-product predominates.

Retro-Aldolization, Catalytic Efficiency, and Proposed Mechanism

Previous biochemical studies of both catalysts and structural studies of 33F12 are all consistent with an enamine mechanism shared with the natural class I aldolase enzymes. Central to this mechanism is a chemically unique lysine residue bearing an ε-amino group with a highly perturbed pKa allowing for efficient amine based catalysis under conditions were a more typical amine would be protonated and ineffective in this chemistry. The catalytic efficiency of antibody 38C2 as an aldolase is most readily compared with simple amine catalysis by study of the retro-aldol reaction since the second-order rate constant of the amine catalyzed reaction can be directly related to $k_{cat}/K_m$ of the antibody catalyzed reaction. Kinetic studies of amine catalyzed aldol addition reactions have been reported and are approximately $10^2$-fold slower than the amine catalyzed retro-aldol reaction (Reymond, J.-L. and Chen, Y. *J. Org. Chem.* 1995, 60, 6979).

We studied the retro-aldol reaction of substrate 59 under antibody and amine catalysis where amine catalysis was studied in both buffered aqueous solvent and organic solvent (FIG. 12). Antibody 38C2 catalyzed the retro-aldolization of 59 following Michaelis-Menten kinetics ($k_{cat}$=1.4 min$^{-1}$, $K_m$=270 mM). The background rate of this retro-aldol reaction(100 mM MOPS buffer, pH 7) was determined to be 8.3×10-8 min$^{-1}$. The relative rate enhancement over background provided by the antibody for this reaction ($k_{cat}/K_{uncat}$) is 1.7×10$^7$ and the specificity constant ($k_{cat}/K_m$)is 5.2×10$^3$ min−1M−1. To date, the most efficient substrate for the 38C2 catalyzed retro-aldol reaction is 6-(4'-dimethylaminophenyl)-4-hydroxy-5-hexen-2-one. The specificity constant for this substrate is 2.0×10$^5$. The specificity constant of antibody 38C2 for this reaction exceeds that previously reported for an amine cofactor-dependent antibody aldolase by a factor greater than 10$^6$ (Reymond, J.-L. *Angew. Chem. Int. Ed. Engl.* 1995, 34, 2285).

Earlier studies have suggested that the pKa of the ε-amino group of the active site lysine, Lys H93, that is central to the chemistry of these catalysts, is highly perturbed by a hydrophobic microenvironment that disfavors protonation and charge development in the unliganded antibodies. The pKa's of the active-site lysines of 38C2 and 33F12 have been estimated to be 6.0 and 5.5, respectively. The pKa of the ε-amino group of lysine free in solution is 10.5 (Dean, J. A., in *Lange's Handbook of Chemistry* (McGraw-Hill, San Francisco, Calif. 1992), pp. 8.19–8.71). These studies also suggested an active-site hydrophobicity that approximates that of n-octanol. Therefore the second order rate constants for n-butylamine and aminoacetonitrile catalyzed retro-aldolization of 59 where determined in aqueous buffer and n-octanol. N-Butylamine was studied because of its structural similarity to the side-chain of lysine that is key in the antibody catalyzed reaction and aminoacetonitrile was studied since its pKa approximates that of the active-site lysine of the antibody. The pKa's of n-butylamine and aminoacetonitrile in water are 10.61 and 5.34 (Hupe, D. J.; Kendall, M. C. R.; Spencer, T. A. *J. Am. Chem. Soc.* 1972, 94, 1254). The relative efficiency of 38C2 over amine catalysis ($k_{cat}/K_m$)/kNH2 and the effective molarity ($k_{cat}$/kNH2) of the active site lysine of 38C2 are given in FIG. 20. Antibody 38C2 provides a 10$^6$–10$^8$ fold enhancement of the efficiency of the retro-aldol reaction of 59 as compared to the non-enzymic amine catalyzed reactions in either aqueous or organic media. The relative efficiency of 38C2 over simple amine catalyzed retro-aldolization of 59 compares favorably with the efficiency of the enzyme acetoacetate decarboxylase that has been compared with aminoacetonitrile catalyzed decarboxylation of the same substrate, acetoacetate, where ($k_{cat}/K_m$)/kNH$_2$ is 9.5×10$^6$ (Westheimer, F. H. *Procedding of the Robert A. Welch Foundation,* Houston, 1971, 15, 7; Westheimer, F. H. *Tetrahedron* 1995, 51, 3; Highbarger, L. A.; Gerlt, J. A.; Kenyon, G. L. *Biochemistry* 1996, 35, 41). Acetoacetate decarboxylase is the most studied of enzymes whose mechanism centers around an activated ε-amino group of lysine. The effectiveness of the active site amine of 38C2 is also indicated by effective molarities between 560 and 35,000 M depending on the amine and solvent system studied.

As shown in FIG. 20, n-butylamine catalysis in n-octanol is increased 63-fold compared to catalysis in aqueous solution since the amine is in its reactive unprotonated state in n-octanol. Aminoacetonitrile exhibits similar efficiency in both solvents due to its low pKa. The activation energy for this reaction should be lower in nonpolar solvents such as the active site of the antibody and n-octanol since the reaction involves charge dispersal in the transition state. A polar medium would be expected to stabilize the cationic iminium intermediates to a greater extent than the activated complex. (Reichardt, C., in *Solvents and Solvents Effects in Organic Chemistry* Ebel, H. F., Wentrup-Byne, E., Eds.; New York, N.Y., 1990, 2nd eddition, pp1–511; Heathcock, C. H. *Stereoselective Aldol Condensations,* in E. Buncel and T. Durst (eds): *Comprehensive Carbanion Chemistry.* Part B, P. 177ff. (particularly p. 198), Elsevier, Amsterdam 1984).

Figure 2:
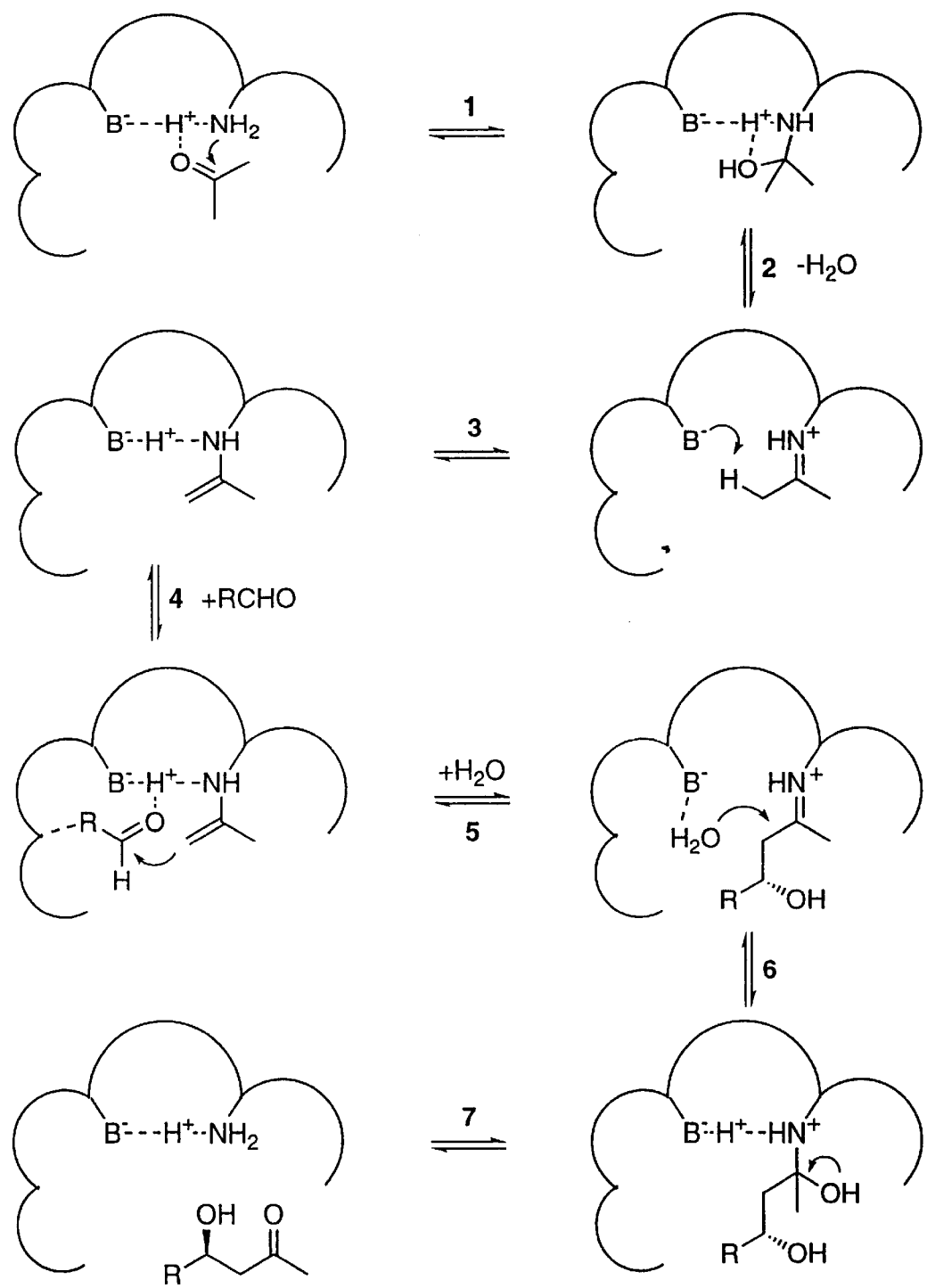
FIG. 2 illustrates detailed representation of the suggested mechanism of ab 38C2 and 33F12 catalysis of the aldol reaction. The rate determing step is presumably the C—C bond formation in step 5.

The crystal structure of unliganded 33F12 shows LysH93 within hydrogen bonding distance to a water molecule that is also within hydrogen bonding distance to the hydroxyl group of TyrL41. With the caveat that antibodies may undergo large conformational changes on binding, a mechanism analogous to that proposed for class I aldolases is shown in FIG. 2 and appears most likely. In the proposed mechanism, TyrL41 may act as the base. Acceptor activation appears to be essential since we have failed to trap the enamine with addition of alkylating substrates such as 4-nitrophenethyl bromide or α,β-unsaturated substrates such as methyl vinyl ketones according to Stork enamine (Stork et al. *J. Am. Chem. Soc.* 1963, 85, 20) or Michael reactions (Lucero, M. J.; Houk, K. N. *J. Am. Chem. Soc.* 1997, 119, 826; for leading references, see: Pfau, M.; Revial, G.; Guingant, A.; d'Angelo, J. J. *J. Am. Chem. Soc.* 1985, 107, 273; d'Angelo, J.; Desmaële, D.; Dumas, F.; Guingant, A. *Tetrahedron: Asymmetry* 1992, 3, 459; Jabin, I.; Revial, G.; Tomas, A.; Lemoine, P.; Pfau, M. *Tetrahedron: Asymmetry* 1995, 6, 1795; Cavé, C.; Desmaële, D.; d'Angelo, J. *J. Org. Chem.* 1996, 61, 4361).

Figure 3:
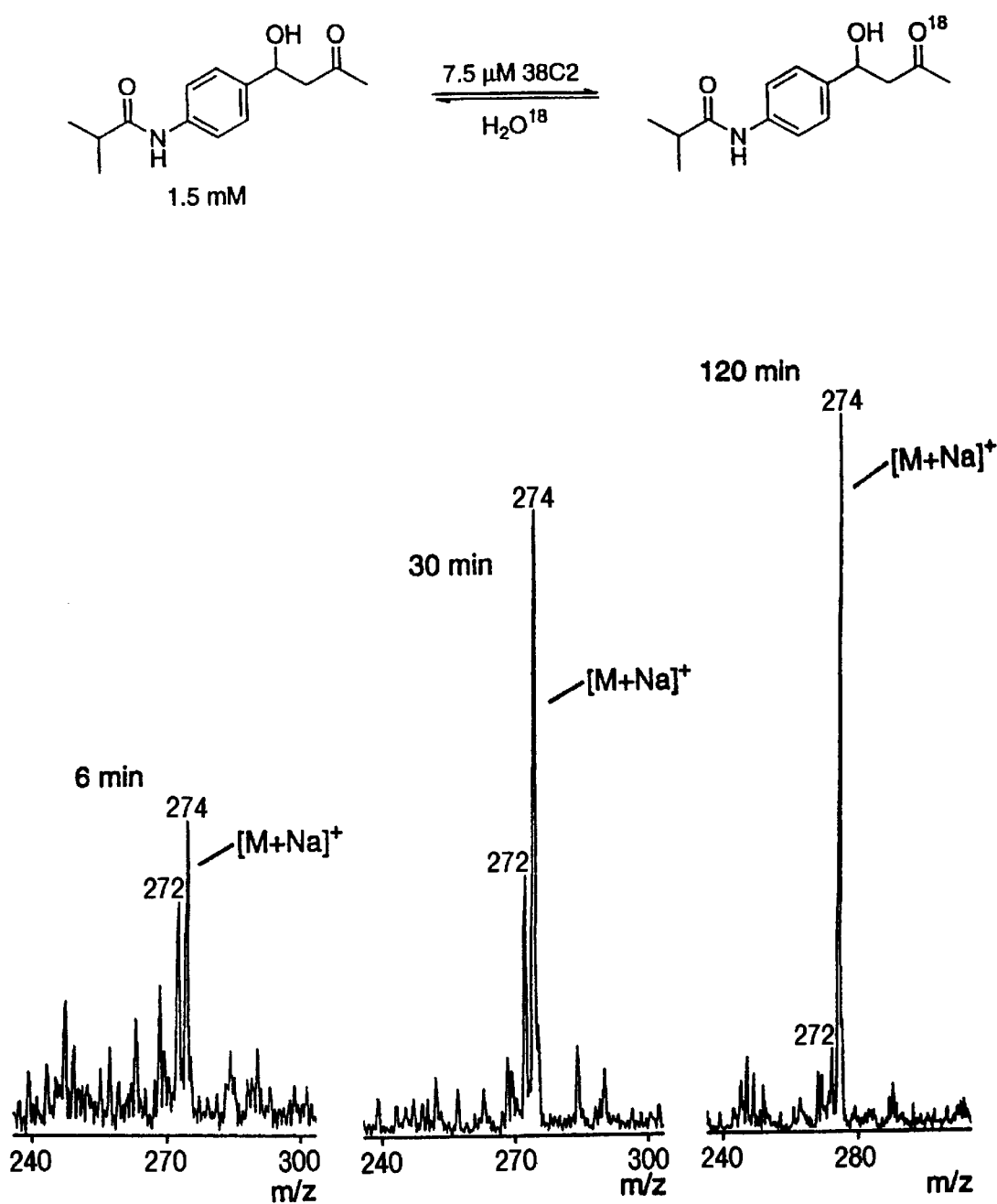
FIG. 3 illustrates mass spectra from electrospray MS showing the antibody catalyzed O-exchange of the aldol product 59 in buffered 98% 18O-labeled water. The m/z of 272 corresponds to the starting material whereas the antibody catalyzed exchange (presumably via a covalently bound intermediate) incorporated 18O to produce m/z of 274. Negligible 18O incorporation into 59 was observed in the absence of ab 38C2 under otherwise identical conditions.
Figure 4:
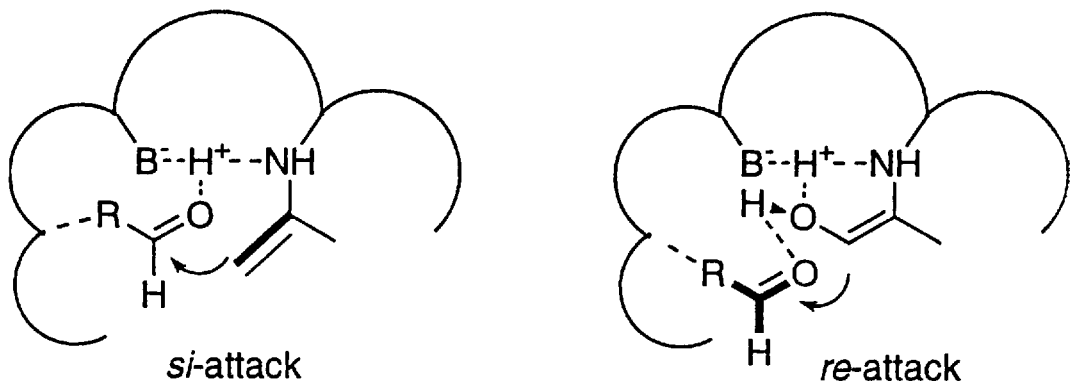
FIG. 4 illustrates the potential mechanistic origin of enantioselectivities where acetone and hydroxyacetone serve as aldol donor substrates.

Acceptor activation and the microenvironment in which it occurs, however, must be balanced so as not to facilitate formation of the unreactive gem-diol form of the aldehyde. Enamine formation and or the C—C bond forming/breaking step are rate limiting with these catalysts. Study of the 38C2 catalyzed retro-aldolization of 59 in 18O-labeled water by electrospray mass spectrometry showed rapid antibody catalyzed incorporation of 18O into substrate 59 (FIG. 3). Within 6 minutes, 1 mol % 38C2 catalyzed 18O incorporation into more than 50% of the substrate 59 molecules where no incorporation in the control reaction not containing antibody was seen at this time point. This result contrasts what we observed in similar studies of 38C2 catalyzed decarboxylation of a β-ketoacid where imine formation is rate-limiting and catalysis of 18O exchange back into the substrate was not observed. Reactions involving hydroxyacetone as donor are faster than those involving acetone. This observation is also in support of enamine formation being at least partially rate determining since ab initio molecular orbital calculations predict a lower energy of activation for the imine to enamine interconversion for hydroxyacetone relative to acetone by approximately 2 kcal/mol due to the electron-withdrawing character of the hydroxy group on hydroxyacetone that facilitates proton abstraction at the a-carbon (Lin, J.-F.; Wu; C.-C.; Lien, M.-H. *J. Phys. Chem.* 1995, 99, 16903). This together with an increased relative stability of the enamine formed at the hydroxy bearing side of hydroxyacetone explains the perfect control of the regiochemistry of hydroxyacetone aldols where bond formation has only been detected at the α-position bearing the hydroxyl group. By similar arguments, the observed regioselectivity of fluoroacetone addition is also in accord with these reported ab initio molecular orbital calculations. The reversal in the enantiofacial selectivity of the addition of hydroxyacetone remains to be completely explained. The α-syn stereochemistry of the hydroxyacetone derived products 54 and 58 can be rationalized by the preferential formation of the Z-enamine of hydroxyacetone, stabilized over the E-configuration via intramolecular hydrogen bonding, and subsequent attack on the re-face of the acceptor as shown in FIG. 4. Branching at the α-position of the enamine may result in a reorganization of an activating water molecule or another amino acid side-chain that serves this function, altering the enantiofacial selectivity. The observation of both syn and anti products in additions of cyclopentanone to aldehydes, products 51–53, supports the availability of both faces of the acceptor aldehyde towards attack with this enamine which is limited to formation of an E-enamine. Diminished enantioselectivity with substrates such as 6 over the high enantioselectivities observed with benzylic or allylic acceptors 3,7, and 8 is consistent with more efficient enantioface selectivity with acceptor molecules with fewer degrees of freedom. Further insight into the chemical mechanism of these catalysts will come with the solution of the X-ray crystal structure of antibody 33F12 bound to hapten 1.

Figure 5:
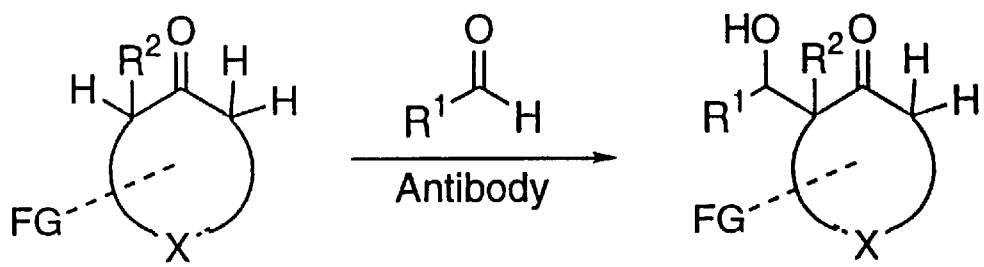
FIG. 5 illustrates the consensus ketone-aldehyde cross-aldol substrates for antibodies 38C2 and 33F12.
Figure 6:
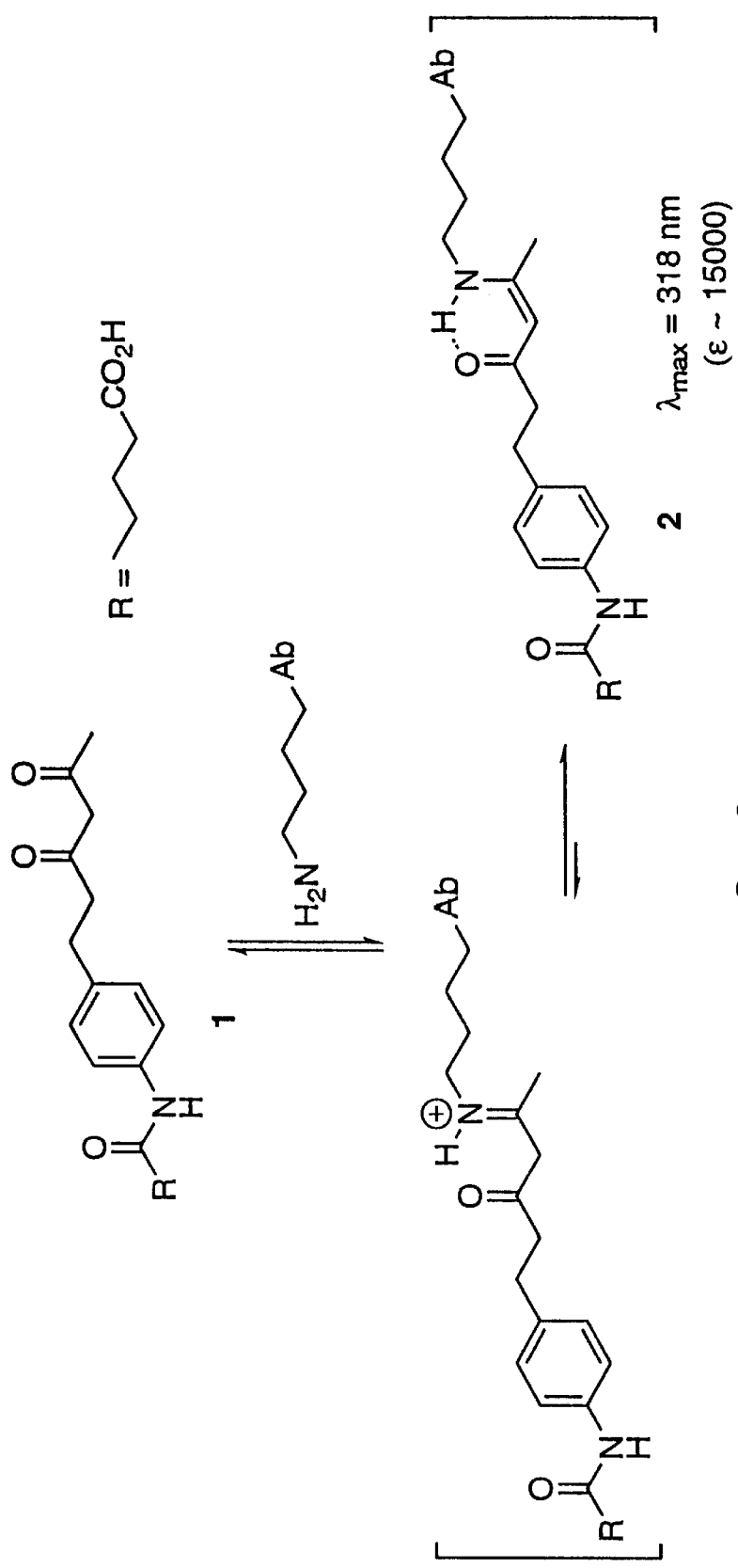
FIG. 6 illustrates a mechanism of trapping the essential ε-amino group of a lysine residue in the antibody binding site using the β-diketone hapten 1.

Antibodies 38C2 and 33F12 are capable of efficiently catalyzing a wide variety of ketone-ketone, ketone-aldehyde, aldehyde-ketone, and aldehyde-aldehyde intermolecular aldol reactions, and in some cases to catalyze their subsequent dehydration to yield aldol condensation products. A number of intramolecular aldol reactions have also been defined. Catalysis of all intramolecular aldol reactions examined yields the corresponding condensation products. The consensus donor and acceptor substrates are given in FIG. 5. The primary limitation in donor specificity appears to be an inability of the catalysts to accept ketones that are branched at the non-bond forming α-position, whereas acceptor substrates are only limited to the extent that they are relatively hydrophobic aldehydes or ketones since no polyhydroxylated aldehydes have yet been defined as substrates. The scope of these antibody catalysts exceeds that observed with any known natural enzyme aldolase or transition-metal based aldol catalysts. When acetone is the aldol donor substrate in a ketone-aldehyde crossed aldol reaction, a new stereogenic center is formed by attack of the si-face of the aldehyde with ee's in most cases exceeding 95%. With hydroxyacetone as the donor substrate, attack occurs at the re-face of the aldehyde generating an α,β-dihydroxyketone with the two stereogenic centers having a α-syn configuration, (3R, 4S). These reactions proceed with 70 to >99% ee. The major product of a cross-aldol reaction with fluoroacetone as the donor substrate is a syn α-fluoro-β-hydroxy ketone formed in 95% ee.

This work highlights the ability of reactive immunization to produce catalysts that are efficient yet broad in scope. Since such antibodies are tailor-made and optimized by the immune system to covalently bind the hapten, the binding pocket is not necessarily refined with respect to non-covalent interactions with the immunogen. Consequently, the biocatalyst can accept a variety of substrates which differ enormously with respect to their physico-chemical properties. Antibodies 38C2 and 33F12 are useful additions to the repertoire of a symmetric catalysts due to their tremendous scope, efficiency, and stereoselectivities. This has been demonstrated herein with syntheses up to the 1 gram scale and in the highly enantioselective total syntheses of 10 different brevicomins (vida infra). Unlike current transition metal catalysts, the antibodies reported here catalyze both the aldol and retro-aldol reaction allowing for the preparation of both enantiomers of β-hydroxyketones with high optical purity either by enantioselective synthesis or kinetic resolution (vida infra). The issue of scale in antibody catalyzed reactions can be addressed with currently available technologies, particularly the heterologous expression of antibodies in plants and algaes, where low-cost production of these catalysts on a multi-ton scale could be achieved to allow for the "green synthesis" of aldols on a virtually unlimited scale. Antibody 38C2 is now commercially available from the Aldrich Chemical Company (Hiatt, A. *Nature* 1990 334, 469; Hiatt, A.; Ma, J. K. *Int. Rev. Immunol.* 1993, 10, 139; Ma, J. K.; Hiatt, A.; Hein, M.; Vine, N. D.; Wang, F.; Stabila, P.; van Dolleweerd, C.; Mostov, K.; Lehner, T. *Science* 1995, 268, 716; Franken, E.; Teuschel, U.; Hai, R. *Curr. Opin. Biotechnol.* 1997, 8, 411).

EXAMPLE 2

Capacity of Immune Selection to Evolve Antibody Aldolases with the Rate Acceleration of Natural Enzymes but Much Broader Scope Structural and mechanistic studies show that when the selection criteria of the immune system are changed, antibodies evolve that have the efficiency of natural enzymes yet are much more accepting of a wide range of substrates. The catalytic antibodies were prepared by reactive immunization, a process whereby the selection criteria of the immune system from simple binding to chemical reactivity. This process was used to produce aldolase catalytic antibodies that approximated the rate acceleration of the natural enzyme used in glycolysis. Unlike the natural enzyme the antibody aldolases catalyzed a variety of aldol reactions and decarboxylations. This work has implications for the natural course of enzyme evolution.

The central dilemma in the development of alternative protein catalysts concerns duplicating the rate accelerations of natural enzymes while increasing their versatility. For new enzymes to be optimally useful in chemistry they must be both efficient as well as capable of accepting a variety of substrates. Whereas the need for efficiency is obvious, the scope problem arises because enzymes would be more useful if they could catalyze a class of reactions using diverse substrates. To solve this problem we have used antibody catalysis.

The approach is best highlighted by comparing the processes by which evolution and the immune system develop new protein functions (FIG. 28). First, the immune system has a counterpart to each of the powerful genetic maneuvers that evolution uses(Lerner, S. J. Benkovic and P. G. Schultz, *Science* 252, 659 (1991); P. G. Schultz and R. A. Lerner, *Science* 269, 1835 (1995)). The key differences between the two processes are in the time parameter and the selection criteria. During evolution natural selection occurs on the basis of improved function or fitness whereas in the immune system effective clonal selection is based on improved binding. Natural enzymes are presumably selected because of catalytic efficiency with some enzymes reaching "perfection" with binding interactions funneling into a chemistry that is most compatible with substrate turnover. Thus each system has comparable genetic maneuvers to generate new functions but the systems differ in the selection criteria and time-line. The central question is will the immune system yield efficient catalysts in real time if it's selection criteria are switched from simple binding to function? This way of thinking about the problem leads to the idea that the most powerful way to develop new antibody catalysts is to select them based on their ability to accomplish a desired chemical feat. But, to first approximation, the scope problem remains because, regardless of the selection criteria, the induced antibodies would be highly refined for a given substrate as a consequence of the immune process. There is, however, an additional feature of functional selection during antibody induction that might allow for the development of catalysts that are both efficient and broad in scope. Consider, a process of antibody induction that selects on a chemical interaction that forms a covalent bond with the antibody rather than the usual concert of noncovalent interactions (FIG. 24). In the noncovalent case a series of somatic mutations lead to improved interactions with the hapten and a concomitant increased binding specificity toward the inducing molecule. Thus, if an enzyme were to result from this process it would have the restricted substrate specificity characteristic of most natural enzymes. In the covalent case the usual process of somatic refinement may be aborted because any clone that carries an antibody that has made a covalent bond with the antigen will be selected above others because no matter how many good noncovalent interactions competing clones generate they cannot equal the binding energy achieved by the single covalent event.

When the covalent event appears early in the process of antibody evolution, any selective pressure on the refinement process may cease leading to antibodies capable of achieving a chemical reaction in a binding pocket that is, otherwise, not highly refined. Thus, some antibodies selected by reactive immunization can be efficient because, like enzymes, they were selected on the basis of a chemical reaction, yet unlike enzymes they are broad in scope because the usual requirement for refinement of the binding pocket has been circumvented.

Our procedure, termed reactive immunization, allows for the production of antibodies with the properties described above (Wagner et al. *Science* 270, 1797 (1995); Wirsching et al. *Science* 270, 1775 (1995)). The method provides a means to select antibody catalysts in vivo on the basis of their ability to carry out a chemical reaction. This procedure departs from the usual mode of immunization in which care is taken to use antigens that are as inert as possible so that the resultant antibodies can interact with targets that are in their native state. In the process of reactive immunization the opposite is done. A reactive antigen is designed so that a chemical reaction or reactions, such as the formation of a covalent bond, occurs in the binding pockets of the antibody molecules during their induction in the immune response. The chemistry that occurs in the antibody during it s induction is designed to be an integral part of a reaction coordinate when the corresponding substrates are used.

We now compare aldolases that use the same chemical mechanism—one evolved in nature and the others catalytic antibodies obtained by reactive immunization.

The Reactive Immunization Process and the Antibody Aldolase

The antibody catalyst that we wished to make was an aldolase in which the enamine mechanism of the natural enzymes has been imprinted within the antibody binding site. It was prepared by immunizing animals with a 1,3-diketone hapten such that any antibody that had an appropriately placed lysine residue of the proper chemical reactivity would attack one of the carbonyl groups to form α carbinolamine that would subsequently collapse to a Schiff base. A stable covalent interaction with the antibody is formed when the Schiff base tautomerizes to an enamine that, because of a second carbonyl functionality in the α-position, is a stable vinylogous amide, FIG. 23.

The vinylogous amide has a strong U.V. absorption outside the range of the protein (approx. 316 nm) and, thus, instead of screening for binding, we screen for the new absorption that indicates that the antibody has evolved the central chemical mechanism of the natural aldolases. Antibodies made by this procedure have been shown to catalyze aldol and decarboxylation reactions, all of which proceed by the same enamine mechanism utilized by the natural class I aldolases (Björnestedt, G. Zhong, R. A., Lerner and C. F. Barbas III, *J. Am. Chem. Soc.* 118, 11720 (1996)). We now describe their scope, relative efficiency, and structure.

The enzyme, fructose 1,6-diphosphate aldolase is the most studied of the protein aldolases, it is found in each of the three domains of life . The enzyme is central to glucose metabolism (glycolysis=sugar splitting=aldolase), catalyzing either net cleavage or synthesis during glycolysis or gluconeogenesis, respectively. In nature the enzyme catalyzes the cleavage of fructose 1,6-diphosphate to dihydroxy-acetone phosphate and glyceraldehyde-3-phosphate. Class I aldolase enzymes proceed by the enamine mechanism (FIG. 24). The mechanistic symmetry about the C—C bond forming step allows the β-diketone selection to direct mechanistically identical reaction coordinates around this step, FIG. 24.

The Scope and Efficiency of the Antibody Catalyst

Unlike fructose 1,6-diphosphate, which is very narrow in scope, particularly with respect to donor activation, the antibody aldolase is very broad in scope accepting a wide variety of substrates (FIG. 22). To date more than 100 different aldol additions or condensations or both have been effected by th is single catalyst. The catalyst is capable of accelerating aldehyde-aldehyde, ketone-aldehyde, and ketone-ketone reactions. For cross-aldol reactions, various ketones are accepted as donors such as aliphatic open chain (for example, acetone to pentanone series), aliphatic cyclic (cyclopentanone to cycloheptanone), functionalized open chain (hydroxyacetone, dihydroxyacetone, fluoroacetone) and functionalized cyclic ketones(2-hydroxycyclohexanone). The active site lysine residue of the biocatalyst is able to convert these ketones into the corresponding enamines which are the key intermediates that are able to attack both aldehydes and ketones. As seen for the donors, the antibody also accepts very different aldehyde substrates, such as pentanal, 4-acetamidobenzaldehyde, or 2,4-hexadienal. During the course of our investigations it turned out that the antibody was also able to catalyze self-aldol condensations of acetone or cyclopentanone provided that no acceptor aldehyde was present for a cross-aldol reaction. In particular, propionaldehyde is also a substrate for a self-aldolcondensation now acting as a donor and acceptor at the same time. The reaction terminates at the dimer step although the product (trans-2-methyl-2-pentenal) contains a reactive aldehyde functionality and might be an acceptor itself for a subsequent addition step. Such a reaction was found to be catalyzed by the antibody but only when acetone was donor. Here, no water elimination occurred although the aldol addition product was labile to dehydration.

To determine whether the water elimination in the case of the self-aldolcondensation reactions were also catalyzed, we chemically synthesized the aldol addition product of cyclopentanone and incubated it with the antibody. Elimination of water from this substrate was catalyzed and followed typical Michaelis-Menten kinetics. Intramolecular self-aldol condensations were studied. The antibody was found to catalyze the formation of 3-methyl-2-cyclohexenone in one step using 2,6-heptanedione as substrate. This Baldwin favored 6(enolendo-trig)-exo-trig process is still catalyzed by the antibody if one part of the 2,6-diketone is incorporated into a cyclohexanone system. Thus, the formation of A-B ring partial structures of steroids is catalyzed starting from the corresponding precursors. Most striking is the example in which the antibody catalyzes the cyclization of an achiral triketone to the (S)-enantiomer of the Wieland Miescher ketone with an enantiomeric excess (ee) >95%. Consideration of the original hapten structure and comparison of it to the later structure with its geometrical requirements illustrates the power of reactive immunization, since the biocatalyst was not originally designed for such a substrate geometry but for function.

All antibody-catalyzed aldol reactions followed typical Michaelis-Menten kinetics except the benzaldehyde derivatives that gave a slight substrate inhibition at higher concentrations (>2 mM). Typical values for the Michaelis constants $K_M$ of the donors in cross-aldol reactions range from 1 mM to 1 M, reflecting the ability of the antibody to accept various different ketones. Values for $K_M$ of the acceptor aldehydes range from 20 $\mu$M to 500 $\mu$M. The aromatic portion of these molecules is in part responsible for an increased recognition by the active site. In addition, the hydrophobicity of these compounds acts as a driving force, facilitating their partitioning into the active site. In self-aldol and intramolecular aldol condensation reactions, values for $K_M$ range from 1 to 5 mM. The $K_M$'s for the retroaldol reactions were more favorable and typically ranged from 15 to 400 $\mu$M. Characteristic values for $k_{cat}$ of all reactions range from $10^{-3}$ to 5 min$^{-1}$ and show a ratio of $k_{cat}/k_{uncat}$ of $10^5$ to $10^7$.

Given that each protein will catalyze the cleavage of a α-hydroxy ketone to an aldehyde and a ketone, we compared the efficient cases for each that are highly similar retro-aldol reactions (FIG. 25). For FDP aldolase, the preferred reaction is the cleavage of fructose 1,6-diphosphate to dihydroxyacetone phosphate and glyceraldehyde 3-phosphate, whereas in the antibody case the cleavage of 6-(4'-dimethylaminophenyl)-4-hydroxy-5-hexen-2-one to acetone and 4-dimethylamino-cinnamaldehyde is preferred. The antibody avoids the need for the charged phosphate handles on the natural substrate. The catalytic turnover achieved by the antibodies is within 10 times that of the natural enzyme in this case. Further, the turnover efficiency is maintained for a variety of reactions (FIG. 26).

Evolution of Diverse Catalytic Function Built on Initial Reactivity

In addition to the aldol reaction, the antibody catalyzes the decarboxylation of β-keto acids with a protonated Schiff serving as the electron sink, FIG. 27. Indeed, a few natural aldolases have been shown to catalyze biologically relevant decarboxylation reactions in a mechanistically analogous fashion Vlahos and E. E. Decker, *J. Biol. Chem.* 261, 11049 (1986).

An alternative route to diversification of mechanism involves the use of cofactors. In natural enzymes, cofactors expand the repertoire of reactions catalyzed. If a catalyst such as the antibody described above is envisioned as a model of a primordial catalyst, its scope could be expanded by the presence of a cofactor such as pyridoxal phosphate with subsequent further evolutionary refinement. This relatively simple maneuver would convert an enzyme with an active site lysine into a pyridoxal-dependent enzyme capable of catalyzing a many amino acid based transformations. These reactions include transaminations, racemizations, decarboxylations, aldol reactions, and elimination and replacement reactions (John, *Biochimica et Biophysica Acta* 1248, 81 (1995); H. Wada and E. E. Snell, *J. Biol. Chem.* 237(1), 133 (1962)). In these enzymes the coenzyme is bound in an reversible iminium linkage formed by a reaction between the ε-amino group of the active site lysine and the carbonyl group of the cofactor to form an imine that has a characteristic absorption between 360 and 420 nm. To test these ideas we studied the ability of the catalytic antibody to sequester the cofactor pyridoxal in its active site, and found that the antibody 33F12 binds the cofactor in the typical internal aldimine fashion. Later addition of 2,4-pentanedione shows that the aldimine is formed reversibly with the same lysine residue used in the aldol chemistry. The same activity was observed with antibody 38C2. This simple addition of a natural cofactor may extend the scope of the aldolase antibodies allowing a diverse new class of reactions. In this way we might duplicate a process that nature has used to create experimentally enzyme diversity from initial reactivity.

A Chemically Reactive Lysine

In that the rate accelerations of the two aldolases are comparable, we were interested in the ways that clonal selection and natural selection each solved the chemical problems in the catalytic event. The first step in the aldol reaction is the nucleophilic attack of an ε-amino group of lysine on a carbonyl group. For the ε-amino group to be nucleophilic it must be in its uncharged form. However, the $pK_a$ of this amino group in lysine in aqueous solution is 10.5 (Dean, in *Lange's Handbook of Chemistry* (McGraw-Hill, San Francisco, Calif. 1992), pp. 8.19–8.71). Since both natural and antibody aldolases depend on a non-protonated lysine as a nucleophile and operate with maximal activity at neutral pH where the ε-amino group of lysine normally would be protonated, the $pK_a$ of this group must be perturbed.

The dependence of $k_{cat}/K_M$ and $1/K_M$ as a function of pH for the retroaldol reaction showed an acidic limb $pK_a=$ 6.3–6.6. This approximates what has been observed in studies of the pH dependence of catalysis of FDP aldolase. While ideally the dependence of $k_{cat}/K_M$ and $1/K_M$ on pH should follow the ionization state of the free catalyst and free substrate, in a complex mechanism like that displayed here with several intermediate steps at different degrees of protonation, a kinetically determined $pK_a$ may not represent a real ionization constant since it can be composed of ratios of several rate constants and the rate limiting step may change with pH.

A more straightforward approach to determine the $pK_a$ of the essential lysine that avoids some of the complexity of the retro-aldol reaction is based on the ability of the antibodies to form enamines with β-diketones. The aldol antibodies react stoichiometrically with β-diketones, such as 3-methyl-2,4-pentanedione, to form stable vinylogous amides, completely inhibiting aldolase activity. The reaction of 3-methyl-2,4-pentanedione was monitored spectrophotometrically by following the absorption of the antibody-enamine complex 3 now at 335 nm. The pH dependence of this reaction is shown in FIG. 29 and is described by a simple titration curve with a $pK_a$ of 5.5 and 6.0, for antibodies 33F12 and 38C2, respectively (These kinetic arguments follow from the classic work of D. E. Schmidt, Jr. and F. H. Westheimer, *Biochemistry* 10, 1249 (1971)). Study of the dependence of the rate of enamine formation on pH with 2,4-pentanedione yielded the same $pK_a$. The $pK_a$'s of the protons at the 3 positions of 2,4-pentanedione and 3-methyl-2,4-pentanedione are 8.87 and 10.65, respectively (P. Y. Bruice, *J. Am. Chem. Soc.* 112, 7361 (1990)). These studies, together with the those of the pH dependence of retroaldol activity, demonstrate that these proteins contain active-site lysines with a perturbed $pK_a$'s.

From the work of Westheimer and his colleagues on another Schiff base forming enzyme, acetoacetate decarboxylase, we know that chemical tuning of a reactive lysine for Schiff base formation at neutral pH may be accomplished, at least in part, by another protonated lysine residue that lies in close proximity electrostatically perturbing the $pK_a$ of the amine nucleophile. A second alternative mechanism for the perturbation of the $pK_a$ of an amine is based on a hydrophobic microenvironment (P. A. Frey, F. C. Kokesh and F. H. Westheimer, *J. Am. Chem. Soc.* 93, 7266 (1971); F. C. Kokesh and F. H. Westheimer, *J. Am. Chem. Soc.* 93, 7270 (1971); L. A. Highbarger, J. A. Gerlt and G. L. Kenyon, *Biochemistry* 35, 41 (1996). 16. J. K. Lee and K. N. Houk, *Science* 276, 942 (1997); S. Dao-pin, D. E. Anderson, W. A. Baase, F. W. Dahlquist and B. W. Matthews, *Biochemistry* 30, 11521 (1991)).

A Promiscuous Hydrophobic Pocket Surrounding a Structurally Unique Lysine

In order to gain a better structural understanding of the nucleophilic character of the single reactive Lys within these antibodies and to explore the structural features that explain their scope, we cloned and sequenced their genes and determined the three-dimensional X-ray crystal structure of the antigen binding fragment, Fab, of 33F12. The sequences of 33F12 and 38C2 revealed 26 and 25 Lys residues, respectively. The antibodies were determined to be somatic variants of a single VDJ rearrangement and differed by 9 amino acids each in $V_L$ and $V_H$.

The structure of 33F12 was determined by molecular replacement at 2.15 Å resolution. The overall structure of the native Fab is similar to other known Fab structures (FIG. 30). The elbow angle, which relates the pseudo twofold axes of the $V_L$-$V_H$ and $C_L$-CH1 to each other is 151.4—and within the observed range for Fab molecules (23). The entrance of the antigen binding site of 33F12 is a narrow elongated cleft (FIG. 31). The binding pocket is more than 11 Å deep, expanding with depth. The depth of the pocket is comparable to pockets of antibodies raised against other small haptenic molecules. At the bottom of the pocket LysH93 is found within a hydrophobic environment (FIG. 30). A second LysH52b is located at the top of CDR-H2, with its side chain pointing towards the outside of the molecule. In antibody 38C2 LysH52b is mutated to an Arg while LysH93 is common to both. A sequence comparison of the CDRs with other known antibody molecules reveals some interesting and unusual features of antibody 33F12. Residue H93 is Ala in most antibodies. Only two other antibodies of known structure contain a Lys in that position, the esterolytic antibody 17E8 and the chimeric Fab fragment of the carcinoma-binding antibody B72.3. Furthermore, residue H94, which is usually an Arg in other antibodies, is replaced by a hydrophobic Ile in 33F12. The Arg at position H94 frequently forms a salt bridge with an aspartic acid at H101. Utilization of the JH3 germline by both antibodies, the only JH segment not to encode an Asp at this position, precludes this interaction.

Analysis of the combining site of Fab' 33F12 (FIG. 32A) shows that LysH93 is surrounded by mostly hydrophobic side chains and is in van der Waals contact with residues LeuH4, MetH34, ValH37, CysH92, IleH94, TyrH95, SerH100,TyrH102 and TrpH103. With the exception of IleH94 that is a Thr in 38C2, the residues in van der Waals contact with LysH94 are conserved in both antibodies. Further, all residues but Ile94 in the V and J gene segments that form these contacts are encoded in the germline gene segments used by these antibodies. The V gene encoded residues that differ between the antibodies contribute little to the refinement of the pocket suggesting that lysine H 93 appeared early in the ontogeny of these catalysts and the remaining mutations were the result of neutral drift during immunological selection. Within this pocket, only one charged residue is within an 8 Åradius of the Nz of LysH93. The carboxyl of AspH50 is located at about 7.4 Å, too far for any hydrogen bond or salt bridge. In addition, LysH93 does not form any hydrogen bonds with any main chain carbonyl oxygen. In B72.3, AspH101 is absent, but LysH93 forms a charged hydrogen bond with the main chain carbonyl oxygen of TyrH96 that is proposed to be responsible for the unusual CDR-H3 loop conformation. The inventor's also describe a hydrophobic pocket for substrate recognition (Zhou, J. Guo, W. Huang, R. J. Fletterick, T. S. Scanlan, *Science* 265, 1059 (1994)), but, in addition, there are the charged ArgH94 and AspH101 residues. Here, the LysH93 residue forms a salt bridge to AspH101 (LysH93Nz-AspH101Od1 3.2 Å) in which the positively charged Lys is proposed to stabilize oxyanion formation. Thus, as no salt bridges can be formed in 33F12, and it appears within a hydrophobic environment, the $pK_a$ would be perturbed and allow an uncharged LysH93 to function as a strong nucleophile.

In order to further define the mechanism by which the $pK_a$ of the ε-amino group was perturbed we synthesized a series of related β-hydroxy ketone substrates that differed in a defined manner with respect to their hydrophobicity. Study of the linear free energy relationship between substrate partitioning into n-octanol and $k_{cat}/K_m$, the Hansch correlation, shows that the active site of antibody 33F12 is 1.1 times more hydrophobic than n-octanol (FIG. 33). This analysis together with the observation that the antibody lacks of a positively charged amino acid side chain in the vicinity of Lys H93 supports of the possibility that the $pK_a$ of Lys H93 is perturbed by a hydrophobic microenvironment that disfavors protonation and charge development on its ε-amino group in the unliganded antibody. Thus, we have a picture of the evolutionary events that lead to the efficiency and promiscuity of this catalyst. A lysine residue appeared early during somatic refinement in a germline antibody containing an otherwise hydrophobic pocket. The insertion of this residue into this hydrophobic microenvironment resulted in chemical reactivity that was efficient enough to be selectable. Once this covalent process appeared, the binding pocket did not further evolve toward high specificity.

A Vantage Point on Enzyme Evolution

Protein enzymes achieve their efficiency, in part, as a result of transition state stabilization, strain, acid-base catalysis, and proximity. The protein scaffold of each enzyme has evolved to permit the concerted interaction of these individual effects so that together they provide remarkable rate accelerations. The requirement for these concerted effects, as facilitated by a permissive protein scaffold, has led to questioning of whether artificial proteins can match the efficiency of natural enzymes (Jencks. In: Catalysis in Chemistry and Enzymology. A. Meister (Ed.). Dover Publications, Inc., Mineola, N.Y., 1975. 31. J. R. Knowles, *Nature* 350, 121 (1991)).

In principle, the catalytic potential of proteins can be explored by antibodies because a set of binding pockets can be programmed to interact with substrates much as enzymes do. Although many catalytic antibodies have been made and shown to have good rate accelerations, it has not been possible to compare them to natural enzymes because they utilize different mechanisms. Thus, the fundamental question about whether other proteins can be made as efficient as natural enzymes had not been answered. We have now shown that antibodies and enzymes can be of comparable catalytic efficiency when each uses a similar mechanism.

We do not suggest that catalytic antibodies will prove to be as efficient as all enzymes. However, a catalytic antibody can approximate the turnover efficiency of a highly evolved natural enzyme that is central to energy metabolism in all living organisms. Fructose 1,6-diphosphate aldolase could be considered a special case in that a single amino acid plays such a key role in the catalytic mechanism. But, this apparent simplicity is deceptive in that the chemical nature of that amino acid must be tuned by its local environment. Structural and chemical studies of our catalytic antibodies suggest that the $pK_a$ of the central $\epsilon$-amino group of LysH93 is lowered by a hydrophobic environment that disfavors protonation and development of charge on the amino functionality. This points to the power of reactive immunization to select for a particular chemistry in the active site. In this case, selection of an antibody requires an active site lysine that is sufficiently nucleophilic to attack the carbonyl carbon and form a stable vinylogous amide. It should not be overlooked that the dynamics of water, key in this reaction and the aldol, are also programmed in this selection.

The antibody aldolases are efficient catalysts, yet have very broad scope. They catalyzes over 100 aldehyde-aldehyde, aldehyde-ketone and ketone-ketone aldol addition and/or condensation reactions. Some of these reactions, such as the construction of the Wieland-Miescher ketone, are central to the theory and practice of organic chemistry. They have played a role in the synthesis of structures as diverse as steroids and taxol. The broad substrate specificity of the antibody aldolases is a property shared by other catalytic antibodies prepared by reactive immunization and, as discussed above, is likely to be the result of the special ontogeny of antibodies induced by immunogens that form covalent bonds within the binding pocket during induction (FIG. 28). This is in contrast to what is observed in immunological selections based on transition state analogues that result in highly complementary binding pockets of limited scope (Wedemayer et al. *Science* 276, 1665 (1997)). Our X-ray crystallographic and biochemical studies support this contention in that the antibody contains a large binding pocket with a lysine located in a hydrophobic environment at its base. The binding pocket is expected to accommodate various substrates that are drawn into the pocket as a result of hydrophobic partitioning. Once in the binding pocket, the substrates encounter the highly reactive lysine nucleophile and collapse to the nucleophilic enamine. Likewise, the aldol acceptor can enter the pocket and so long as there are no prohibitive steric interactions participate in an aldol addition. Certainly, the large number of different reactions that the antibody aldolases catalyze would be compatible with this scheme.

Finally, because the aldolase catalytic antibodies are in many ways analogous to a complex enzyme that is generally essential to life, we may learn something about the evolution of metabolic enzymes. The answer to the question of how difficult it is to achieve complex catalytic function is key in furthering our notions of the origin of life. Essentially the process of reactive immunization switches the usual evolutionary cycle of variation and selection to one in which, for the most part, selection precedes variation. Our experiments imply that it is apparently relatively simple to move from binding of reactive materials to a complex catalytic function that is efficient enough to be selectable. Once natural selection begins to optimize that function, the protein becomes refined not only in carrying out the relevant chemical reaction but also in adapting its activity to a more complicated metabolic scheme such as glucose metabolism. Ultimately the process of adaptation would refine the scope of catalysis to a narrow context in which context-specific regulatory processes would operate. But prior to that narrowing, an enzyme of broad specificity could serve as the starting point for the evolution of a family of related enzymes. With the vantage point that the evolution of an efficient chemical mechanism is a primary driving force in enzyme evolution and a starting point for diversification of function, it is anticipated as well as observed that structurally different proteins may converge on an efficient and identical chemical mechanism based on their ability to appropriately functionalize an active site (Hester, et. al. and K. Pointek, *FEBS Lett.* 292, 237 (1991)).

It may be that an early defining event in the evolution of some enzymes was an interaction with reactive materials such as toxins in a process similar to the induction of these catalytic antibodies with a reactive immunogen. The chemical reactivity of the primordial stoichiometric protein could then serve as a template for the rapid evolution of diverse catalytic function. This would be facilitated by gene duplication events, allowing each enzyme copy to be free to diversify and become specifically optimized for a particular substrate. In terms of the many reactions described here, each one could be selectively optimized after a gene duplication event.

EXAMPLE 3

Enantioselective Total Synthesis of Some Brevicomins Using Aldolase Antibody 38C2

One major goal in chemistry is the development of efficient catalysts for enantioselective processes. Although a number of powerful catalysts for functional group transformations like redox reactions have been developed in the last two decades, far fewer examples of enantioselective C—C-bond forming catalysts of general use are known (a) Noyori, *Asymmetric Catalysis in Organic Synthesis,* Wiley-Interscience (1994); b) I. Ojima (ed), *Catalytic Asymmetric Synthesis,* VCH (1993)). In this regard, the catalytic enantioselective aldol reaction, which is arguably one of the most important C—C-bond forming reaction, constitutes a great challenge (For recent examples of catalytic enantioselective aldol reactions, see: a) Y. M. A. Yamada, N. Yoshikawa, H. Sasai, M. Shibasaki, *Angew. Chem.* 1997, 109, 1942–1944; *Angew. Chem. Int. Ed. Engl.* 1997, 36, 1871–1873; b) E. M. Carreira, W. Lee, R. A. Singer, *J. Am. Chem. Soc.* 1995, 117, 3649–3650, and references therein).

Using the process of reactive immunization, we recently developed aldolase antibody 38C2, which uses the enamine mechanism of natural occurring class I aldolases (Wagner, R. A. Lerner, C. F. Barbas III, *Science*. 270, 1797, 1995). We have shown that, in contrast to its natural enzyme counterparts, and indeed most catalytic antibodies, this antibody aldolase accepts a wide variety of substrates (Barbas III et al. *Science* 1997, 278, 2085–2092). Antibody 38C2 has been shown to be useful in organic synthesis as demonstrated by the highly enantioselective synthesis of the Wieland-Miescher ketone on a preparative scale (Zhong et al. *J. Am. Chem. Soc.* 1997, 119, 8131–8132). While an antibody has been used previously in a total synthesis of (−)-α-multistriatin (Sinha, E. Keinan, *J. Am. Chem. Soc.* 1995, 117, 3653–3654) most catalytic antibodies reported to date have lacked the synthetic scope required of a generally useful catalyst. Here we report highly enantioselective total syntheses of (−)-(1R)-1-Hydroxy-exo-brevicomin (ent-6000) and (−)-(1S)-1-Hydroxy-exo-brevicomin (ent-5000) as well as formal total syntheses of eight different other brevicomins utilizing this antibody catalyst. The key steps are achieved using either an antibody catalyzed aldol addition or retro-aldol reaction.

Derivatives of the 6,8-dioxabicyclo[3.2.1]octanes (FIG. 34) are pheromones of a variety of bark beetle species (Silverstein, R. G. Brownlee, T. E. Bellas, D. L. Wood, L. E. Browne, *Science,* 1968, 159, 889). Extensive outbreaks of bark beetles may result in the destruction of millions of trees per year causing great ecological and economic damage. (+)-Exo-brevicomin (7-ethyl-5-methyl-6,8-dioxabicyclo [3.2.1]octan, (1000), was the first member of this pheromone family to be identified. Several oxygenated exo-brevicomins have been isolated and synthesized recently (Prestwich, *Pure Appl. Chem.* 1989, 61, 551–554; b) W. Francke, F. Schroeder, P. Philipp, H. Meyer, V. Shinnwell, G. Gries, *Bioorg. Med. Chem.* 1996, 4, 363–374; c) H. Takikawa, K.-i. Shimbo, K. Mori, *Liebigs Ann.* 1997, 821–824; d) Y. Yokoyama, K. Mori, *Liebigs Ann.* 1997, 845–849. Exo-brevicomin 1000 has been synthesized using an aldolase enzyme (rabbit muscle aldolase). However, this natural aldolase is restricted to dihydroxyacetone phosphate as the donor. This limitation requires the subsequent enzymatic removal of the phosphate group. M. Schultz, H. Waldmann, W. Vogt, H. Kunz, *Tetrahedron Lett.* 1990, 31, 867–868).

(+)-1-Hydroxy-exo-brevicomin and (+)-2-hydroxy-exo-brevicomin have been identified in the volatiles of the male mountain pine beetle, *Dentroctonus brevicomis*. Since its discovery in 1989 and structural elucidation in 1996, 1-hydroxy-exo-brevicomin has been synthesized twice. The first synthesis by Francke et al. was based on a kinetic resolution via Sharpless asymmetric epoxidation. The second by Mori et al. used the Sharpless asymmetric dihydroxylation as the key step. Using this methodology, they have also reported the synthesis of the (+)-2-hydroxy-exo-brevicomins as shown in FIG. 34.

We have previously demonstrated that 38C2 catalyzed aldol reactions with hydroxyacetone as donor lead to the highly regio- and stereoselective formation of α,β-dihydroxyketone s with an (2R,3S)-configuration. Further, unlike any of the transition metal catalyst reported to date, these antibodies also efficiently catalyze the retro-aldol reaction. Kinetic resolution with these catalysts results in the s elective destruction of the α(2R,3S)-aldol allowing for the recovery of the β(2S,3R)-aldol in high enantiomeric excess. By using both the aldol addition and retro-aldol activities, both aldol enantiomers may be prepared using the same antibody catalyst (as shown in FIG. 35).

Results and Discussion

Antibody 38C2 catalyzes the aldol reaction between aldehyde 7000 and hydroxyacetone on a preparative scale to give diol 8000 in 55% yield and 98% ee along with the anti-diastereomer (ratio 4:1; Aldehyde 7000 was prepared in two steps from commercial 5-oxohexanenitril. On an analytical scale, the ee was even higher (>99%). Dihydroxyketone 8000α was reduced with sodium borohydride to give triols syn-9000 and anti-9000 after HPLC saparation. Acid catalyzed deprotection and cyclization of the individual triols afforded hydroxybrevicomins ent-5000 and ent-6000 in essentially enantiomeric pure form. (FIG. 36)

The ee of dihydroxyketone 8000α was determined by chiral HPLC analysis using a chiracell AD column. Its absolute configuration was assigned by comparison with synthetic reference samples prepared from aldehyde 7000 via a Horner-Wadsworth-Emmons reaction followed by a Sharpless asymmetric dihydroxylation using either AD mix-α or Ad mix-β; Mulzer et al. *Tetrahedron Lett.* 1994, 35, 9021–9024; Walsh, K. B. Sharpless, *Synlett* 1993, 605–606. (FIG. 37)

Antibody 38C2 catalyzed retro-aldol reaction of racemic 8000 gave diol 8000β in >99% ee after 52% conversion of the racemate, through a kinetic resolution. Thus, hydroxybrevicomins 5000 and 6000 can be obtained from 8000β by a route analogous to that described in FIG. 38.

2-Hydroxylated brevicomins 3000 and 4000 were prepared from dihydroxyketone 11000α using a strategy similar to that described for copounds 5000 and 6000. Antibody 38C2 catalyzed the aldol reaction between aldehyde 10000 and 1-hydroxy-2-butanone to give 11000α in >99% ee (Aldehyde 10000 was prepared in two steps from commercial ethyl levulinate). Again the enantiomers (ent-3000 and ent-4000) could be prepared via kinetic resolution of aldol rac-syn-11000 to give 11000β in >99% ee after 54% conversion. 2-Hydroxy-exo-brevicomin 4000 is a new compound which has not been reported previously. We suggest that it may be a natural product derived from endo-brevicomin 2000 by oxygenation. This is supported by the fact that exo-brevicomin 1000 is the precursor in the biosynthesis of hydroxy-brevicomin 3000. The synthesis of exo-brevicomin 1000 from 3 has already been reported (Taniguchi, H. Ohnishi, K. Ogasawara, *Chem. Commun.* 1996, 1477–1478). Thus, both enantiomers of exo-brevicomin 1 are accessible now. (FIG. 38)

The kinetic parameters of all antibody catalyzed reactions are shown in FIG. 39.

In summary we have demonstrated highly enantioselective total syntheses of brevicomins ent-5000 and ent-6000, and formal total syntheses of eight other brevicomins (5000, 6000, 3000, ent-3000, 4000, ent-4000, 1000, ent-1000) utilizing a single antibody catalyst. For the first time, a catalytic antibody has been used to decrease the total number of synthetic steps and to increase the enantioselectivity of natural product syntheses. These results underscore the power of reactive immunization to generate antibody catalysts that are both, efficient and broad in scope.

EXAMPLE 4
A Short Enantioselective Synthesis of 1-Deoxy-L-xylulose by Antibody Catalysis A new efficient synthesis of 1-deoxy-L-xylulose (1111) is presented. The key step is achieved by a highly enantioselective aldol addition of hydroxyacetone to benzyloxyacetaldehyde via antibody catalysis. The synthesis described here should provide a convenient route to isotopically labeled derivatives.

The increased attention in the literature recently given to 1-deoxyxylulose has prompted us to report our results concerning the synthesis of this important carbohydrate. This carbohydrate was first isolated from Streptomyces hygroscopicuus in 1976 (Slechta et al. *J. Antibiot.* 1976, 29, 685; Hoeksema, H.; Baczynskyj, L. *J. Antibiot.* 1976, 29, 688). 1-Deoxy-D-xylulose has been found to be an intermediate in the biosynthesis of thiamin (vitamin B1) and pyridoxal (vitamin B6). Both L- and D- enantiomers are synthesized by a wide range of microorganisms from pyruvic acid and L- or D-glyceraldehyde, respectively. Recently this sugar has been found to be an alternate non-mevalonate biosynthetic precursor to terpenoid building blocks.

Several syntheses of both enantiomers of 1-deoxyxylulose have been reported to date, including one involving isotopic labeling. Some of these are multi-step syntheses with low overall yields. Here we report a new highly efficient enantioselective synthesis of 1-deoxy-L-xylulose utilizing the commercially available aldolase antibody 38C2. This antibody catalyzes over 200 different aldol and retro-aldol reactions, usually with excellent enantioselectivities (Wagner, J.; Lerner, R. A.; Barbas III, C. F. *Science* 1995, 270, 1797; (b) Barbas III, C. F.; Heine, A.; Zhong, G.; Hoffmann, T.; Gramatikova, S.; Björnestedt, R.; List, B.; Anderson, J.; Stura, E. A.; Wilson, E. A.; Lerner, R. A. *Science* 1997, 278, 2085–2092; (c) Hoffmann, T.; Zhong, G.; List, B.; Shabat, D.; Anderson, J.; Gramatikova, S.; Lerner, R. A; Barbas III, C. F. *J. Am. Chem. Soc.* 1998, 120, 2768; (d) Zhong, G. F.; Shabat, D.; List, B.; Anderson, J.; Sinha, S. C.; Lerner, R. A.; Barbas III, C. F. *Angew. Chem.* 1998, 37, 2481–4; (e) List, B.; Shabat, D.; Barbas III, C. F.; Lerner, R. A. *Chem. Eur. J.* 1998, 4, 881–5).

Hydroxyacetone is one of the best aldol donors for antibody 38C2. This is remarkable in the context that no other catalyst, chemical or biological, is capable of using hydroxyacetone as a donor substrate for the aldol reaction. As a general rule we found that hydroxyacetone reacts with different aldehydes, highly regio-, diastereo-, and enantioselectively, to give the corresponding α-(2R,3S)-dihydroxy ketones. The corresponding β-(2S,3R)-isomer can be obtained from the racemic mixture via 38C2 catalyzed enantioselective retro-aldol reaction (FIG. 40). This strategy has been successfully demonstrated with the kinetic resolution of many aldols and in the total synthesis of ten different brevicomins.

Antibody 38C2 catalyzed aldol addition of hydroxyacetone to commercially available benzyloxyacetaldehyde afforded α,β-dihydroxyketone 2111a in 32% isolated yield. This reaction used very low catalyst loading, 0.04 mol %, and was worked up after conversion of 56% of the aldehyde. The reaction rate had slowed at this point, probably because of minor oxidation of 2111a to the corresponding 1,3-diketone. β-Diketones bind to the active site lysine of the antibody and react to form enaminones, potently inhibiting the catalyst. As observed in earlier cases, some amount of the anti diastereomer was formed. In this case only 7% of the undesired anti product was observed, however silica gel chromatography furnished the pure product. Ketone 2111a was easily transformed to 1-deoxy-L-xylulose (1111) by hydrogenation (FIG. 41) Benzyloxyacetaldehyde (80 mg, 0.53 mmol)in)in) 0.5 mL of acetonitrile, was added to 9 mL of a solution of antibody 38C2 (35 mg, 0.23 mmol) in PBS (phosphate buffer saline, 100 mM), followed by the addition of of hydroxyacetone. (0.5 mL, 6.3 mmol). After 48 hr at room temperature the reaction reached 56% conversion and the mixture was freeze dried. The remaining residue was extracted with methylene chloride. The solvent was removed under reduced pressure and the crude product was purified by column chromatography (silica gel, ethyl acetate/hexane, 1/1) to give pure 2111a (39 mg, 0.17 mmol, 32%) in 97% ee. Benzyl ether 2111a (39 mg, 0.17 mmol) was dissolved in 1 mL of methanol and hydrogenated with a catalytic amount of palladium hydroxide on carbon. After two hr, the mixture was filtered through celite and the solvent was removed under reduced pressure to give pure 1-deoxy-L-xylulose (19 mg, 0.14 mmol, 81%).

In order to determine the enantiomeric purity of the aldol product, we synthesized reference compounds as shown in FIG. 42. Horner-Wadsworth-Emmons reaction of diethyl-2-oxopropyl-phosphonate with benzyloxyacetaldehyde gave the known olefin 3111 which was dihydroxylated according to the Sharpless procedure to give reference aldols 2111a and 2111b in high ee's (Walsh, P. J.; Sharpless, K. B. Synlett 1993, 605–610; Mulzer, J.; List, B. *Tetrahedron Lett.* 1994, 35, 9021–4). Sharpless AD reactions were purposely performed under suboptimal conditions, the reaction was performed at room temperature, in order to use the small fraction of the undesired enantiomer formed under these conditions as a chromatographic standard.

The enantiomeric excess of dihydroxyketone 2111a was determined by chiral HPLC analysis using a chiracell AD column and found to be 97% ee (FIG. 43). Absolute configuration was assigned by comparison with authentic samples from Sharpless AD.

In conclusion we have shown here a new synthesis of 1-deoxy-L-xylulose. This two step synthesis is the shortest reported to date. The key step has been achieved through a highly diastereo- and enantioselective antibody catalyzed aldol reaction using hydroxyacetone as aldol donor. Antibody 38C2 (commercially available from Aldrich) is the only known catalyst that can catalyze the aldol addition of unprotected hydroxyacetone to an aldehyde. The preparation of isotopically labeled 1-deoxyxyluloses, required for further biological studies, can easily be envisioned by using our synthetic methodology and labeled benzyloxyacetaldehyde and/or hydroxyacetone (Piel et al. *Tetrahedron Lett.* 1997, 38, 6387).

Methods for producing catalytic antibodies with aldolase activity are disclosed in U.S. Pat. Nos. 5,571,681 and 5,733,757, incorporated herein by reference.

While a preferred form of the invention has been shown in the drawings and described, since variations in the preferred form will be apparent to those skilled in the art, the invention should not be construed as limited to the specific form shown and described, but instead is as set forth below in the claims.

Synthetic Protocals

General

$^1$HNMR spectra were recorded on a Bruker AMX-500 NMR spectrometer. Mass spectra were recorded on an API III PE Sciex triple-quadrupole mass spectrometer. All reactions requiring anhydrous conditions were performed in oven-dried glassware under an Ar or $N_2$ atmosphere. Chemicals and solvents were either puriss p.A. or purified by standard techniques. THF was distilled from sodium-benzophenone. Thin layer chromatography (TLC): silicagel plates Merck 60 $F_{254}$, compounds were visualized by irradiation with UV light and/or by treatment with a solution of 25 g phosphomolybdic acid, 10 g $Ce(SO_4)_2 \cdot H_2O$, 60 ml concd. $H_2SO_4$ and 940 ml $H_2O$ followed by heating and/or by staining with a solution of 12 g 2,4-dinitrophenylhydrazine in 60 mL concd. $H_2SO_4$, 80 mL $H_2O$ and 200 mL 95% EtOH followed by heating and/or by immersing in an iodine bath (30 g $I_2$, 2 g KI, in 400 ml EtOH/$H_2O$ 1:1) and warming.—Flash chromatography (FC): silica gel Merck 60 (particle size 0.040–0.063 mm), eluent given in parentheses.—¹H NMR: Bruker AMX 300, Bruker AMX 250. The chemical shifts are given in d relative to TMS (d=0 ppm), the coupling constants J are given in Hz. The spectra were recorded in CDCl₃ as solvent at room temperature unless stated otherwise.—HR-MS: liquid secondary ionization (LSI-MS): VG ZAB-ZSE with 3-nitrobenzyl alcohol matrix.

Antibody Stability

The antibodies 38C2 and 33F12 are stable at room temperature for weeks dissolved in different buffer solutions (pH 5.5 to 8.5) and even pure water. They can be lyophilized and passed over a Sephadex column with less than 5% activity loss. No detectable activity loss was found if the antibodies were stored in stock solutions of 10 to 20 mg/ml in phosphate buffered saline (PBS) (10 mM phosphate, 150 mM NaCl, pH 7.4) at −78° C.

Preparation of 4-(4'-Acetamidophenyl)
butyraldehyde (6) as shown in FIG. 1

Aldehyde 6 was prepared in 4 steps starting from commercially available 4-(4'-aminophenyl)butyric acid as follows.

(I) 4-(4'-Acetamidophenyl)butyric acid. 4-(4'-Aminophenyl)butyric acid (4.0 g, 22 mmol) was added to 150 mL mixed solvent of acetonitrile and water (9/1). Acetic anhydride (7.4 g, 55 mmol, 2.5 eq) was added at 0 (C. Then the reaction mixture was stirred at room temperature for 4 h. The filtration of the reaction mixture was followed by drying at 120 (C overnight to give 4.53 g of 4-(4'-acetamidophenyl)butyric acid (93%). HR-MS: 222.1140; C12H16O3N+ (calcd 222.1130); C12H15O3N (221.26).

(ii) 4-(4'-acetamidophenyl)butyric acid methyl ester. 4-(4'-Acetamidophenyl)butyric acid (4.50 g, 20 mmol) and potassium carbonate (2.90 g, 21 mmol) were added to 20 mL of dry DMF. The reaction mixture was stirred at room temperature for 15 min. Then methyl iodide (14.2 g, 0.10 mol) was added under nitrogen. The reaction mixture was stirred at room temperature overnight. After evaporation of the solvent and methyl iodide, a solid mixture was obtained, from which the methyl ester was isolated by extraction with ethyl acetate (3×70 mL) to 4.7 g (>99%). 1H NMR (300 MHz, CDCl3): (7.41 (d, J 8.4, 2 H), 7.34 (s, br, 1 H), 7.12 (d, J 8.4, 2 H), 3.67 (s, 3 H), 2.61 (t, J 7.3, 2 H), 2.32 (t, J 7.3, 2 H), 2.17 (s, 3 H), 1.93 (hept, J 7.3, 2 H); HR-MS: 236.1296; C13H18O2N+ (calcd 236.1287); C13H17O3N (235.28).

(iii) 4-(4'-Acetamidophenyl)butanol. 4-(4'-Acetamidophenyl)butyric acid methyl ester (4.70 g, 20 mmol) was dissolved in 50 mL of dry THF and DIBALH in methylene chloride (1.0 M, 40 mL) was dropwise added at −30° C. The mixture was kept stirring at this temperature for 3 h. Saturated ammonium chloride (25 mL) was added slowly. Extraction with 3×80 mL of ethyl acetate followed by evaporation of the solvent gave a residue which was purified by FC (hexane/ethyl acetate 4:1) to give 2.73 g (66%) of 4-(4'-acetamidophenyl)butanol. 1H NMR (300 MHz, CDCl3): (7.42 (d, J 8.4, 2 H), 7.23 (s, br, 1 H), 7.13 (d, J 8.4, 2 H), 3.71 (t, J 7.2, 2 H), 2.56 (t, J 7.2, 2 H), 2.17 (s, 3 H), 1.65 (m, 4 H); HR-MS: 208.1342; C12H18O2N+ (calcd 208.1338); C12H17O2N (207.27).

(iv) 4-(4'-Acetamidophenyl)butyraldehyde (6). A mixture of methylene chloride (25 mL) and oxalyl chloride (1.0 mL, 11 mmol) were placed in a flask. Dimethyl sulfoxide (1.7 mL, 22 mmol) diluted with methylene chloride (5 mL) was added to the stirred solution at −78° C. The reaction mixture was stirred for 2 min and 4-(4'-acetamidophenyl)butanol (2.2 9, 10 mmol) in 10 mL of methylene chloride was added within 5 min. The stirring was continued for additional 15 min. Triethylamine (7.0 mL, 50 mmol) was added and the reaction mixture was stirred for 5 min and then allowed to warm to room temperature. Water (50 mL) was added and the aqueous layer was reextracted with methylene chloride (50 mL). The organic layers were combined, washed with saturated sodium chloride solution (100 mL), and dried with magnesium sulfate. After concentration 2.07 g (94%) of pure 4-(4'-acetamidophenyl)butyraldehyde (6) was obtained by FC (hexane/ethyl acetate 3:1). 1H NMR (300 MHz, CDCl3): (9.76 (s, br, 1 H), 7.42 (d, J 8.4, 2 H), 7.23 (s, br, 1 H), 7.13 (d, J 8.4, 2 H), 2.63 (t, J 7.2, 2 H), 2.45 (t, J 7.2, 2 H), 2.17 (s, 3 H), 1.94 (hept, J 7.2, 2 H); HR-MS: 206.1185; C12H16O2N+ (calcd 206.1181); C12H15O2N (205.26).

General Procedure for the chemical preparation of
Aldol Products as shown on FIGS. 10, 11, 13, 15,
16, and 18

The corresponding ketone (1.0 mmol; some of the preferred aldehydes disclosed in FIG. 14 obtained commercially via Aldrich, Sigma, Fluka, etc. or as described herein) was added to a freshly prepared solution of LDA (1.05 mmol) in 2 mL of THF at −78° C. After stirring at this temperature for 30 min, the appropriate aldehyde (1.0 mmol; some of the preferred aldehydes disclosed in FIG. 1 and FIGS. 10, 11, 13, 15, 16, and 18; obtained commercially via Aldrich, Sigma, Fluka, etc. or as described herein), dissolved in 2 mL of THF, was added over a period of 1 min. After stirring for 5–30 min at −78° C., saturated NH4Cl solution (1 mL) was added and the reaction mixture was allowed to warm to room temperature. The product was extracted with ethyl acetate (3×10 mL), dried (MgSO4) and evaporated. The pure aldol products were obtained by FC. Spectroscopic data for the acetone addition products with aldehydes 3–8 and 48 are given below as examples.

6-(4'-Acetamidophenyl)-4-hydroxy-2-hexanone (9)

Synthesized according to the above procedure using the indicated aldehyde and ketone provided in the Figures and obtained commercially or as described herein. FC (ethyl acetate/hexane 75:25) gave 0.21 g (85%) of pure aldol 9. 1H NMR (300 MHz, CDCl3): (8.12 (s, br, 1 H), 7.37 (d, J 8.4, 2 H), 7.06 (d, J 8.4, 2 H), 4.01 (m, 1 H), 3.42 (m, 1 H), 2.71 (m, 1 H), 2.62 (m, 3 H), 2.13 (s, 3 H), 2.10 (s, 3 H), 1.75 (m, 1 H), 1.64 (m, 1 H); HR-MS: 250.1450; C14H20O3N+ (calcd 250.1443); C14H19O3N (249.31).

4-(4'-Acetamidophenyl)-4-hydroxy-2-butanone (18)

Synthesized according to the above procedure using the indicated aldehyde and ketone provided in the Figures and obtained commercially or as described herein. FC (ethyl acetate/hexane 70:30) gave 0.18 g (82%) of pure aldol 18. 1H NMR (250 MHz, DMSO-d6): (9.88 (s, 1 H), 7.49 (d, J 8.5, 2 H), 7.24 (d, J 8.5, 2 H), 5.28 (d, J 4.4, 1 H), 4.91 (m, 1 H), 2.65 (m, 2 H), 2.09 (s, 3 H), 2.01 (s, 1 H); HR-MS: 244.0955; C12H15O3NNa+ (calcd 244.0949); C12H15O3N (221.26).

4-(4'-Isobutyramidophenyl)-4-hydroxy-2-butanone (59)

Synthesized according to the above procedure using the indicated aldehyde and ketone provided in the Figures and obtained commercially or as described herein. FC (ethyl acetate/hexane 40:60) gave 0.23 g (91%) of pure aldol 59. 1H NMR (250 MHz, CDCl3): (7.50 (d, J 8.5, 2 H), 7.30 (d, J 8.5, 2 H), 7.27 (s, br, 1 H), 5.12 (m, 1 H), 3.36 (s, 1 H), 2.84 (m, 2 H), 2.51 (pent, J 6.8, 1H), 2.20 (s, 3 H), 1.25 (d, J 6.8, 6 H); HR-MS: 272.1267; C14H19O3NNa+ (calcd 272.1263); C14H19O3N (249.31).

6-(4'-Acetamidophenyl)-4-hydroxy-5-methyl-2-hexanone (21)

Synthesized according to the above procedure using the indicated aldehyde and ketone provided in the Figures and obtained commercially or as described herein. FC (ethyl acetate/hexane 70:30) gave 0.21 g (79%) of pure aldol 21. 1H NMR (300 MHz, CDCl3): (7.85 (s, br, 1 H), 7.39 (d, J 8.3, 2 H), 7.07 (d, J 8.3, 2 H), 3.95 (m, 1 H), 3.08 (m, 1 H), 2.82 (m, 1 H), 2.66 (m, 3 H), 2.55 (m, 1 H), 2.37 (m, 1 H), 2.18 (s, 3 H), 2.15 (s, 3 H), 1.76 (m, 1 H), 0.85 (d, J 6.6, 3 H); HR-MS: 264.1608; C15H22O3N+ (calcd 264.1600); C15H21O3N (263.34).

7-(4'-Acetamidophenyl)-4-hydroxy-2-heptanone (24)

Synthesized according to the above procedure using the indicated aldehyde and ketone provided in the Figures and obtained commercially or as described herein. FC (ethyl acetate/hexane 70:30) gave 0.23 g (89%) of pure aldol 24. 1H NMR (300 MHz, CDCl3): (7.39 (d, J 8.4, 2 H), 7.24 (s, br, 1 H), 7.13 (d, J 8.4, 2 H), 4.05 (m, 1 H), 3.04 (m, 1 H), 2.57 (m, 4 H), 2.17 (s, 3 H), 2.16 (s, 3 H), 1.70 (m, 2 H), 1.45 (m, 2 H); HR-MS: 286.1411; C15H21O3NNa+ (calcd 286.1419); C15H21O3N (263.34).

4-(4'-Nitrophenyl)-4-hydroxy-2-butanone (27)

Synthesized according to the above procedure using the indicated aldehyde and ketone provided in the Figures and obtained commercially or as described herein. FC (ethyl acetate/hexane 50:50) gave 0.18 g (86%) of pure aldol 27. 1H NMR (250 MHz, CDCl3): (8.21 (d, J 7.2, 2 H), 7.52 (d, J 7.2, 2 H), 5.25 (m, 1 H), 3.56 (d, J 3.2, 1 H), 2.83 (m, 2 H), 2.21 (s, 1 H); HR-MS: 232.0591; C10H11O4NNa+ (calcd 232.0586); C10H11O4N (209.20).

6-(4'-Nitrophenyl)-4-hydroxy-5-hexen-2-one (30)

Synthesized according to the above procedure using the indicated aldehyde and ketone provided in the Figures and obtained commercially or as described herein. FC (ethyl acetate/hexane 50:50) gave 0.21 g (89%) of pure aldol 30. 1H NMR (250 MHz, CDCl3): (8.15 (d, J 7.3, 2 H), 7.46 (d, J 7.3, 2 H), 6.71 (d, J 15.9, 1 H), 6.35 (dd, J 15.9, J 5.3, 1 H) 4.78 (m, 1 H), 3.28 (d, J 3.7, 1 H), 2.73 (m, 2 H), 2.21 (s, 1 H); HR-MS: 258.0751; C12H13O4NNa+ (calcd 258.0742); C12H13O4N (235.24).

4-Hydroxynona-5,7-dien-2-one (49)

Synthesized according to the above procedure using the indicated aldehyde and ketone provided in the Figures and obtained commercially or as described herein. FC (ethyl acetate/hexane 15:85) gave 88 mg (57%) of pure aldol 49. 1H NMR (300 MHz, CDCl3): (6.21 (m, 1 H), 6.05 (m, 1 H), 5.74 (m, 1 H), 5.54 (m, 1 H), 4.56 (m, 1 H), 2.93 (m, 1 H), 2.62 (d, J 6.2, 2 H), 2.18 (s, 3 H), 1.75 (d, J 6.5, 3 H); HR-MS: 177.0899; C9H14O2Na+ (calcd 177.0892); C9H14O2 (154.21).

Antibody Catalysis
General Preparative Antibody Catalyzed Reactions

Representative example for the Antibody Catalyzed Reactions as shown on FIGS. 10, 11, 13, 15, 16, and 18 for the preparation of (S) 4-hydroxy-6-(4-nitrophenyl)-5-hexen-2-one (30) as shown in FIG. 15

To a solution of 4-nitrocinnamaldehyde 8 (110 mg, 0.61 mmol; alternatively other aldehyde acceptors are shown in the Figures and can be obtained commercially or as described herein) in 15 mL of DMF and 31 mL of acetone (alternatively other ketone donors are shown in the Figures and can be obtained commercially or as described herein), PBS buffer (571 mL, degassed and kept under argon) was added slowly to avoid precipitation. Antibody 38C2 (8.0 mL of a 120 mM solution) was added. The final concentrations of 4-nitrocinnamaldehyde and Ab38C2 were 1.0 mM and 1.9 mM, respectively in a total volume of 625 mL containing 5% (v/v) of acetone. The reaction mixture was kept in a dark place at room temperature for seven days under Argon. The reaction mixture was saturated with sodium chloride and extracted with 3×150 mL of ethyl acetate. The extracts were dried over MgSO4 and evaporated to yield 140 mg of crude product. Purification by FC (1:2, ethyl acetate/hexane) gave 96 mg (67%) of pure aldol product (30) with an ee of 91%.

EXAMPLE 2

Representative example for the Antibody Catalyzed Reactions as shown on FIG. 11 for Enantioselective preparation of fluorinated aldols A solution of 3-(4'-acetamidophenyl)propanal 4 (15 mg, 0.078 mmol alternatively other aldehyde acceptors are shown in the Figures and can be obtained commercially or as described herein) in 0.2 mL of DMF, 0.5 mL of fluoroacetone (alternatively other ketone donors are shown in the Figures and can be obtained commercially or as described herein) and 8.0 mL of PBS buffer was added to Ab38C2 (1.5 mL of a 120 mM solution). The final concentrations of 3-(4'-acetamidophenyl)propanal and Ab38C2 were 7.6 mM and 17.5 mM, respectively in a total volume of 10.2 mL containing 5% (v/v) of fluoroacetone. The reaction mixture was kept at room temperature for 21 days. Three aldol products syn-16 (ee 95 %), anti-16 (ee 34%) and 60 (ee 97%) (FIG. 11) were isolated by semi-preparative RP-HPLC (Column: VYDAC protein & peptide C18, (=254 nm, 12% CH3CN/88% water with 0.1% TFA, 4.0 mL/min, 1.0 mL reaction mixture/injection) to give syn-16 (12 mg, tR=20.8 min, yield 61%), anti-16 (3.6 mg, tR=18.2 min, yield 21%), and 60 (1.2 mg, tR=16.3 min, yield 7%). The overall yield was 82% (15% of aldehyde 4 was recovered).

Syn-isomer of 6-(4'acetamidophenyl)-3-fluoro-4-hydroxy-2-hexanone (syn-16)

Synthesized according to the above procedure using the indicated aldehyde and ketone provided in the Figures and obtained commercially or as described herein 1H NMR (300 MHz, CDCl3): (7.41 (d, J 8.4, 2 H), 7.22 (s, br, 1 H), 7.15 (d, J 8.4, 2 H), 4.62 (dd, J 48.8, 4.9, 2 H), 3.97 (m, 1 H), 2.85 (m, 1 H), 2.67 (m, 1 H), 2.30 (d, J 5.1, 3 H), 2.18 (s, 3 H), 1.84 (m, 2 H)

Anti-isomer of 6-(4'acetamidophenyl)-3-fluoro-4-hydroxy-2-hexanone (anti-16)

Synthesized according to the above procedure using the indicated aldehyde and ketone provided in the Figures and obtained commercially or as described herein 1H NMR (300 MHz, CDCl3): (7.42 (d, J 8.4, 2 H), 7.17 (s, br, 1 H), 7.16 (d, J 8.4, 2 H), 4.64 (dd, J 48.9, 2.4, 1 H), 4.00 (dm, J 24.5, 1 H), 2.77 (m, 2 H), 2.31 (d, J 5.0, 3 H), 2.18 (s, 3 H), 1.94 (m, 2 H).

Regio-isomer, 6-(4'acetamidophenyl)-1-fluoro-4-hydroxy-2-hexanone (60)

1H NMR (300 MHz, CDCl3): Synthesized according to the above procedure using the indicated aldehyde and ketone provided in the Figures and obtained commercially or as described herein (7.43 (d, J 8.4, 2 H), 7.17 (d, J 8.4, 2 H), 7.14 (s, br, 1 H), 4.83 (d, J 47.5, 2 H), 4.12 (m, 1 H), 2.73 (m, 4 H), 2.18 (s, 3 H), 1.81 (m, 2 H).

Representative example for the products shown on FIG. 15 for the preparative scale synthesis of 2-[1'-(4"-isobutyramidophenyl),1'-hydroxy] methylcyclopentanone (19) as shown in FIG. 15

Cyclopentanone (1 mol, 88 mL alternatively other ketone donors are shown in the Figures and can be obtained commercially or as described herein) was dissolved in 912 mL of MOPS buffer (100 mM, pH=7.4). Next, Ab38C2 (1.3 mmol, 0.1 g) was added and the first addition of aldehyde, 4-isobutyramidobenzyaldehyde (1.1 mmol, 213 mg alternatively other aldehyde acceptors are shown in the Figures and can be obtained commercially or as described herein) was made. The reaction was stirred for 24 hrs followed by a second addition of aldehyde. Two subsequent additions of aldehyde followed at 24 hr time periods for a total of 852 mg, 4.4 mmol. The reaction progress was monitored by HPLC (Hitachi HPLC system: pump L-7100, UV detector L-7400 and integrator D-7500) using a Rainin column (Microsorb-MV, C18, 300 Å, 5 mm; 250×4.6 mm) and acetonitrile/water mixture(20% CH3CN/80% water containing 0.1% trifluoroacetic acid) with a flow rate of 1.0 mL/min. The reaction mixture was kept in a dark place at room temperature for 21 days under Argon. The reaction mixture was then saturated with NaCl. The mixture was extracted with 3×500 mL of ethyl acetate, dried over MgSO4, and evaporated to yield 1.4 g of crude product. Purification by FC (60:40, EtAc/Hex.) gave 0.9 g (72%) of pure product. (19) with a de of >95%. 1H NMR (300 MHz, CDCl3): (7.49 (d, J 8.4, 2 H), 7.31 (s, br, 1 H), 7.27 (d, J 8.4, 2 H), 5.24 (s, 1 H), 4.62 (m, 1 H), 2.6–1.6 (m, 7 H), 1.26 (d, J 6.8, 6 H).

Antibody Assays

All antibody catalyzed reactions were performed in phosphate buffered saline (10 mM phosphate, 150 mM NaCl, pH 7.4) except of reactions with substrate 43 (Scheme 4, H2O, pH 6.5) and substrates n-C4H9CHO, n-C5H11CHO, n-C6H13CHO (Table 6, (3-[N-Morpholino]propanesulfonic acid) sodium salt buffer (MOPS buffer), pH 7.0). All antibody catalyzed reactions and background reactions with substrates 3–8, 33, 37, 39, 41, 43, 45 and 48 were monitored by high pressure liquid chromatography (HPLC; Hitachi HPLC system (pump L-7100, UV detector L-7400 and integrator D-7500) using a Rainin column (Microsorb-MV, C18, 300 Å, 5 mm; 250×4.6 mm) and acetonitrile/water mixtures (containing 0.1% trifluoroacetic acid) as eluents at a flow rate of 1.5 mL/min or 1.0 mL/min. Formation of products 51–53 was followed by gas chromatography (DB-5, J&W Scientific, length: 30 m, I.D.: 0.32 mm, Temp.: 65° C. (2 min), rate: 10° C./min, tR: (51-anti)=13.82 min, (51-syn)=14.05 min; (52-anti)=12.56 min, (52-syn)=12.82 min; (53-anti)=11.24 min, (53-syn)=11.52 min)

Specific Rates of Cross-Aldol Reactions

The specific rates of cross-aldol reactions were determined before 10% completion of the reactions using initial concentrations of the acceptor substrate (500 mM), antibody (2 mM) and donor ketone (1.0 M).

Specific Rates of Self-Aldol and Intramolecular Aldol Reactions

The specific rates of self-aldol and intramolecular aldol reactions were determined before 10% completion of the reactions using initial concentrations of the substrate (0.10 M) and antibody (5 mM).

Michaelis-Menten Kinetics

Product formation or percent conversion of antibody catalyzed reaction mixtures was monitored by HPLC or GC. The experimental data was plotted using nonlinear regression analysis with GraFit software to give kcat and KM of the reactions. All data are reported per antibody active site. An IgG antibody possesses 2 active site per MW of ~150,000 g/mol.

Determination of Enantiomeric Excess of Products 9, 18, 59, 21, 24, 27, 30 and 54

To a 6.25 mM solution of the aldehyde in 160 mL of PBS were added 10 mL of acetone and 30 mL of a 135 mM solution of the antibody in PBS. The final concentrations were 5 mM of aldehyde and 20 mM of antibody in a total volume of 200 mL of PBS containing 5% (v/v) of acetone. After 18 h, 12 mL of CH2Cl2 were added, the organic phase was dried (MgSO4) and evaporated. In case of products 9, 18, 59, 21, 24, 27 and 30 the residue was re-dissolved in ca. 1 mL of i-propanol and the ee was determined by normal phase HPLC using an appropriate Daicel column for enantiomer separation. The ee of product 54 was determined using GC on a chiral capillary column (Cyclodex-B, J&W Scientific, length: 30 m, I.D.: 0.25 mm, Temp.: 150° C., tR: (a)=15.48 min, (b)=16.01 min).

180 Incorporation

The electron spray ionization (ESI) mass spectrometry used to monitor 180 incorporation into 59 was performed on an API III Perkin Elmer SCIEX triple quadropole mass spectrometer. In preparation of the sample, lyophilized antibody 38C2 was resuspended in 180 labeled water (180, 95–98%, Cambridge Isotope Laboratories, Andover, Mass.) to give a final concentration of 7.5 mM. The reaction was started by addition of aldol product 59 (1.5 mM) and aliquots were taken out for analysis of 180 incorporation over time. Immediately before analysis the samples were diluted 10-fold in methanol.

Crystallization, data collection, structure solution and refinement

The Fab' of the aldolase antibody 33F12 crystallizes from 18% PEG 4000, 0.1 M HEPES, pH 7.4 and 10% isopropanol, in space group P2$_1$2$_1$2$_1$ with unit cell dimensions a=56.5 Å, b=65.3 Å, c=132.6 Å and one molecule in the asymmetric unit. A native data set was collected at the Stanford Synchrotron Radiation Laboratory, beamline 7-1, at a resolution of 2.15 Å, at −176(C using 25% glycerol as a cryoprotectant. Data were processed using DENZO and SCALEPACK (17). The structure was determined using molecular replacement techniques. From 86 initial search models, antibody NC6.8 (18) gave a rotation function solution using MERLOT (17) of 7.6 s in the resolution range 10–4 Å. A rotational and translational search using data from 15–4 Å in the program AMORE (17) gave an R-value of 44.7% with a correlation coefficient of 49.6, compared to the next, incorrect solution of R=55.6% and correlation coefficient of 19.4. Computational mutation to the correct sequence and multiple rounds of model building were carried out using the graphics program O. The initial refinement in XPLOR, using rigid body, positional and slowcooling refinement protocols, resulted in an R=23.8% for 10.0 to 2.15 Å data with F>1 s. Refinement was then continued with the program SHELXL-96. For each refinement step, at least 10 cycles of conjugate gradient minimization with individual B-value refinement were performed, with standard restraints on bond distances and angles, and a SIMU restraint of 0.08 for B-values. In the final stages, hydrogen atoms were placed in calculated positions without use of additional parameters. Water molecules were built into the difference electron density and refined if they made reasonable hydrogen bonding interactions. The overall map quality was good, showing no main chain breaks with the exception of a region H128-H136 in the constant heavy chain, as frequently observed in other antibodies. These residues were refined with fixed B-values and occupancies set to zero, since they had no interpretable density. The Ramachandran plot showed 90.2% of the residues in the most favoured region with the only outlier being residue $Val^{L51}$, as commenly observed for antibody Fab molecules. The density for $Lys^{H93}$ is very bulky at a 2 s level and doesn't extend beyond $Ce$, possibly indicating multiple side-chain conformations, as frequently observed for Lys. The residue was modeled in slightly different orientations, but always refined back to the same reported position. Final refinement parameters are outlined in FIG. 15.

Class I aldolase enzymes utilize an active site Lys for the formation of a covalent Schiff-base intermediate. The first step in the reaction is the nucleophilic attack of that Lys to form a carbinolamine with the substrate, assuming that the Lys is uncharged. In the x-ray crystal structure of the transaldolase B—intermediate complex, the relevant Lys is proposed to be charged, but deprotonation is facilitated by a nearby water molecule. The pKa of Lys in aqueous solution is usually around 10.5. In order to act as a strong nucleophile as required to catalyze the reactions described above, an uncharged amino group with a significantly perturbed pKa is necessary. Paetzel et al. outlined three fundamental conditions for pKa perturbation of Lys: electrostatics, polarity and hydrophobic microenvironment. Westheimer et al. demonstrated for acetoacetic acid decarboxylase that the pKa of the reactive Lys can be shifted to 5.6 due to the electrostatic repulsion effect of a second, positively-charged Lys residue nearby. On the other hand, the pKa of the Lys can be increased if there is close negative charge, since a positively charged Lys would be favoured for charge neutralization. The pKa of the catalytic Lys in orotidine monophosphate decarboxylase is reduced to 7 and is explained by the surrounding non-polar cavity in which it is located. Mutation studies within the hydrophobic core of T4 lysozyme have shown that the pKa of a Lys buried within a hydophobic pocket is shifted to 6.5.

The sequence of antibody Fab' 33F12 contains 26 Lys residues. Since it was generated by reactive immunization with a 1,3 dicarbonyl hapten, the selected antibody should have a Lys located in the binding pocket. In order to get a better structural understanding for the nucleophilic character of that Lys, we determined the three-dimensional x-ray structure by molecular replacement at 2.15 Å resolution. The overall structure of the native Fab is similar to other known Fab structures. The elbow angle, which relates the pseudo twofold axes of the VL-VH and CL-CH1 to each other is 151.4− and within the observed range for Fab molecules. The antigen binding site in 33F12 is a narrow elongated cleft, which expands at the bottom of the pocket (FIGS. 28–33). The binding pocket is more than 11 Å deep, which is comparable to those seen for antibodies raised against small haptenic groups. LysH93 is located in hydrophobic environment at the bottom of this antigen binding pocket (FIG. 30c). A second LysH52b is located at the top of CDR-H2, with its side chain pointing towards the outside of the molecule. A similiar antibody 38C2, that catalyzes the same reaction with a comparable rate enhancement, has LysH52b mutated to an Arg but retains LysH93. A sequence comparison of the CDRs with other known antibody molecules reveales some interesting and unusual features for antibody 33F12. Residue H93 is very often an Ala at this position. Only two other antibodies of known structure contain a Lys in that position, the esterolytic antibody 17E8 and the chimeric Fab fragment of the carcinoma-binding antibody B72.3. Furthermore, residue H94, which is usually an Arg, is replaced by a hydrophobic Ile in 33F12. The Arg at position H94 frequently forms a salt bridge with an aspartic acid at H101 (but in 33F12 is deleted due to the short H3 loop).

Figure 32B:
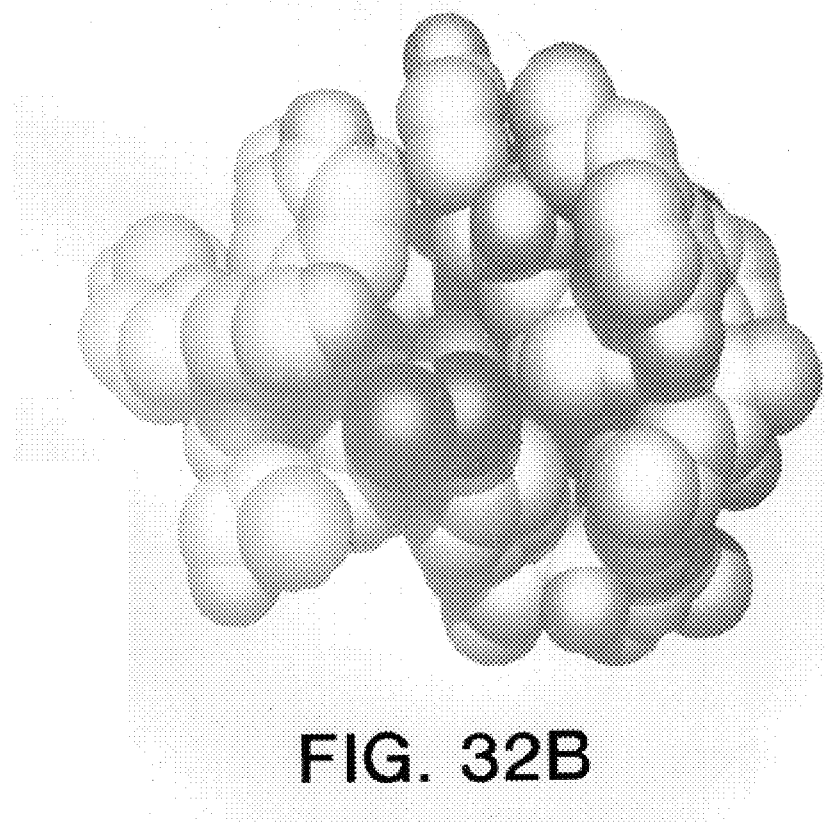

An analysis of the combining site of Fab' 33F12 (FIG. 3A) shows that LysH93 is surrounded by mostly hydrophobic side chains and is in van der Waals contact with residues LeuH4, MetH34, ValH37, CysH92, IleH94, TyrH95, SerH100,TyrH102 and TrpH103. One charged residue is within an 8 Å radius of the Nz of LysH93. The carboxyl of AspH50 is located at about 7.4 Å, too far out for any hydrogen bond or salt bridge. In addition, LysH93 does not form any hydrogen bonds with any main chain carbonyl oxygen. In B72.3, AspH101 is absent, but LysH93 forms a charged hydrogen bond with the main chain carbonyl oxygen of TyrH96, that is proposed to be responsible for the unusual CDR-H3 loop conformation. The corresponding environment for antibody 17E8 is shown in FIG. 32b. The author's also describe a hydrophobic pocket for substrate recognition (18), but, in addition, there are the charged ArgH94 and AspH101 residues. Here, the LysH93 residue forms a salt bridge to AspH101 (LysH93Nz-AspH101Od1 3.2 Å) in which the positively charged Lys is proposed to stabilize oxyanion formation. Thus, as no salt bridges can be formed in 33F12, and it appears that due to the hydrophobic environment, protonation and charge development on the e-amino group of LysH93 would be disfavored. Thus the pKa would be perturbed and allow an uncharged LysH93 to be a strong nucleophile and present it as a good candidate for selection in the reactive immunization process.

Synthesis of aldehyde 7000 as illustrated in FIG. 36

5-Oxohexanenitril (1.14 mL, 10 mmol, 1 eq.; commercially available source includes Aldrich/Sigma/Fluka), catechol (5.51 g, 50 mmol, 5 eq), and a catalytic amount of p-TsOH were refluxed in benzene (15 mL) for 12 h. After cooling to rt, the mixture was diluted with ether (50 mL) and washed with 1N NaOH for 4 times and with sat.'d ammonium chloride once. The mixture was dried ($MgSO_4$), filtered and concentrated to give 2 g (>99%) of the acetal as slightly yellow oil. This was taken up in methylene chloride (100 mL) and treated at −78° C. with 10.5 mL of 1N DIBAH in hexanes. After 2 h at −78° C. and 1h at 0° C., 3 mL of sat.'d ammonium chloride and 100 mL of ether were added and the mixture was warmed to rt. A small amount of alumina and after 10 min magnesium sulfate were added. The mixture was stirred for two h and then filtered and concentrated. Flash chromatography (9% EtOAc/hexane) gave 1545 mg (75%) of aldehyde 7000 as an oil. Spectroscopic data of the acetal: $^1$H NMR (250 MHz, CDCl$_3$) δ1.63 (s, 3 H), 1.88 (m, 2 H) 2.07 (m, 2 H), 2.40 (t, J=7.1, 2 H), 6.77 (m, 4 H); $^{13}$C NMR (63 MHz, CDCl$_3$) δ17.0, 19.2, 24.5, 37.7, 108.4, 117.8, 119.2, 121.2; HRMS Calcd for $C_{12}H_{13}NO_2$: 203.0946, obs 203.0952. Spectroscopic data for aldehyde 7: $^1$H NMR (300 MHz, CDCl$_3$) δ1.60 (s, 3 H), 1.80 (m, 2 H), 1.93 (m, 2 H), 2.48 (dt, J=1.4 and 7.2, 2 H), 6.74 (m, 4 H), 9.74 (t, J=1.4, 1 H); $^{13}$C NMR (63 MHz, CDCl$_3$) δ15.7, 24.3, 38.1, 43.3, 108.2, 121.0, 121.2, 201.8.; HRMS Calcd for $C_{12}H_{14}O_3$: 206.0943, obs 206.0948.

Antibody catalyzed synthesis of diol 8000α as illustrated in FIG. 36

To 18 ml of a 36 µM solution of antibody 38C2 (available from the Aldrich Chemical Company) in PBS-buffer (50 mM, pH=7.0) was added 1 ml of hydroxyacetone and 1 ml of a 100 mM solution (20.6 mg, 0.1 mmol) of aldehyde 7 in acetonitrile. The final concentrations were ca. 33 µM (0.66% relative to the aldehyde) of 38C2, 0.68 M of hydroxyacetone and 5 mM of aldehyde 7000. After 36 h the reaction reached 65% conversion as monitored by RP-HPLC (35% acetonitrile/water with 0.1% TFA, retention time of 8000α= 7.75 min, anti-isomer=7.34 min, 7000=15.77 min). The antibody was separated from the reaction by centrifugation in Centricon-10 concentrator tubes (Amicon). The solvent was removed under reduced pressure and the crude product was purified by RP-HPLC, to give 10.2 mg (0.036 mmol, 55% according to consumed aldehyde) of pure 8000α in more than 98% ee (the ee was determined by chiral HPLC analysis using a chiracell AD column (12% i-PrOH/hexane, 1 ml/min, λ=284 nm; on an analytical scale the ee was >99%). $^1$H NMR (250 MHz, CDCl$_3$) δ1.46–2.10 (m's, 7 H), 1.59 (s, 3 H), 2.23 (s, 3 H), 3.73 (br, 1 H), 3.95 (br, 1 H), 4.03 (br, 1 H), 6.73 (m, 4 H).$^{13}$C NMR (63 MHz, CDCl$_3$) δ19.4, 24.2, 25.1, 34.0, 38.7, 71.5, 79.1, 108.2, 118.5, 120.9, 207.9. HRMS Calcd for $C_{15}H_{20}O_5Na$:303.1208, obs 303.1216.

Synthesis of triols 9000 as illustrated in FIG. 36

Diol 8000α (10.2 mg, 0.036 mmol, 1 eq) in 10 mL of MeOH was treated with sodium boranate (3 mg, 2 eq) and stirred for 5 min.The mixture was extracted with sat.'d ammonium chloride solution and re-extracted with ether. After drying (MgSO$_4$) and evaporation in vacuum, the diastereomeric triols could be isolated by RP-HPLC. 3.9 mg (0.014 mmol, 38%) of anti-9000 and 4.4 mg (0.016 mmol, 43%) of syn-9000 were obtained as solids. Spectroscopic data of anti-9000: $^1$H NMR (250 MHz, CD$_3$OD) δ1.08 (d, J=6.3, 3 H), 1.45 (s, 3 H), 1.30–1.60 (m, 4 H), 1.89 (m, 2 H), 2.98 (br, 1 H), 3.61 (m, 2 H), 6.59 (m, 4 H).$^{13}$C NMR (63 MHz, CD$_3$OD) δ19.8, 20.6, 24.5, 34.6, 40.1, 69.7, 73.0, 78.3, 109.1, 122.0, 148.9; HRMS Calcd for $C_{15}H_{22}O_5Na$: 305.1365, obs 305.1375. Spectroscopic data of syn-9000: $^1$H NMR (250 MHz, CD$_3$OD) δ1.05 (d, J=6.4, 3 H), 1.43 (s, 3 H), 1.30–1.60 (m, 4 H), 1.80 (m, 2 H), 2.99 (br, 1 H), 3.48 (hr, 1 H), 3.67 (m, 1 H), 6.60 (m, 4 H).$^{13}$C NMR (63 MHz, CD$_3$OD) δ20.1, 20.8, 24.5, 34.6, 40.1, 68.7, 71.2, 78.3, 109.1, 120.0, 122.0, 148.9; HRMS Calcd for $C_{15}H_{22}O_5Na$: 305.1365, obs 305.1374.

Synthesis of (1S, 1'S, 5'S, 7'S)-1-(5'-Methyl-6',8'-dioxabicyclo-[3.2.1]oct-7'yl) ethanol ((−)-(1S)-1-Hydroxy-exo-brevicomin (ent-5000)) as illustrated in FIG. 36

Trial anti-9000 (4.4 mg, 0.016 mmol) and a catalytic amount of p-TsOH in 0.5 mL of benzene was heated to 60° C. for 45 min. After cooling, one drop of 25% aqueous trimethylamin and 100 mg of silicagel were added. This material was evaporated in vacuum, and then chromatographed (9% EtOAc/hexane) to give 2.7 mg (0.0154 mmol, 96%) of 1-hydroxybrevicomin ent-5000. The spectroscopic data are in full concistence with literature values. The ee was determined to be 98%.

Synthesis of (1R, 1'S, 5'S, 7'S)-1-(5'-Methyl-6',8'-dioxabicyclo[3.2.1]oct-7'yl) ethanol ((−)-(1R)-1-Hydroxy-exo-brevicomin (ent-6000)) as illustrated in FIG. 36

Trial syn-9000 (3.9 mg, 0.014 mmol) and a catalytic amount of p-TsOH in 0.5 mL of benzene was heated to 60° C. for 45 min. After cooling, one drop of 25% aqueous trimethylamin and 100 mg of silicagel were added. This material was evaporated in vacuum, and then chromatographed (9% EtOAc/hexane) to give 2.3 mg (0.013 mmol, 95%) of 1-hydroxybrevicomin ent-6000 as a liquid. The spectroscopic data are in full concistence with literature values. The ee was determined by chiral GC to be 98%.

Antibody catalyzed kinetic resolution of diol 8000

This reaction was performed on an analytical scale. Racemic aldol 8 (500 µM) and antibody 38C2 (30 µM) in PBS (pH 7.4) were incubated until 52% of the racemic mixture was consumed (ca. 10 h). The reamining aldol 8000a was isolated with an analytical RP-HPLC column and the ee was determined as described above to be >99%.

Chemical reference Syntheses of 8000α and 8000β via Horner-Wadsworth-Emmons reaction and Sharpless asymmetric dihydroxylation HWE Reaction Aldehyde 7000 (360 mg, 1.748 mmol, 1 eq), diethyl (2-oxopropyl) phosphonate (424 mg, 2.184 mmol, 1.25 eq) and lithium hydroxide monohydrate (101 mg, 2.412 mmol, 1.38 eq) were stirred in 5 mL of anhydrous THF for 3 h. The mixture was diluted with 5 mL of ether and 0.3 mL of sat.'d ammonium chloride solution were added. The mixture was dried (MgSO$_4$), filtered and concentrated. Filtration over silica gel (50% EtOAc/hexane) gave 430 mg (>99%) of the α, β unsaturated methyl ketone, as a liquid. $^1$H NMR (300 MHz, CDCl$_3$) δ1.60 (s, 3 H), 1.58–1.70 (m, 2 H), 1.90–2.00 (m, 2 H), 2.22 (s, 3 H), 2.20–2.30 (m, 2 H), 6.05 (d, J=15.9, 1 H), 6.75 (m, 5 H) ; $^{13}$C NMR (63 MHz, CDCl$_3$) δ19.2, 24.5, 26.8, 32.0, 37.6, 108.2, 108.3, 120.9, 121.2, 131.5, 147.3, 203.8. HRMS Calcd for $C_{15}H_{18}O_3Na$: 269.1154, obs 269.1161.

Synthesis of Diol 8000a by Sharpless-AD as shown on FIG. 36

The α,β unsaturated methyl ketone (300 mg, 1.22 mmol, 1 eq) in 12 mL of t-BuOH/water (1:1) was treated with AD-mix-α (1.73 g) and methanesulfonamide (120 mg) at 0° C. and stirred for 3 h at 0° C. and for 16 h at rt. Sodium metabisulfite (2.48 g) was carefully added and the mixture was extracted with ethyl acetate (5×). After drying (MgSO$_4$), evaporation in vacuum, and chromatography (35% EtOAc/hexane) 299 mg (88%) of pure diol 8α were obtained as solid. The ee was determined as described above to be 89%.

Synthesis of Diol 8000β as shown on FIG. 37

The α,β unsaturated methyl ketone (300 mg, 1.22 mmol, 1 eq) in 12 mL of t-BuOH/water (1:1) was treated with AD-mix-β (1.73 g) and methanesulfonamide (120 mg) at 0C and stirred for 3 h at 0° C. and for 16 h at rt. Sodium metabisulfite (2.48 g) was carefully added and the mixture was extracted with ethyl acetate (5×). After drying (MgSO$_4$), evaporation in vacuum, and chromatography (35% EtOAc/hexane) 290 mg (85%) of pure diol 8000β were obtained as solid. The ee was determined as described above to be 91%.

Chemical reference Syntheses of diol 11000α and diol 11000β via Mulzer sequence and Sharpless asymmetric dihydroxylation as shown on FIG. 38

Aldehyde 10000

Ethyl levulinate (7.1 mL, 50 mmol, 1 eq), catechol (27.53 g, 250 mmol, 5 eq), and a catalytic amount p-TsOH were refluxed in benzene (200 mL) for 12 h. After cooling to rt, the mixture was diluted with ether (250 mL) and washed with 1N NaOH for 4 times and with sat.'d ammonium chloride once. The mixture was dried (MgSO$_4$), filtered and concentrated to give 11.89 (>99%) of the levulinate acetal as slightly yellow oil. This material (2.36 g, 10 mmol) was taken up in methylene chloride (100 mL) and treated at −78° C. with 10.5 mL of 1N DIBAH in hexanes. After 30 min at −78° C., 3 mL of sat.'d ammonium chloride and 100 mL of ether were added and the mixture was warmed to rt. A small amount of alumina and after 10 min magnesium sulfate were added. The mixture was stirred for two hours and then filtered and concentrated. For the following chemical step, this material was pure enough. For the antibody catalyzed step: Flash chromatography (9% EtOAc/hexane) gave 1.83 g (95%) of aldehyde 10000 as an oil. Spectroscopic data of the acetal: $^1$H NMR (250 MHz, CDCl$_3$) δ1.12 (t, J=7.1, 3 H); 1.53 (s, 3 H), 2.20 (m, 2 H), 2.38 (m, 2 H), 4.02 (q, J=7.1, 2 H), 6.66 (m, 4 H); $^{13}$C NMR (63 MHz, CDCl$_3$) δ14.1, 24.6, 28.2, 34.2, 60.53, 108.4, 121.14, 147.3, 172.8; Spectroscopic data of 10000: $^1$H NMR (300 MHz, CDCl$_3$) δ1.64 (s, 3 H), 2.31 (t, J=7.6, 2 H), 2.62 (t, 7.6, 2 H), 6.76 (m, 4 H), 9.76 (s, 1 H); $^{13}$C NMR (63 MHz, CDCl$_3$) δ24.6, 31.4, 37.6, 108.4, 121.3, 147.1, 200.8.

Synthesis of α,β unsaturated ethyl ketone as illustrated in FIG. 38

Methyl methanephosphonate (1.95 mL, 18 mmol, 3.6 eq) in 15 mL of anhydrous ether was treated at −78° C. with a 2.5 M solution of n-BuLi (7.2 mL, 18 mmol, 3.6 eq). After 30 min the ester (881 mg, 10 mmol, 2 eq) in 7 mL of anhydrous ether was slowly added and the mixture was stirred for 1 h at −78° C. and for 30 min at 0° C. Water (360 mg, 20 mmol, 4 eq) in 40 mL of THF and then aldehyde 10000 (960 mg, 5 mmol, 1 eq) were added. After 1 h, the mixture was diluted with 65 mL of ether and 3 mL of sat.'d ammonium chloride solution were added. The mixture was dried (MgSO$_4$), filtered and concentrated. Chromatography (9% EtOAc/hexane) gave 960 mg (78%) of the α,β unsaturated ethyl ketone, as a liquid. $^1$H NMR (250 MHz, CDCl$_3$) δ1.06 (t, J=7.3, 3 H), 1.62 (s, 3 H), 2.09 (m, 2 H), 2.37 (m, 2 H), 2.50 (q, J=7.3, 3 H), 6.04 (dt, J=1.5 and 15.8, 1 H), 6.75 (m, 4 H), 6.81 (dt, J=6.8 and 15.8, 1 H); $^{13}$C NMR (63 MHz, CDCl$_3$) δ8.0, 24.6, 26.1, 33.3, 37.5, 108.3, 117.9, 121.1, 130.7, 145.2, 147.2, 200.7. HRMS Calcd for C$_{15}$H$_{18}$O$_3$: 246.1256, obs 246.1262.

Synthesis of Diol 11000α as illustrated in FIG. 38

The α,β unsaturated ethyl ketone (400 mg, 1.626 mmol, 1 eq) in 16 mL of t-BuOH/water (1:1) was treated with AD-mix-α (2.3 g) and methanesulfonamide (160 mg) at 0° C. and stirred for 3 h at 0° C. and for 36 h at rt. Sodium metabisulfite (3.38 g) was carefully added and the mixture was extracted with ethyl acetate (5×). After drying (MgSO$_4$), evaporation in vacuum, and chromatography (gradient, 35%, 50% EtOAc/hexane) 355 mg (78%) of pure diol 11000α (ee=91%, HPLC) as a solid and 85 mg (21%) of starting material were obtained. $^1$H NMR (250 MHz, CDCl$_3$) δ1.12 (t, J=7.3, 3 H), 1.64 (s, 3 H), 1.86 (m, 3 H), 2.15 (m, 2 H), 2.52 (m, 2 H), 3.75 (br, 1 H), 4.00 (br, 1 H), 4.05 (br, 1 H), 6.77 (m, 4 H).$^{13}$C NMR (63 MHz, CDCl$_3$) δ7.4, 28.2, 31.0, 35.4, 71.6, 78.6, 108.4, 118.6, 121.1, 147.7, 210.6. HRMS Calcd for C$_{15}$H$_{20}$O$_5$Na: 303.1208, obs 303.1198.

Synthesis of Diol 11000β as illustrated in FIG. 38

The α,β unsaturated ethyl ketone (400 mg, 1.626 mmol, 1 eq) in 16 mL of t-BuOH/water (1:1) was treated with AD-mix-β (2.3 g) and methyl sulfonamide (160 mg) at 0° C. and stirred for 3 h at 0° C. and for 36 h at rt. Sodium metabisulfite (3.38 g) was carefully added and the mixture was extracted with ethyl acetate (5×). After drying (MgSO$_4$), evaporation in vacuum, and chromatography (gradient, 35%, 50% EtOAc/hexane) 322 mg (71%) of pure diol 11000β (ee=92%, HPLC) as a solid and 114 mg (28%) of starting material were obtained. $^1$H NMR (250 MHz, CDCl$_3$) δ1.12 (t, J=7.3, 3 H), 1.64 (s, 3 H), 1.86 (m, 3 H) 2.15 (m, 2 H), 2.52 (m, 2 H), 3.75 (br, 1 H), 4.00 (br, 1 H), 4.05 (br, 1 H), 6.77 (m, 4 H). $^{13}$C NMR (63 MHz, CDCl$_3$) δ7.4, 28.2, 31.0, 35.4, 71.6, 78.6, 108.4, 118.6, 121.1, 147.7, 210.6.

Synthesis of diol 11000α by antibody catalysis

This reaction was performed on an analytical scale. Aldehyde 10000 (500 μM), 1-hydroxy-2-butanone (5% v/v) and antibody 38C2 (30 μM) were incubated for ca. 5 h. The aldol product was separated on an analytical RP-HPLC column and the ee (>99%) was determined as mentioned in the preparation of 8000α.

Kinetic resolution of diol 11000 by antibody catalysis

This reaction was performed on an analytical scale. Racemic aldol 11000 (5 mM) and antibody 38C2 (104 μM) in PBS (pH 7.4) were incubated until 54% of the racemic mixture was consumed (ca. 10 h). The reamining aldol 11000β was isolated with an analytical RP-HPLC column and the ee was determined as described above to be >99%.

Synthesis of 2-hydroxybrevicomins 3000 and 4000 as illustrated in FIG. 38

Triols 12

Diol 11000α from Sharpless AD, ee=91% (140 mg, 0.5 mmol, 1 eq) in 5 mL of MeOH was treated with sodium boranate (38 mg, 2 eq) and stirred for 5 min. The mixture was extracted with sat.'d ammonium chloride solution and re-extracted with ether. After drying (MgSO$_4$) and evaporation in vacuum, 141 mg (>99%) of pure diastereomeric triols 12000 were isolated. For analytical reasons the triols can be separated by RP-HPLC. Spectroscopic data for anti-12000: $^1$H NMR (250 MHz, CD$_3$OD) δ0.86 (t, J=7.1, 3 H), 1.25 (m, 1 H), 1.49 (s, 3 H), 1.60 (m, 3 H), 1.85 (m, 1 H), 2.00 (m, 1 H), 3.00 (br, 1 H), 3.40 (br, 1 H), 3.72 (br, 1 H), 6.60 (m, 4 H).$^{13}$C NMR (63 MHz, CD$_3$OD) δ10.2, 24.6, 27.4, 28.5, 36.8, 1.5, 74.1, 76.7, 109.1, 120.0, 122.1, 149.0; HRMS Calcd for C$_{15}$H$_{22}$O$_5$Na: 305.1365, obs 305.1358. syn-12000: HRMS Calcd for C$_{15}$H$_{22}$O$_5$Na: 305.1365, obs 305.1371.

(1R, 2S, 5S, 7R)- and (1R, 2S, 5S, 7S)-7-Ethyl-5-methyl-6,6-dioxabicyclo [3.2.1]octan-2-ol) ((+)-(2S)-2-Hydroxy-exo-brevicomin and (+)-(2S)-2-Hydroxy-endo-brevicomin (4000 and 3000) as illustrated in FIG. 38

Trioles 12000 (141 mg, 0.5 mmol) and a catalytic amount of p-TsOH in 10 mL of benzene were heated to 60° C. for 45 min. After cooling, 30 drops of 25% aqueous trimethylamine and 500 mg of silicagel were added. This material was evaporated in vacuum, and then chromatographed (gradient 9%, 12% EtOAc/hexane) to give 40 mg (46%) of 4000 as a solid and 40 mg (46%) of 3 as a liquid. The spectroscopic data of 3000 are in full concistence with literature values: $^1$H NMR (250 MHz, C$_6$D$_6$) δ0.90 (t, J=7.4, 3 H), 1.12 (br, 1 H), 1.43 (s, 3 H), 1.30–1.70 (m, 6 H), 3.62 (m, 1 H), 3.80 (d, J=3.7, 1 H), 4.18 (t, J=6.5, 1 H).$^{13}$C NMR (63 MHz, C$_6$D$_6$) δ10.0, 24.3, 26.9, 28.8, 35.4, 66.2, 77.3, 80.9, 107.4. Spectroscopic data of 4000: $^1$H NMR (250 MHz, CDCl$_3$) δ0.96 (t, J=7.4, 3 H), 1.02 (br, 1 H), 1.48 (s, 3 H), 1.67–2.10 (m, 6 H), 3.32 (dt, J=3.1 and 8.1, 1 H), 3.52 (dd, J=4.1 and 9.0, 1 H), 4.30 (m, 1 H).$^{13}$C NMR (63 MHz, CDCl$_3$) δ9.5, 23.5, 23.6, 25.4, 33.8, 68.1, 74.9, 78.0;

Synthesis of Compound 1111 as illustrated in FIG. 41

Benzyloxyacetaldehyde (80 mg, 0.53 mmol) in ) in ) 0.5 mL of acetonitrile, was added to 9 mL of a solution of antibody 38C2 (35 mg, 0.23 mmol) in PBS (phosphate buffer saline, 100 mM), followed by the addition of of hydroxyacetone. (0.5 mL, 6.3 mmol). After 48 hr at room temperature the reaction reached 56% conversion and the mixture was freeze dried. The remaining residue was extracted with methylene chloride. The solvent was removed under reduced pressure and the crude product was purified by column chromatography (silica gel, ethyl acetate/hexane, 1/1) to give pure 2111α (39 mg, 0.17 mmol, 32%) in 97% ee. Benzyl ether 2111α (39 mg, 0.17 mmol) was dissolved in 1 mL of methanol and hydrogenated with a catalytic amount of palladium hydroxide on carbon. After two hr, the mixture was filtered through celite and the solvent was removed under reduced pressure to give pure 1-deoxy-L-xylulose 1111 (19 mg, 0.14 mmol, 81%).

EXAMPLE 3

Enantioselective Aldol-Cyclodehydrations Catalyzed by Antibody 38C2

Enantioselective reactions typically rely on the differentiation between the two enantiotopic faces of a sp$^2$ carbon center. Most often this center is connected to an oxygen, a nitrogen, or another carbon atom via a double bond. Examples include the asymmetric dihydroxylation (AD) and the catalytic enantioselective hydrogenation of olefins. A different type of enantioselectivity is observed in reactions where two enantiotopic groups are differentiated (FIG. 44). Despite a few known small molecule catalysts, natural enzymes dominate this reaction-class. Examples include the esterase catalyzed enantioselective hydrolysis of meso-diesters and the reverse reaction, the lipase catalyzed desymmetrization of meso-diols.

While catalytic antibodies have been shown to be efficient catalysts for enantioface-differentiating reaction and enantiomer-differentiating kinetic resolutions, enantiogroup-differentiating reactions with catalytic antibodies have rarely been reported. This study shows the use of aldolase antibody 38C2 for the enantiogroup-differentiating aldol cyclodehydration of 4-substituted-2,6-heptanediones to give enantiomerically enriched 5-substituted-3-methyl-2-cyclohexen-1-ones.

Aldolase antibody 38C2 (Aldrich #47,995-0) has been shown to be a highly efficient and enantioselective catalyst for both aldol and retro-aldol reactions with rate accelerations approaching those of natural aldolase enzymes. Furthermore, and in contrast to its natural counterparts, this antibody is a broad scope aldol catalyst that has been shown to work with over 200 different substrate combinations. Antibody 38C2 has been used in the enantioselective synthesis of naturally occurring pheromone derivatives, deoxysugars, and in a total synthesis of epothilone A. Furthermore, we have shown its use in a preparative scale synthesis of the Wieland-Miescher ketone (2) from achiral triketone 1 (FIG. 45). Traditionally, this reaction is catalyzed by (L)-proline. However, here the product is obtained with an ee of 71%. A related transformation that has been catalyzed by (L)-proline is the enantioselective cyclodehydration of 4-substituted-2, 6-heptanediones (3) to the 5-substituted-3-methyl-2-cyclohexen-1-ones (4) (FIG. 46). Stereochemically, both reactions are enantiogroup-differentiating and probably occur via an enamine mechanism. However, in the former case the enantiodifferentiation follows enamine formation, while in the latter case, enantiodifferentiation occurs upon enamine formation.

In the (L)-proline-catalyzed reaction typically low yields and enantioselectivities are observed.

We found that antibody 38C2 catalyzes the cyclodehydration of 3 (R=H) quite efficiently with $k_{cat}$=0.082 min$^{-1}$, $K_M$=2 mM and $k_{cat}/k_{uncat}$=1.2×10$^7$ (FIG. 47). The question was, whether Ab 38C2 was capable of catalyzing this transformation with enantiogroup-selectivity when provided with substrates 3 where R H.

For the synthesis of the starting 1,5-diketones 3a–c, we followed a route that has been developed by Sakurai and coworkers. Thus, Lewis-acid mediated conjugate addition of allyltrimethylsilane to α,β-unsaturated ketones 5a–c gave olefins 6a–c. Wacker-oxidation of δ,ε-unsaturated ketones 6a–c then furnished diketones 3a–c. Interestingly, we found that the Wacker-oxidation did not require an oxygen atmosphere. Simple stirring under air furnished the products in equivalent yield. Racemic reference compounds 4a–c can be prepared by base treatment (KOH/MeOH) of ketones 3a–c (FIG. 48).

The results of the antibody catalyzed cyclization of diketones 3 are shown in FIG. 49.

Ab 38C2 (10 μM, 2 mol %) catalyzes the cyclodehydration of diketones 3a–c (500 μM in phosphate buffered saline (PBS), pH 7.4, 10% CH$_3$CN) very efficiently to give the (S)-configured products 4a–c with yields generally exceeding 95%.

The enantioselectivity of these reactions is moderate to good. The ee's were determined by chiral-phase HPLC analysis. To determine the absolute configuration of enones 4a–c, we used the products from the (L)-proline-catalyzed reaction as a reference standard. This transformation is known to give the corresponding (R)-isomers (FIG. 50).

All products obtained from the (L)-proline-catalyzed reactions had a configuration opposite that of the products produced in the antibody catalyzed reaction as determined by chiral-phase HPLC analyses. Interestingly, and in contrast to these results, in the Wieland-Miescher case both (L)-proline and 38C2 gave the same enantiomer.

In summary aldolase antibody 38C2 has been shown to be an efficient catalyst for the enantiogroup differentiating cyclodehydration of 4-substituted 2,6-heptanediones. The observed enantioselectivities are modest in comparison to the exceptional high ee's that are usually obtained in aldol additions and retro-aldol reactions catalyzed by Antibody 38C2. However, product yields, purities, and to some extent enantioselectivities are far better than those obtained from the corresponding (L)-proline catalyzed reactions.

This study was supported in part by the NIH (CA27489).

What is claimed:

1. A method for catalyzing an aldol condensation between an aldol donor substrate and an aldol acceptor substrate for producing a β-hydroxy ketone, said aldol donor substrate being either a ketone donor substrate or an aldehyde donor substrate and said aldol acceptor substrate being either a ketone acceptor substrate or an aldehyde acceptor substrate, the method comprising the following steps:

Step A: admixing a catalytically effective amount of a catalytic antibody having aldol addition activity or of a catalytically active molecule containing an antibody combining site portion of said catalytic antibody with sufficient amounts of said aldol donor substrate and of said aldol acceptor substrate in a reaction medium for producing a reaction admixture, said aldol donor substrate including a reactive carbonyl group and an unbranched carbon adjacent to said carbonyl group, said catalytic antibody or said catalytically active molecule being of the type which includes a lysine residue which forms a Schiff base intermediate with the reactive carbonyl group of said aldol donor substrate; and then Step B: maintaining said reaction admixture of said Step A for a period of time sufficient for said catalytic antibody or said catalytically active molecule to catalyze said aldol condensation between said aldol donor substrate and said aldol acceptor substrate for producing said β-hydroxy ketone;

wherein the following proviso applies:

if the aldol donor substrate is the ketone donor substrate and the aldol acceptor substrate is the aldehyde acceptor substrate, then the ketone donor substrate is not an unfunctionalized open chain aliphatic ketone.

2. The method for catalyzing an aldol condensation as described in claim 1 wherein said aldol acceptor substrate is said aldehyde acceptor substrate and said aldol donor substrate is said ketone donor substrate selected from the group consisting of aliphatic cyclic ketones, functionalized open chain aliphatic ketones, and functionalized cyclic ketones.

3. The method for catalyzing an aldol condensation as described in claim 2 comprising the following additional step:

after said Step B;

Step C: maintaining said reaction admixture of said Step B for a further period of time in the presence of said catalytic antibody or said catalytically active molecule for converting said β-hydroxy ketone to a β-unsaturated ketone product by an elimination reaction.

4. The method for catalyzing an aldol condensation as described in claim 2 comprising the following additional step:

after said Step B;

Step C: converting said β-hydroxy ketone to a dihydroxy product by reduction.

5. The method for catalyzing an aldol condensation as described in claim 1 wherein said aldol donor substrate is the ketone donor substrate and said aldol acceptor substrate is said ketone acceptor substrate.

6. The method for catalyzing an aldol condensation as described in claim 5 comprising the following additional step:

after said Step B;

Step C: maintaining said reaction admixture of said Step B for a further period of time in the presence of said catalytic antibody or said catalytically active molecule for converting said β-hydroxy ketone to a β-unsaturated ketone product by an elimination reaction.

7. The method for catalyzing an aldol condensation as described in claim 5 comprising the following additional step:

after said Step B;

Step C: converting said β-hydroxy ketone to a dihydroxy product by reduction.

8. The method for catalyzing an aldol condensation as described in claim 1 wherein said aldol donor substrate is the aldehyde donor substrate and said aldol acceptor substrate is said aldehyde acceptor substrate.

9. The method for catalyzing an aldol condensation as described in claim 8 comprising the following additional step:

after said Step B;

Step C: maintaining said reaction admixture of said Step B for a further period of time in the presence of said catalytic antibody or said catalytically active molecule for converting said β-hydroxy ketone to a β-unsaturated ketone product by an elimination reaction.

10. The method for catalyzing an aldol condensation as described in claim 8 comprising the following additional step:

after said Step B;

Step C: converting said β-hydroxy ketone to a dihydroxy product by reduction.

11. The method for catalyzing an aldol condensation as described in claim 1 wherein said aldol donor substrate is the aldehyde donor substrate and said aldol acceptor substrate is said ketone acceptor.

12. The method for catalyzing an aldol condensation as described in claim 11 comprising the following additional step:

after said Step B;

Step C: maintaining said reaction admixture of said Step B for a further period of time in the presence of said catalytic antibody or said catalytically active molecule for converting said β-hydroxy ketone to a β-unsaturated ketone product by an elimination reaction.

13. The method for catalyzing an aldol condensation as described in claim 11comprising the following additional step:

after said Step B;

Step C: converting said β-hydroxy ketone to a dihydroxy product by reduction.

14. The method for catalyzing an aldol condensation as described in claim 1 wherein said aldol condensation is intramolecular, both said aldol donor substrate and said aldol acceptor substrate are a single reactant molecule, and said aldol condensation causes a cylization of said single reactant molecule for forming a cyclic β-hydroxy ketone.

15. The method for catalyzing an aldol condensation as described in claim 14 comprising the following additional step:

after said Step B;

Step C: maintaining said reaction admixture of said Step B for a further period of time in the presence of said catalytic antibody or said catalytically active molecule for converting said cyclicβ-hydroxy ketone to a cyclic β-unsaturated ketone product by an elimination reaction.

16. The method for catalyzing an aldol condensation as described in claim 14 comprising the following additional step:

after said Step B;
Step C: converting said cyclic β-hydroxy ketone to a cyclic dihydroxy product by reduction.

17. The method for catalyzing an aldol condensation as described in claim 1 wherein said aldol condensation is a self-aldol condensation and both said aldol donor substrate and said aldol acceptor substrate are a single ketone reactant molecule.

18. The method for catalyzing an aldol condensation as described in claim 17 comprising the following additional step:

after said Step B;
Step C: maintaining said reaction admixture of said Step B for a further period of time in the presence of said catalytic antibody or said catalytically active molecule for converting said β-hydroxy ketone to a β-unsaturated ketone product by an elimination reaction.

19. A method for catalyzing an aldol condensation between an aldol donor substrate and an aldol acceptor substrate for producing a β-hydroxy ketone, said aldol donor substrate being either a ketone donor substrate or an aldehyde donor substrate substrate, said aldol acceptor substrate being either a ketone acceptor substrate or an aldehyde acceptor substrate, the method comprising the following steps:

Step A: admixing a catalytically effective amount of a catalytic antibody having aldol addition activity or of a catalytically active molecule containing an antibody combining site portion of said catalytic antibody with sufficient amounts of said aldol donor substrate and of said aldol acceptor substrate in a reaction medium for producing a reaction admixture, said catalytic antibody or said catalytically active molecule being of the type which includes a lysine residue which forms a Schiff base intermediate with said aldol donor substrate, said aldol donor substrate unbranched at a non-bond-forming α position; and then Step B: maintaining said reaction admixture of said Step A for a period of time sufficient for said catalytic antibody or said catalytically active molecule to catalyze said aldol condensation between said aldol donor substrate and said aldol acceptor substrate for producing said β-hydroxy ketone and for converting said β-hydroxy ketone to a β-unsaturated ketone product by an elimination reaction.

* * * * *